US006849431B2

(12) United States Patent
Okamoto et al.

(10) Patent No.: US 6,849,431 B2
(45) Date of Patent: Feb. 1, 2005

(54) NON-B, NON-C, NON-G HEPATITIS VIRUS GENE, POLYNUCLEOTIDE, POLYPEPTIDE, VIRUS PARTICLE, METHOD FOR ISOLATING VIRUS PARTICLE, AND METHOD FOR DETECTING VIRUS

(75) Inventors: Hiroaki Okamoto, Tochigi (JP); Tsutomu Nishizawa, Nara (JP)

(73) Assignee: Ryoji Tamura, Saitama (JP)

( * ) Notice: Subject to any disclaimer, the term of this patent is extended or adjusted under 35 U.S.C. 154(b) by 0 days.

(21) Appl. No.: 10/781,599

(22) Filed: Feb. 18, 2004

(65) Prior Publication Data

US 2004/0176583 A1 Sep. 9, 2004

Related U.S. Application Data

(63) Continuation of application No. 09/463,488, filed as application No. PCT/JP98/03340 on Jul. 27, 1998, now abandoned.

(30) Foreign Application Priority Data

Jul. 25, 1997 (JP) .............................. 9-233246
Oct. 9, 1997 (JP) .............................. 9-314196
Mar. 13, 1998 (JP) .............................. 10-82962

(51) Int. Cl.[7] .............................. C12P 19/34
(52) U.S. Cl. ................ 435/91.2; 435/91.32; 435/91.33; 536/23.72; 536/24.3; 536/24.32; 536/24.33
(58) Field of Search .............................. 435/91.2, 91.32, 435/91.33; 536/23.72, 24.3, 24.32, 24.33

(56) References Cited

FOREIGN PATENT DOCUMENTS

| EP | 0 339 668 | 11/1989 |
|---|---|---|
| JP | 09-299-078 | 11/1997 |
| WO | WO 93/15111 A | 8/1993 |

OTHER PUBLICATIONS

Nishizawa, et al. "A Novel DNA Virus (TTV) Associated with Elevated Transaminase Levels in Posttransfusion hepatitis of Unknown Etiology," *Biochemical and Biophysical Research Communications*, vol. 241, pp. 92–97, 1997.
Okamoto, et al. "Fecal Excretion of a Nonenveloped DNA Virus (TTV) Associated with Posttransfusion Non–A–G Hepatitis," *Journal of Medical Virology*, vol. 56, pp. 128–132, 1998.

Okamoto, et al. "Molecular Cloning and Characterization of a Novel DNA Virus (TTV) Associated with Posttransfusion Hepatitis of Unknown Etiology," *Hepatology Research*, vol. 10, pp. 1–16, 1998.
Simmonds, et al. "Detection of a Novel DNA Virus (TTV) in Blood Donors and Blood Products," *The Lancet*, vol. 352, pp. 191–195, Jul. 18, 1998.
Takahashi, et al. "Partial—2.4–kb Sequences of TT Virus (TTV) Genome from Eight Japanese Isolates: Diagnostic and Phylogenetic Implications," *Hepatology Research*, vol. 12, pp. 111–120, 1998.
International Search Report issued to a related, foreign patent application.
Okamoto, et al. "Molecular Cloning and Characterization of a Novel DNA Virus (TTV) Associated with Posttransfusion Hepatitis of Unknown Etiology," *Hepatology Research*, vol. 10, pp. 1–16, 1998.
GENBANK nucleotide sequence AB008394 (Mar. 14, 1009).
Kuwada, et al. "Non–A, Non–B Fulminant Hepatitis is Also Non–E and Non–C," *The American Journal of Gastroenterology*, vol. 89, No. 1, pp. 57–61, 1994.
Fiordalisi, et al. "High Prevalence of GB Virus C Infection in a Group of Italian Patients with Hepatitis of Unknown Etiology," *Journal of Infectious Diseases*, vol. 174, No. 1, pp. 181–183, 1996.
Database EMBL Sequences, Accession No. B21160, Sep. 20, 1997.
Okamoto, et al. *Virology*, vol. 259, pp. 437–448, 1999.

*Primary Examiner*—Laurie Scheiner
(74) *Attorney, Agent, or Firm*—Knobbe, Martens, Olson & Bear, LLP

(57) ABSTRACT

By isolating a so far unknown novel hepatitis virus and determining the gene sequence thereof, genes, polynucleotides, polypeptides, methods for isolating virus particles, virus particles, and antiviral antibodies, which can be used for diagnosis and treatment, as well as methods for detecting viruses are provided. Disclosed is a non-B, non-C, non-G hepatitis virus gene having a nucleotide sequence from which a sequence having a length of from about 3500 nucleotides to about 4000 nucleotides can be amplified by PCR utilizing an oligonucleotide having the nucleotide sequence shown in SEQ ID NO: 57 and an oligonucleotide having the nucleotide sequence shown in SEQ ID NO: 60 as primers, or PCR utilizing an oligonucleotide having the nucleotide sequence shown in SEQ ID NO: 57 and an oligonucleotide having the nucleotide sequence shown in SEQ ID NO: 61 as primers. Based on the nucleotide sequence of the gene, polypeptides etc. are provided.

4 Claims, 16 Drawing Sheets

FIG 2

```
1) CACCAGGAGCATATACAGACATAAGTACAATCCATTCACAGACAGAGGAGAAGGCAACA    60
2) ............................................................
3) ............................................................

1) TGTTATGGATAGACTGGCTAAGCAAAAAAAACATGAACTATGACAAAGTACAAAGTAAAT   120
2) ............................................................
3) ............................................................

1) GCTTAATATCAGACCTACCTCTATGGGCAGCAGCATATGGATATGTAGAATTTTGTGCAA   180
2) ............................................................
3) ............................................................

1) AAAGTACAGGAGACCAGAACATACACAGACCCCAGGCTACTAATAAGAAGTCCCTTTA    240
2) ............................................................
3) ............................................................

1) CAGACCCCACAACTACTAGTACACACAGACCCCACAAAGGCTTTGTTCCTTACTCTTTAA   300
2) ............................................................
3) ............................................................

1) ACTTTGGAAATGGTAAAATGCCAGGAGTAGTAGTAATGTGCCTATTAGAATGAGAGCTA   360
2) ............................................................
3) ............................................................

1) AATGGTATCCAACATTATTTCACCAGCAAGAAGTAC   396
2) ....................................
3) ....................................
```

1) PILOT BLOOD FOR TRANSFUSION
2) PATIENT: 2 WEEKS AFTER BLOOD TRANSFUSION
3) PATIENT: 4 WEEKS AFTER BLOOD TRANSFUSION

FIG 7

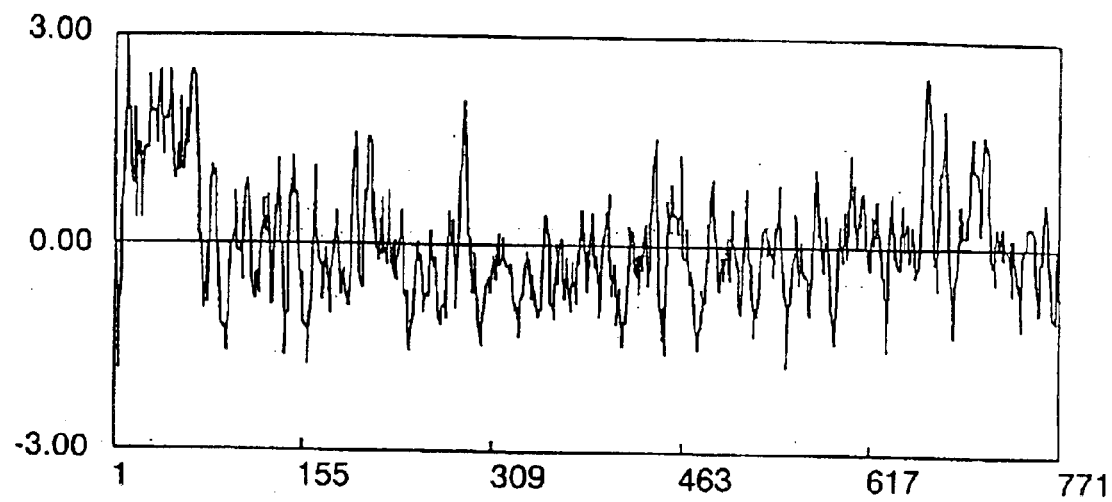
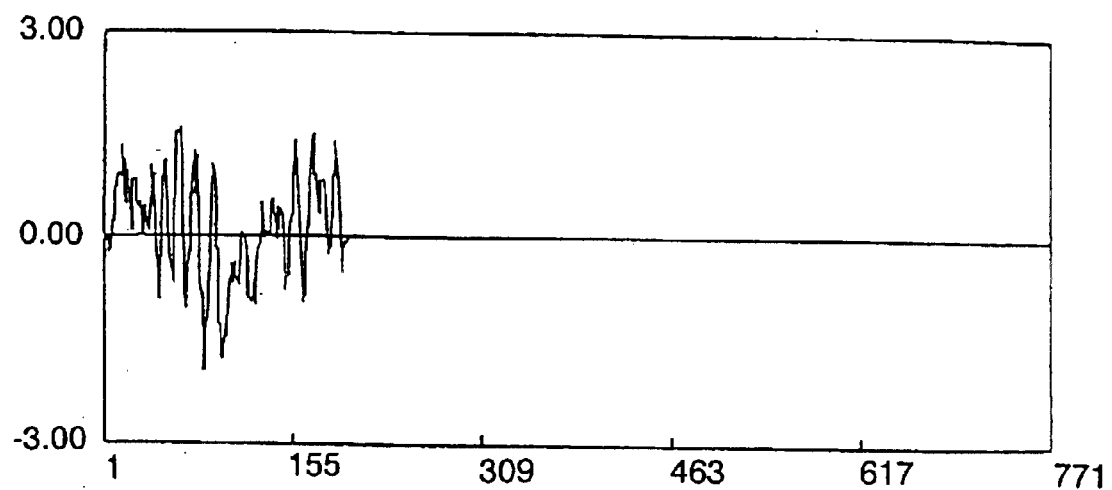
FIG 9

FIG 11

```
N22(222nc)      161:CCTTTACAGACCCACAACTACTAGTACACACAGACCCCACAAAGGCTTTGTTCCTTACTCTGTA  222
TA278(222nc)    161:.............................................................T..  222
TX011(222nc)    161:.T.........C.G...A...........................................T..T.  222
TS003(222nc)    161:....A....TA.T.G.G.....AC.....ACA..AG.CTT.GG..A.AC..A..C...AGCA...  222
NA004(222nc)    161:....AC...TG...........AT....ACA.............A.AC..A..C....AG.T.T  222
KN1-32/KA       161:....AC...TA..........G..GT...AC......ACA.T....CTC.G...A.AC..A..G...AGCT.T  222
KN1-54/KK       161:....AC...TA..........G..GT...AC......ACA.T....CTC.G...A.AC..A..G...AGCT.T  222
KN1-8/KO        161:....AC...TA..........G..GT...AC......ACA.T....CTC.G...A.AC..A..G...AGCT.T  222
KB212NG1074D/TM 161:....A....TA..........G..GT...AC......ACA......CTC.G...A.AC..A..G...AGCT.T  222
KB6/MT          161:....AC..TACA..T...A.GA.....AC......ACAC..AC......CTT.G......T.A..........A..TAG.T.C  222
KC277/MH        161:....AC..TACA..T...A.GA.....AC......ACAC..AC......TCT..G......A.AGTA...AGCT.T  222
KN428/TK        161:....AC..TACA..T......A.GA.....AC......ACAC..AC......TCT..G......A.AGTA...AGCT.T  222
THEM3186(222)   161:...AC..TACA..T...A.GA.....AC......ACAC..AC......TCT..G......A.AGTA...AGCT.T  222
FC93-1SS/TTV(222) 161:A.AC...T....CATG..G....AC....T..A..GA.CT.C........A.TG...AGCAA.  222
HD/K.MINEKI(222) 161:...AC.....G......G.G.....AAC......ACA.....T.TC.G..G..C..GTT......CTAC  222
THEM3199(222)   161:..G.AC...T....T.G..TA.AA...ACA.TGA..ACTGG........C..C..TAGC.A..  222
THM332          161:A.AC......A....C....GACCTCGA.AGACA...ACT..TG..A..CA..A..A..TGACTAT  222
THM5-45         161:A.AC......T..C.CC..CTAT.ACA.AGACA..A.AGAC.TG.....ACC.A......TGACTAC  225
K70-56          161:..AC..TC.A..G.CCA.GTACAA..CTGGCA.GGTACA..CT....AC..TTC..TGACACT  225
K60-26          161:..AC..TC.G......CCA.GTACAAG.CTGGCAGAATACA..T......AC..TTC..TGACACT  225
K66-46          161:..AC..TC.G..G.CCA.GTACAAG.CAGGCA..GTACA...T.....A.....TTC..TGACACT  225
                161:..T.AC..T..G..C.CCA.GTAT.ACA.G..TA.....A.AC.GT.....AC.AG.A..TGACAC.  225
```

FIG 12

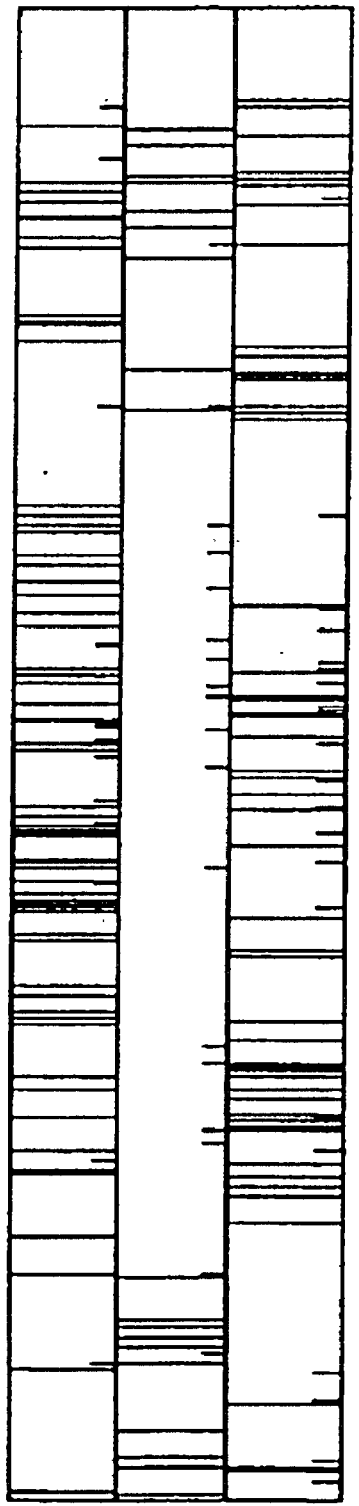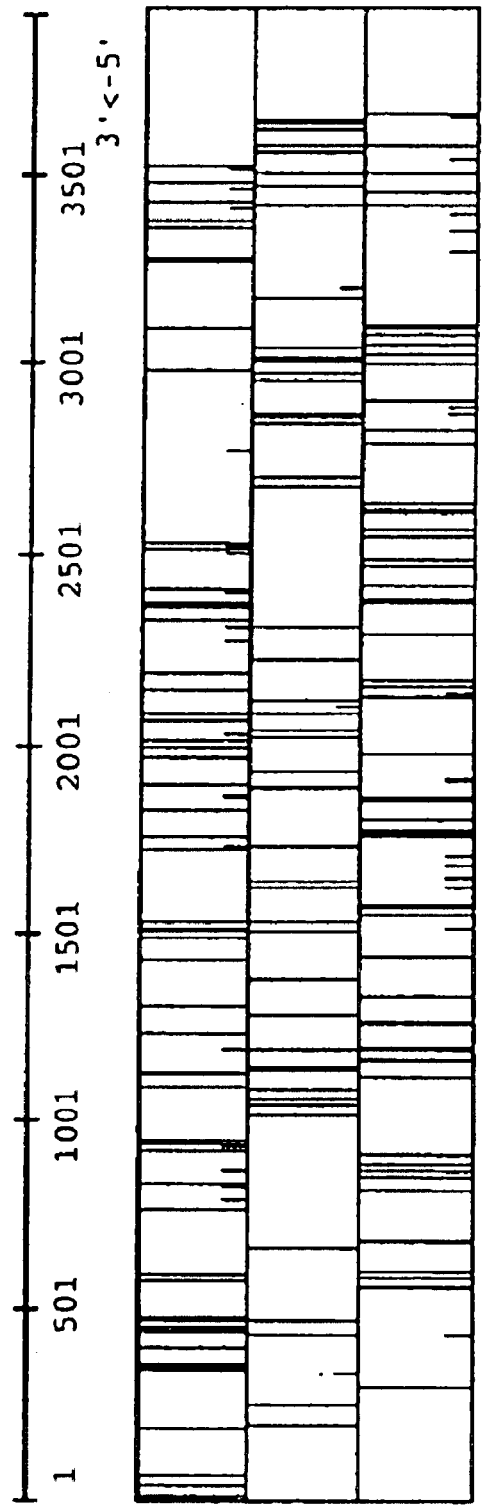
FIG 14

COMPARISON OF 5' END REGION SEQEUNCES OF HNT22 (1:) AND TUS01 (2:)

```
1: ATTTGCTAC GTCACTAACC ACGTGACACC CACAGGCCAA CCGAATGCTA TGTCATCCAT   60
2: TTTTGCTAC GTCACTAACC ACGTGACTCC CGCAGGCCAA CCCAGTACTA TGTCGTCCAC   60

1: TTCCTGGGCC GGGTCTACGT CCTCATATAA GTAAGTGCAC TTCCGAATGG CTGAGTTTTC  120
2: TTCCTGGGAC GAGTCTACGT CCTGATATAA GTAAGTGCAC TTCCGAATGG CTGAGTTTTC  120

1: CACGCCCGTC CGCAGCGGTG AAGCCACCGG AGGGAGATC  TCTCGCCGTCC CGAGGGCGGG  180
2: CACGCCCGTC CGCAGCGGAG AACGCCACGG AGGGGAGTTC CGCGCGTC   CGAGGGCGGG  180

1: TGCCGAAGGT GAGTTTACAC ACCGAAGTCA AGGGGCAATT CGGGCTCGGG ACTGGCCGGG  240
2: TGCCGGAGGT GAGTTTACAC ACCGCAGTCA AGGGGCAATT CGGGCTCGGG ACTGGCCGGG  240

1: CTATGGGCAA GGCTCTGAAA AAATGCATGT TTATTGGCAG GCATTACAGA AAGAAAAGGG  300
2: CCCCGGGCAA GGCTCTTAAA AAATGCACTT TTCTTGTCAG TAGTGCAGA GCGAAAAGGA  300
```

FIG 15

COMPARISON OF 3' END REGION SEQEUNCES OF HNT22 (1:) AND TUS01 (2:)

FIG 16

SEQUENCE LISTING

<160> NUMBER OF SEQ ID NOS: 64

<210> SEQ ID NO 1
<211> LENGTH: 3739
<212> TYPE: DNA
<213> ORGANISM: non-B, non-C, non-G hepatitis virus
<220> FEATURE:
<221> NAME/KEY: CDS
<222> LOCATION: 589..2898
<220> FEATURE:
<221> NAME/KEY: CDS
<222> LOCATION: 107..712

<400> SEQUENCE: 1

```
attttgctac gtcactaacc acgtgacacc cacaggccaa ccgaatgcta tgtcatccat        60
ttcctgggcc gggtctacgt cctcatataa gtaagtgcac ttccgaatgg ctgagttttc       120
cacgcccgtc cgcagcggtg aagccacgga gggagatctc cgcgtcccga gggcgggtgc       180
cgaaggtgag tttacacacc gaagtcaagg ggcaattcgg gctcgggact ggccgggcta       240
tgggcaaggc tctgaaaaaa gcatgtttat tggcaggcat tacagaaaga aagggcgct        300 gtcactgtgt gctgtgcgaa caacaaagaa ggcttgcaaa ctactaatag taatgtggac       360
cccacctcgc aatgatcaac actaccttaa ctggcaatgg tactcaagta tacttagctc       420
ccacgctgct atgtgcgggt gtcccgacgc tgtcgctcat tttaatcatc ttgcttctgt       480
gcttcgtgcc ccgcaaaacc caccccctcc cggtccccag cgaaacctgc ccctccgacg       540
gctgccggct ctcccggctg cgccagaggc gcccggagat agagcaccat ggcctatggc       600
tggtggcgcc gaaggagaag acggtggcgc aggtggagac gcagaccatg gaggcgccgc       660
tggaggaccc gaagacgcag acctgctaga cgccgtggcc gccgcagaaa cgtaaggaga       720
cgccgcagag gagggaggtg gaggaggaga tataggagat ggaaaagaaa gggcaggcgc       780
agaaaaaaag ctaaaataat aataagacaa tggcaaccaa actacagaag gagatgtaac       840
atagtaggct acatccctgt actaatatgt ggcgaaaata ctgtcagcag aaactatgcc       900
acacactcag acgataccaa ctacccagga ccctttgggg ggggtatgac tacagacaaa       960
tttactttaa gaattctgta tgacgagtac aaaaggttta tgaactactg gacagcatct      1020
aacgaagacc tagacctttg tagatatcta ggagtaaacc tgtacttttt cagacaccca      1080
gatgtagatt ttatcataaa aattaatacc atgcctcctt ttctagacac agaactcaca      1140
gcccctagca tacacccagg catgctagcc ctagacaaaa gagcaagatg gatacctagc      1200
ttaaaatcta gaccgggaaa aaaacactat attaaaataa gagtaggggc accaagaatg      1260
ttcactgata aatggtaccc ccaaacagat ctttgtgaca tggtgcttct aactgtctat      1320
gcaaccgcag cggatatgca atatccgttc ggctcaccac taactgactc tgtggttgtg      1380
aacttccagg ttctgcaatc catgtatgat aaaacaatta gcatattacc agacgaaaaa      1440
tcacaaagag aaattctact taacaagata gcaagttaca ttcccttttta taataccaca      1500
```

-continued

```
caaactatag cccaattaaa gccatttata gatgcaggca atgtaacatc aggcgcaaca    1560
gcaacaacat gggcatcata cataaacaca accaaattta ctacagcaac cacaacaact    1620
tatgcatatc caggcaccaa cagaccccca gtaactatgt taacctgtaa tgactcctgg    1680
tacagaggaa cagtatataa cacacaaatt caacagttac caataaaagc agctaaatta    1740
tacttagagg caacaaaaac cttgctagga aacaccttca caaatgagga ctacacacta    1800
gaatatcatg gaggactgta cagctcaata tggctatccc ctggtagatc ttactttgaa    1860
acaacaggag catatacaga cataaagtac aatccattca cagacagagg agaaggcaac    1920
atgttatgga tagactggct aagcaaaaaa aacatgaact atgacaaagt acaaagtaaa    1980
tgcttaatat cagacctacc tctatgggca gcagcatatg gatatgtaga attttgtgca    2040
aaaagtacag gagaccaaaa catacacatg aatgccaggc tactaataag aagtcccttt    2100
acagacccac aactactagt acacacagac cccacaaaag ctttgttcc ttactcttta    2160 aactttggaa atggtaaaat gccaggaggt agtagtaatg tgcctattag aatgagagct    2220
aaatggtatc caacattatt tcaccagcaa gaagtactag aggccttagc acagtcaggc    2280 cccttttgcat accactcaga cattaaaaaa gtatctctgg gtatgaaata ccgttttaag    2340
tggatctggg gtggaaaccc cgttcgccaa caggttgtta gaaatccctg caaagaaacc    2400
cactcctcgg gcaatagagt ccctagaagc ttacaaatcg ttgacccgaa atacaactca    2460
ccggaactca cattccatac ctgggacttc agacgtggcc tctttggccc gaaagctatt    2520
cagagaatgc aacaacaacc aacaactact gacattttt cagcaggccg caagagaccc    2580
aggagggaca ccgaggtgta ccactccagc caagaagggg agcaaaaaga aagcttactt    2640 ttcccccccag tcaagctcct cagacgagtc ccccgtgggg aagactcgca gcaggaggaa    2700
agcgggtcgc aaagctcaga ggaagagacg cagaccgtct cccagcagct caagcagcag    2760
ctgcagcaac agcgaatcct gggagtcaaa ctcagactcc tgttcaacca gtccaaaaa    2820 atccaacaaa atcaagatat caaccctacc ttgttaccaa ggggggggga tctagcatcc    2880
ttatttcaaa tagcaccata acatgtttttg gtgaccccaa accttacaac ccttccagta    2940
atgactggaa agaggagtac gaggcctgta gaatatggga cagacccccc agaggcaacc    3000
taagagatac ccctttctac ccctgggccc caaggaaaaa ccagtaccgt gtaaacttta    3060
aacttggatt ccaataaagc taggccgtgg gactttcact tgtcggtgtc tgcttataaa    3120
agtaactaag cactccgagc gaagcgagga gtgcgaccct tgggggctca acgccttcgg    3180
agccgcgcgc tacgccttcg gctgcgcgcg gcacctcaga ccccccgctcg tgctgacacg    3240 ctcgcgcgtg tcagaccact tcgggctcgc ggggggtcggg aaatttacta aacagactcc    3300
gagttgccat tggactcagg agctatgaat cagtaacgaa agtgagtggg gccagacttc    3360
gccataaggc ctttatcttc ttgccatttg tcagtaacag gggtcgccat agacttcggc    3420
ctccacttta ccttgtaaaa actaccaaaa tggccgttcc agtgacgtca cagccgccat    3480
tttaagtagc tgacgtcaag gattgacgta aaggttaaag gtcatcctcg gcggaagcta    3540
cacaaaatgg tggacaacat cttccgggtc aaaggttgtg cgtacgtcac aagtcacgtg    3600
gaggggaccc gctgtaaccc ggaagtaggc ccgtcacgt gacttaccac gtgtgtacac    3660
gtcaccgccg ccatttttgtt ttacaaaatg gctgacttcc ttcctctttt ttgaaaaaag    3720
gcgccaaaaa accgtcggc                                                3739
```

<210> SEQ ID NO 2

```
<211> LENGTH: 20
<212> TYPE: DNA
<213> ORGANISM: Artificial Sequence
<220> FEATURE:
<223> OTHER INFORMATION: Synthetic DNA

<400> SEQUENCE: 2
gcagcagcat atggatatgt                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA

<400> SEQUENCE: 3
tgactgtgct aaagcctcta                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
catacacatg aatgccaggc                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
gtacttcttg ctggtgaaat                                                    20

<210> SEQ ID NO 6
<211> LENGTH: 24
<212> TYPE: DNA
<213> ORGANISM: Artificial Sequence
<220> FEATURE:
<223> OTHER INFORMATION: Synthetic DNA

<400> SEQUENCE: 6
acagacagag gagaaggcaa catg                                               24

<210> SEQ ID NO 7
<211> LENGTH: 24
<212> TYPE: DNA
<213> ORGANISM: Artificial Sequence
<220> FEATURE:
<223> OTHER INFORMATION: Synthetic DNA

<400> SEQUENCE: 7
ggcaacatgy trtggataga ctgg                                               24

<210> SEQ ID NO 8
<211> LENGTH: 25
<212> TYPE: DNA
<213> ORGANISM: Artificial Sequence
<220> FEATURE:
<223> OTHER INFORMATION: Synthetic DNA

<400> SEQUENCE: 8
```
ctggcatttt accatttcca aagtt            25

<210> SEQ ID NO 9
<211> LENGTH: 770
<212> TYPE: PRT
<213> ORGANISM: non-B, non-C, non-G hepatitis virus

<400> SEQUENCE: 9

| | | | | | | | | | | | | | | |
|---|---|---|---|---|---|---|---|---|---|---|---|---|---|---|
| Met | Ala | Tyr | Gly | Trp | Trp | Arg | Arg | Arg | Arg | Arg | Trp | Arg | Arg |
| 1 | | | | 5 | | | | | 10 | | | | | 15 |
| Trp | Arg | Arg | Arg | Pro | Trp | Arg | Arg | Trp | Arg | Thr | Arg | Arg | Arg |
| | | | 20 | | | | | 25 | | | | | 30 |
| Arg | Pro | Ala | Arg | Arg | Gly | Arg | Arg | Arg | Asn | Val | Arg | Arg | Arg |
| | | | 35 | | | | | 40 | | | | | 45 |
| Arg | Arg | Gly | Gly | Arg | Trp | Arg | Arg | Tyr | Arg | Arg | Trp | Lys | Arg |
| | | | 50 | | | | | 55 | | | | | 60 |
| Lys | Gly | Arg | Arg | Arg | Lys | Lys | Ala | Lys | Ile | Ile | Ile | Arg | Gln | Trp |
| | | | 65 | | | | | 70 | | | | | | 75 |
| Gln | Pro | Asn | Tyr | Arg | Arg | Arg | Cys | Asn | Ile | Val | Gly | Tyr | Ile | Pro |
| | | | | 80 | | | | | 85 | | | | | 90 |
| Val | Leu | Ile | Cys | Gly | Glu | Asn | Thr | Val | Ser | Arg | Asn | Tyr | Ala | Thr |
| | | | | 95 | | | | | 100 | | | | | 105 |
| His | Ser | Asp | Asp | Thr | Asn | Tyr | Pro | Gly | Pro | Phe | Gly | Gly | Gly | Met |
| | | | | | 110 | | | | | 115 | | | | | 120 |
| Thr | Thr | Asp | Lys | Phe | Thr | Leu | Arg | Ile | Leu | Tyr | Asp | Glu | Tyr | Lys |
| | | | | 125 | | | | | 130 | | | | | 135 |
| Arg | Phe | Met | Asn | Tyr | Trp | Thr | Ala | Ser | Asn | Glu | Asp | Leu | Asp | Leu |
| | | | | 140 | | | | | 145 | | | | | 150 |
| Cys | Arg | Tyr | Leu | Gly | Val | Asn | Leu | Tyr | Phe | Phe | Arg | His | Pro | Asp |
| | | | | 155 | | | | | 160 | | | | | 165 |
| Val | Asp | Phe | Ile | Ile | Lys | Ile | Asn | Thr | Met | Pro | Pro | Phe | Leu | Asp |
| | | | | 170 | | | | | 175 | | | | | 180 |
| Thr | Glu | Leu | Thr | Ala | Pro | Ser | Ile | His | Pro | Gly | Met | Leu | Ala | Leu |
| | | | | 185 | | | | | 190 | | | | | 195 |
| Asp | Lys | Arg | Ala | Arg | Trp | Ile | Pro | Ser | Leu | Lys | Ser | Arg | Pro | Gly |
| | | | | 200 | | | | | 205 | | | | | 210 |
| Lys | Lys | His | Tyr | Ile | Lys | Ile | Arg | Val | Gly | Ala | Pro | Arg | Met | Phe |
| | | | | 215 | | | | | 220 | | | | | 225 |
| Thr | Asp | Lys | Trp | Tyr | Pro | Gln | Thr | Asp | Leu | Cys | Asp | Met | Val | Leu |
| | | | | 230 | | | | | 235 | | | | | 240 |
| Leu | Thr | Val | Tyr | Ala | Thr | Ala | Ala | Asp | Met | Gln | Tyr | Pro | Phe | Gly |
| | | | | 245 | | | | | 250 | | | | | 255 |
| Ser | Pro | Leu | Thr | Asp | Ser | Val | Val | Asn | Phe | Gln | Val | Leu | Gln |
| | | | | 260 | | | | | 265 | | | | | 270 |
| Ser | Met | Tyr | Asp | Lys | Thr | Ile | Ser | Ile | Leu | Pro | Asp | Glu | Lys | Ser |
| | | | | 275 | | | | | 280 | | | | | 285 |
| Gln | Arg | Glu | Ile | Leu | Leu | Asn | Lys | Ile | Ala | Ser | Tyr | Ile | Pro | Phe |
| | | | | 290 | | | | | 295 | | | | | 300 |
| Tyr | Asn | Thr | Thr | Gln | Thr | Ile | Ala | Gln | Leu | Lys | Pro | Phe | Ile | Asp |
| | | | | 305 | | | | | 310 | | | | | 315 |
| Ala | Gly | Asn | Val | Thr | Ser | Gly | Ala | Thr | Ala | Thr | Trp | Ala | Ser |
| | | | | 320 | | | | | 325 | | | | | 330 |
| Tyr | Ile | Asn | Thr | Thr | Lys | Phe | Thr | Ala | Thr | Thr | Thr | Tyr |
| | | | | 335 | | | | | 340 | | | | | 345 |

```
Ala Tyr Pro Gly Thr Asn Arg Pro Val Thr Met Leu Thr Cys
            350                 355                 360

Asn Asp Ser Trp Tyr Arg Gly Thr Val Tyr Asn Thr Gln Ile Gln
            365                 370                 375

Gln Leu Pro Ile Lys Ala Ala Lys Leu Tyr Leu Glu Ala Thr Lys
            380                 385                 390

Thr Leu Leu Gly Asn Thr Phe Thr Asn Glu Asp Tyr Thr Leu Glu
            395                 400                 405

Tyr His Gly Gly Leu Tyr Ser Ser Ile Trp Leu Ser Pro Gly Arg
            410                 415                 420

Ser Tyr Phe Glu Thr Thr Gly Ala Tyr Thr Asp Ile Lys Tyr Asn
            425                 430                 435

Pro Phe Thr Asp Arg Gly Glu Gly Asn Met Leu Trp Ile Asp Trp
            440                 445                 450

Leu Ser Lys Lys Asn Met Asn Tyr Asp Lys Val Gln Ser Lys Cys
            455                 460                 465

Leu Ile Ser Asp Leu Pro Leu Trp Ala Ala Ala Tyr Gly Tyr Val
            470                 475                 480

Glu Phe Cys Ala Lys Ser Thr Gly Asp Gln Asn Ile His Met Asn
            485                 490                 495

Ala Arg Leu Leu Ile Arg Ser Pro Phe Thr Asp Pro Gln Leu Leu
            500                 505                 510

Val His Thr Asp Pro Thr Lys Gly Phe Val Pro Tyr Ser Leu Asn
            515                 520                 525

Phe Gly Asn Gly Lys Met Pro Gly Gly Ser Ser Asn Val Pro Ile
            530                 535                 540

Arg Met Arg Ala Lys Trp Tyr Pro Thr Leu Phe His Gln Gln Glu
            545                 550                 555

Val Leu Glu Ala Leu Ala Gln Ser Gly Pro Phe Ala Tyr His Ser
            560                 565                 570

Asp Ile Lys Lys Val Ser Leu Gly Met Lys Tyr Arg Phe Lys Trp
            575                 580                 585

Ile Trp Gly Gly Asn Pro Val Arg Gln Gln Val Val Arg Asn Pro
            590                 595                 600

Cys Lys Glu Thr His Ser Ser Gly Asn Arg Val Pro Arg Ser Leu
            605                 610                 615

Gln Ile Val Asp Pro Lys Tyr Asn Ser Pro Glu Leu Thr Phe His
            620                 625                 630

Thr Trp Asp Phe Arg Arg Gly Leu Phe Gly Pro Lys Ala Ile Gln
            635                 640                 645

Arg Met Gln Gln Gln Pro Thr Thr Thr Asp Ile Phe Ser Ala Gly
            650                 655                 660

Arg Lys Arg Pro Arg Arg Asp Thr Glu Val Tyr His Ser Ser Gln
            665                 670                 675

Glu Gly Glu Gln Lys Glu Ser Leu Leu Phe Pro Pro Val Lys Leu
            680                 685                 690

Leu Arg Arg Val Pro Pro Trp Glu Asp Ser Gln Gln Glu Glu Ser
            695                 700                 705

Gly Ser Gln Ser Ser Glu Glu Thr Gln Thr Val Ser Gln Gln
            710                 715                 720

Leu Lys Gln Gln Leu Gln Gln Gln Arg Ile Leu Gly Val Lys Leu
            725                 730                 735
```

```
Arg Leu Leu Phe Asn Gln Val Gln Lys Ile Gln Gln Asn Gln Asp
                740                 745                 750

Ile Asn Pro Thr Leu Leu Pro Arg Gly Gly Asp Leu Ala Ser Leu
                755                 760                 765

Phe Gln Ile Ala Pro
                770

<210> SEQ ID NO 10
<211> LENGTH: 202
<212> TYPE: PRT
<213> ORGANISM: non-B, non-C, non-G hepatitis virus

<400> SEQUENCE: 10

Met Ala Glu Phe Ser Thr Pro Val Arg Ser Gly Glu Ala Thr Glu
  1               5                  10                  15

Gly Asp Leu Arg Val Pro Arg Ala Gly Ala Glu Gly Glu Phe Thr
                 20                  25                  30

His Arg Ser Gln Gly Ala Ile Arg Ala Arg Asp Trp Pro Gly Tyr
                 35                  40                  45

Gly Gln Gly Ser Glu Lys Ser Met Phe Ile Gly Arg His Tyr Arg
                 50                  55                  60

Lys Lys Arg Ala Leu Ser Leu Cys Ala Val Arg Thr Thr Lys Lys
                 65                  70                  75

Ala Cys Lys Leu Leu Ile Val Met Trp Thr Pro Pro Arg Asn Asp
                 80                  85                  90

Gln His Tyr Leu Asn Trp Gln Trp Tyr Ser Ser Ile Leu Ser Ser
                 95                 100                 105

His Ala Ala Met Cys Gly Cys Pro Asp Ala Val Ala His Phe Asn
                110                 115                 120

His Leu Ala Ser Val Leu Arg Ala Pro Gln Asn Pro Pro Pro Pro
                125                 130                 135

Gly Pro Gln Arg Asn Leu Pro Leu Arg Arg Leu Pro Ala Leu Pro
                140                 145                 150

Ala Ala Pro Glu Ala Pro Gly Asp Arg Ala Pro Trp Pro Met Ala
                155                 160                 165

Gly Gly Ala Glu Gly Glu Asp Gly Gly Ala Gly Gly Asp Ala Asp
                170                 175                 180

His Gly Gly Ala Ala Gly Gly Pro Glu Asp Ala Asp Leu Leu Asp
                185                 190                 195

Ala Val Ala Ala Ala Glu Thr
                200

<210> SEQ ID NO 11
<211> LENGTH: 500
<212> TYPE: DNA
<213> ORGANISM: non-B, non-C, non-G hepatitis virus

<400> SEQUENCE: 11
gatcttactt tgaaacaaca ggagcatata cagacataaa gtacaatcca ttcacagaca      60
gaggagaagg caacatgtta tggatagact ggctaagcaa aaaaaacatg aactatgaca     120
aagtacaaag taaatgctta atatcagacc tacctctatg gcagcagca tatggatatg      180 tagaattttg tgcaaaaagt acaggagacc aaaaacataca catgaatgcc aggctactaa    240
taagaagtcc ctttacagac ccacaactac tagtacacac agaccccaca aaaggctttg     300
ttccttactc ttttaaactt ggaaatggta aaatgccagg aggtagtagt aatgtgccta     360
```

```
ttagaatgag agctaaatgg tatccaacat tatttcacca gcaagaagta ctagaggcct      420
tagcacagtc aggccccttt gcataccact cagacattaa aaaagtatct ctgggtatga      480
aataccgttt taagtggatc                                                  500

<210> SEQ ID NO 12
<211> LENGTH: 41
<212> TYPE: DNA
<213> ORGANISM: Artificial Sequence
<220> FEATURE:
<223> OTHER INFORMATION: Synthetic DNA

<400> SEQUENCE: 12
aaggatccgt cgacatcgat aatacggggg ggggggggg g                           41

<210> SEQ ID NO 13
<211> LENGTH: 41
<212> TYPE: DNA
<213> ORGANISM: Artificial Sequence
<220> FEATURE:
<223> OTHER INFORMATION: Synthetic DNA

<400> SEQUENCE: 13
aaggatccgt cgacatcgat aatacgaaaa aaaaaaaaa a                           41

<210> SEQ ID NO 14
<211> LENGTH: 41
<212> TYPE: DNA
<213> ORGANISM: Artificial Sequence
<220> FEATURE:
<223> OTHER INFORMATION: Synthetic DNA

<400> SEQUENCE: 14
aaggatccgt cgacatcgat aatacgtttt ttttttttt t                           41

<210> SEQ ID NO 15
<211> LENGTH: 41
<212> TYPE: DNA
<213> ORGANISM: Artificial Sequence
<220> FEATURE:
<223> OTHER INFORMATION: Synthetic DNA

<400> SEQUENCE: 15
aaggatccgt cgacatcgat aatacgcccc ccccccccc c                           41

<210> SEQ ID NO 16
<211> LENGTH: 803
<212> TYPE: DNA
<213> ORGANISM: non-B, non-C, non-G hepatitis virus

<400> SEQUENCE: 16
cctacttgag aatataacaa gttacattcc cttttataat accacacaaa ctatagccca       60
attaaagcca tttatagatg caggcaatgt aacatcaggc gcaacagcaa caacatgggc      120
atcatacata aacacaacca aatttactac agcaaccaca acaacttatg catatccagg      180
caccaacaga ccccccagtaa ctatgttaac ctgtaatgac tcctggtaca gaggaacagt      240
atataacaca caaattcaac agttaccaat aaaagcagct aaattatact tagaggcaac      300
aaaaaccttg ctaggaaaca ccttcacaaa tgaggactac acactagaat atcatggagg      360
actgtacagc tcaatatggc tatcccctgg tagatcttac tttgaaacaa caggagcata      420
tacagacata aagtacaatc cattcacaga cagaggagaa ggcaacatgt tatgatagaa      480
ctggctaagc aaaaaaaaca tgaactatga caaagtacaa agtaaatgct taatatcaga      540
```

```
cctacctcta tgggcagcag catatggata tgtagaattt tgtgcaaaaa gtacaggaga      600
ccaaaacata cacatgaatg ccaggctact aataagaagt ccctttacag acccacaact      660
actagtacac acagacccca caaaaggctt tgttccttac tctttaaact ttggaaatgg      720
taaaatgcca ggaggtagta gtaatgtgcc tattagaatg agagctaaat ggtatccaac      780
attatttcac cagcaagaag tac                                              803

<210> SEQ ID NO 17
<211> LENGTH: 1205
<212> TYPE: DNA
<213> ORGANISM: non-B, non-C, non-G hepatitis virus

<400> SEQUENCE: 17
catacacatg aatgccaggc tactaataag aagtcccttt acagacccac aactactagt       60
acacacagac cccacaaaag ctttgttcc ttactctttta aactttggaa atggtaaaat      120
gccaggaggt agtagtaatg tgcctattag aatgagagct aaatggtatc caacattatt      180
tcaccagcaa gaagtactag aggccttagc acagtcaggc ccctttgcat accactcaga      240
cattaaaaaa gtatctctgg gtatgaaata ccgttttaag tggatctggg gtggaaaccc      300
cgttcgccaa caggttgtta gaaatccctg caaagaaacc cactcctcgg gcaatagagt      360
ccctagaagc ttacaaatcg ttgacccgaa atacaactca ccggaactca cattccatac      420
ctgggacttc agacgtggcc tctttggccc gaaagctatt cagagaatgc aacaacaacc      480
aacaactact gacatttttt cagcaggccg caagagaccc aggagggaca ccgaggtgta      540
ccactccagc caagaagggg agcaaaaaga agcttactt tccccccag tcaagctcct       600 cagacgagtc ccccgtgggg aagactcgca gcaggaggaa agcgggtcgc aaagctcaga      660
ggaagagacg cagaccgtct cccagcagct caagcagcag ctgcagcaac agcgaatcct      720
gggagtcaaa ctcagactcc tgttcaacca agtccaaaaa atccaacaaa atcaagatat      780
caaccctacc ttgttaccaa ggggggggga tctagcatcc ttatttcaaa tagcaccata      840
aacatgtttg gtgaccccaa accttacaac ccttccagta atgactggaa agaggagtac      900
gaggcctgta gaatatggga cagaccccc agaggcaacc taagagatac ccctttctac      960
ccctgggccc ccaaggaaaa ccagtaccgt gtaaacttta aacttggatt ccaataaagc     1020
taggccgtgg gactttcact tgtcggtgtc tgcttataaa agtaactaag cactccgagc     1080
gaagcgagga gtgcgaccct tggggctca acgccttcgg agccgcgcgc tacgccttcg     1140
gctgcgcgcg gcacctcaga ccccgctcg tgctgacacg ctcgcgcgtg tcagaccact     1200
tcggg                                                                 1205

<210> SEQ ID NO 18
<211> LENGTH: 20
<212> TYPE: DNA
<213> ORGANISM: Artificial Sequence
<220> FEATURE:
<223> OTHER INFORMATION: Synthetic DNA

<400> SEQUENCE: 18
ggtgcctgga tatgcataag                                                   20

<210> SEQ ID NO 19
<211> LENGTH: 20
<212> TYPE: DNA
<213> ORGANISM: Artificial Sequence
<220> FEATURE:
```

<223> OTHER INFORMATION: Synthetic DNA

<400> SEQUENCE: 19
tgcccatgtt gttgctgttg                    20

<210> SEQ ID NO 20
<211> LENGTH: 32
<212> TYPE: DNA
<213> ORGANISM: Artificial Sequence
<220> FEATURE:
<223> OTHER INFORMATION: Synthetic DNA
<220> FEATURE:
<221> NAME/KEY: misc_difference
<222> LOCATION: 27..31
<223> OTHER INFORMATION: n=a, t, g or c

<400> SEQUENCE: 20
aaggatccgt cgacatcgat aatacgnnnn ng      32

<210> SEQ ID NO 21
<211> LENGTH: 631
<212> TYPE: DNA
<213> ORGANISM: non-B, non-C, non-G hepatitis virus

<400> SEQUENCE: 21
tatgactaca gacaaattta ctttaagaat tctgtatgac gagtacaaaa ggtttatgaa      60
ctactggaca gcatctaacg aagacctaga cctttgtaga tatctaggag taaacctgta     120 cttttttcaga cacccagatg tagattttat cataaaaatt aataccatgc ctccttttct    180
agacacagaa ctcacagccc ctagcataca cccaggcatg ctagccctag acaaaagagc     240
aagatggata cctagcttaa aatctagacc gggaaaaaaa cactatatta aaataagagt     300
aggggcacca agaatgttca ctgataaatg gtacccccaa acagatcttt gtgacatggt     360
gcttctaact gtctatgcaa ccgcagcgga tatgcaatat ccgttcggct caccactaac     420
tgactctgtg gttgtgaact tccaggttct gcaatccatg tatgataaaa caattagcat     480
attaccagac gaaaaatcac aaagagaaat tctacttaac aagatagcaa gttacattcc     540
cttttataat accacacaaa ctatagccca attaaagcca tttatagatg caggcaataa     600
accatcaggc acaacagcaa caacatgggc a                                    631

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA

<400> SEQUENCE: 22
tcacttgtcg gtgtctgctt                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic DNA

<400> SEQUENCE: 23
ctaagcactc cgagcgtagc                    20

<210> SEQ ID NO 24
<211> LENGTH: 614

-continued

<212> TYPE: DNA
<213> ORGANISM: non-B, non-C, non-G hepatitis virus

<400> SEQUENCE: 24

```
ctaagcactc cgagcgtagc gaggagtgcg acccttgggg gctcaacgcc ttcggagcca    60
cgcgctacgc cttcggctgc gcgcggcacc tcagaccccc gctcgtgctg acacgctcgc   120
gcgtgtcaga ccacttcggg ctcgcggggg tcgggaaatt tactaaacag actccgagtt   180
gccattggac tcaggagcta tgaatcagta acgaaagtga gtggggccag acttcgccat   240
aaggccttta tcttcttgcc atttgtcagt aacaggggtc gccatagact tcggcctcca   300
ctttaccttg taaaaactac caaaatggcc gttccagtga cgtcacagcc gccattttaa   360
gtagctgacg tcaaggattg acgtaaaggt taaaggtcat cctcggcgga agctacacaa   420
aatggtggac aacatcttcc gggtcaaagg ttgtgcgtac gtcacaagtc acgtggaggg   480
gacccgctgt aacccggaag taggcccccgt cacgtgactt accacgtgtg tacacgtcac   540
cgccgccatt ttgttttaca aatggctgac ttccttcct ctttttttgaa aaaggcgcc    600
aaaaaaccgt cggc                                                     614
```

<210> SEQ ID NO 25
<211> LENGTH: 302
<212> TYPE: DNA
<213> ORGANISM: non-B, non-C, non-G hepatitis virus

<400> SEQUENCE: 25

```
ccgcagagga gggaggtgga ggaggagata taggagatgg aaaagaaagggcaggcgcag    60
aaaaaaagct aaaataataa taagacaatg gcaaccaaac tacagaagga gatgtaacat   120
agtaggctac atccctgtac taatatgtgg cgaaaatact gtcagcagaa actatgccac   180
acactcagac gataccaact acccaggacc ctttgggggg ggtatgacta cagacaaatt   240
tactttaaga attctgtatg acgagtacaa aaggtttatg aactactgga cagcatctaa   300
cg                                                                  302
```

<210> SEQ ID NO 26
<211> LENGTH: 831
<212> TYPE: DNA
<213> ORGANISM: non-B, non-C, non-G hepatitis virus

<400> SEQUENCE: 26

```
attttgctac gtcactaacc acgtgacacc cacaggccaa ccgaatgcta tgtcatccat    60
ttcctgggcc gggtctacgt cctcatataa gtaagtgcac ttccgaatgg ctgagttttc   120
cacgcccgtc cgcagcggtg aagccacgga gggagatctc cgcgtcccga gggcgggtgc   180
cgaaggtgag tttacacacc gaagtcaagg ggcaattcgg gctcgggact ggccgggcta   240
tgggcaaggc tctgaaaaaa gcatgtttat tggcaggcat tacagaaaga aaagggcgct   300
gtcactgtgt gctgtgcgaa caacaaagaa ggcttgcaaa ctactaatag taatgtggac   360
cccacctcgc aatgatcaac actaccttaa ctggcaatgg tactcaagta tacttagctc   420
ccacgctgct atgtgcgggt gtcccgacgc tgtcgctcat tttaatcatc ttgcttctgt   480
gcttcgtgcc ccgcaaaacc cacccctctc cggtccccag cgaaacctgc ccctccgacg   540
gctgccggct ctcccggctg cgccagaggc gcccggagat agagcaccat ggcctatggc   600
tggtggcgcc gaaggagaag acggtggcgc aggtggagac gcagaccatg gaggcgccgc   660
tggaggaccc gaagacgcag acctgctaga cgccgtggcc gccgcagaaa cgtaaggaga   720
```

-continued

```
cgccgcagag gagggaggtg gaggaggaga tataggagat ggaaaagaaa gggcaggcgc    780
agaaaaaaag ctaaaataat aataagacaa tggcaaccaa actacagaag g            831
```

<210> SEQ ID NO 27
<211> LENGTH: 20
<212> TYPE: DNA
<213> ORGANISM: Artificial Sequence
<220> FEATURE:
<223> OTHER INFORMATION: Synthetic DNA

<400> SEQUENCE: 27

```
atctacatct gggtgtctga                                                20
```

<210> SEQ ID NO 28
<211> LENGTH: 20
<212> TYPE: DNA
<213> ORGANISM: Artificial Sequence
<220> FEATURE:
<223> OTHER INFORMATION: Synthetic DNA

<400> SEQUENCE: 28

```
cgttagatgc tgtccagtag                                                20
```

<210> SEQ ID NO 29
<211> LENGTH: 20
<212> TYPE: DNA
<213> ORGANISM: Artificial Sequence
<220> FEATURE:
<223> OTHER INFORMATION: Synthetic DNA

<400> SEQUENCE: 29

```
cgccacatat tagtacaggg                                                20
```

<210> SEQ ID NO 30
<211> LENGTH: 20
<212> TYPE: DNA
<213> ORGANISM: Artificial Sequence
<220> FEATURE:
<223> OTHER INFORMATION: Synthetic DNA

<400> SEQUENCE: 30

```
ccttctgtag tttggttgcc                                                20
```

<210> SEQ ID NO 31
<211> LENGTH: 467
<212> TYPE: DNA
<213> ORGANISM: non-B, non-C, non-G hepatitis virus

<400> SEQUENCE: 31

```
ccatgcctcc ttttctagac acagaactca cagcccctag catacaccca ggcatgctag    60
ccctagacaa aagagcaaga tggatacctag gcttaaaatc tagaccggga aaaaaacact   120
atattaaaat aagagtaggg gcaccaaaaa tgttcactga taaatggtac ccccaaacag   180
atctttgtga catggtgctt ctaactgtct atgcaaccgc agcggatatg caatatccgt   240
tcggctcacc actaactgac tctgtggttg tgaacttcca ggttctgcaa tccatgtatg   300
ataaaacaat tagcatatta ccagacgaaa aagaagaaag agcaaatcta cttaagcaga   360
taacaagtta cattcccttt tataatacca cacaaactat agcccaatta aagccattta   420
tagatgcagg caatgtaaca tcaagcacaa cagcaacaac atgggca                 467
```

<210> SEQ ID NO 32
<211> LENGTH: 748

```
<212> TYPE: DNA
<213> ORGANISM: non-B, non-C, non-G hepatitis virus

<400> SEQUENCE: 32
tcactaacca cgtgacaccc acaggccaac cgaatgctat gtcatccatt tcctgggccg    60
ggtctacgtc ctcatataag taagtgcact tccgaatggc tgagttttcc acgcccgtcc   120
gcagcggtga agccacggag ggagatctcc gcgtcccgag ggcgggtgcc gaaggtgagt   180
ttacacaccg aagtcaaggg gcaattcggg ctcgggactg gccgggctat gggcaaggct   240
ctgaaaaaag catgtttatt ggcaggcatt acagaaagaa aagggcgctg tcactgtgtg   300
ctgtgcgaac aacaaagaag gcttgcaaac tactaatagt aatgtggacc ccacctcgca   360
atgatcaaca ctaccttaac tggcaatggt actcaagtat acttagctcc cacgctgcta   420
tgtgcgggtg tcccgacgct gtcgctcatt ttaatcatct tgcttctgtg cttcgtgccc   480
cgcaaaaccc accccctccc ggtccccagc gaaacctgcc cctccgacgg ctgccggctc   540
tcccggctgc gccagaggcg cccggagata gagcaccatg gcctatggct ggtggcgccg   600
aaggagaaga cggtggcgca ggtggagacg cagaccatgg aggcgccgct ggaggacccg   660
aagacgcaga cctgctagac gccgtggccg ccgcagaaac gtaaggagac gccgcagagg   720
agggaggtgg aggaggagat ataggaga                                      748

<210> SEQ ID NO 33
<211> LENGTH: 197
<212> TYPE: DNA
<213> ORGANISM: non-B, non-C, non-G hepatitis virus

<400> SEQUENCE: 33
aaagtaacta agcactccga gcgaagcgag gagtgcgacc cttgggggct caacgccttc    60
ggagccgcgc gctacgcctt cggctgcgcg cggcacctca gaccccgct cgtgctgaca    120
cgctcgcgcg tgtcagacca cttcgggctc gcggggtcg ggaaatttac taaacagact   180
ccgagttgcc attggac                                                  197

<210> SEQ ID NO 34
<211> LENGTH: 20
<212> TYPE: DNA
<213> ORGANISM: Artificial Sequence
<220> FEATURE:
<223> OTHER INFORMATION: Synthetic DNA

<400> SEQUENCE: 34
tgcccatgtt gttgctgttg                                                20

<210> SEQ ID NO 35
<211> LENGTH: 20
<212> TYPE: DNA
<213> ORGANISM: Artificial Sequence
<220> FEATURE:
<223> OTHER INFORMATION: Synthetic DNA

<400> SEQUENCE: 35
ccatgcctcc ttttctagac                                                20

<210> SEQ ID NO 36
<211> LENGTH: 20
<212> TYPE: DNA
<213> ORGANISM: Artificial Sequence
<220> FEATURE:
<223> OTHER INFORMATION: Synthetic DNA
```

```
<400> SEQUENCE: 36
tctcctatat ctcctcctcc                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic DNA

<400> SEQUENCE: 37
tcactaacca cgtgacaccc                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic DNA

<400> SEQUENCE: 38
aaagtaacta agcactccga                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic DNA

<400> SEQUENCE: 39
gtccaatggc aactcggagt                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic DNA

<400> SEQUENCE: 40
caccaggagc atatacagac                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic DNA

<400> SEQUENCE: 41
caaggtatgt tgcccgtttg                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic DNA

<400> SEQUENCE: 42
cgaaccacgt aacaaatggc                                               20

<210> SEQ ID NO 43
<211> LENGTH: 20
```

<212> TYPE: DNA
<213> ORGANISM: Artificial Sequence
<220> FEATURE:
<223> OTHER INFORMATION: Synthetic DNA

<400> SEQUENCE: 43
tgttgcccgt ttgtcctcta 20

<210> SEQ ID NO 44
<211> LENGTH: 20
<212> TYPE: DNA
<213> ORGANISM: Artificial Sequence
<220> FEATURE:
<223> OTHER INFORMATION: Synthetic DNA

<400> SEQUENCE: 44
ggcactagta aactgagcca 20

<210> SEQ ID NO 45
<211> LENGTH: 222
<212> TYPE: DNA
<213> ORGANISM: non-B, non-C, non-G hepatitis virus

<400> SEQUENCE: 45
ctaagyaaaa aaaacatgaa vtatgacaaa strcaaagta artgcytart akcagaccta 60
ccwctrtggg cagcagcata tggwtatgta gaattytgyg cwaaaagyac aggagacvva 120
aacagacaca tgaatgccag rctactaata agaagtccyt ttacagaccc vcarctavta 180
gtacacacag accccacwaa aggctttgtw ccytaytctk ta 222

<210> SEQ ID NO 46
<211> LENGTH: 222
<212> TYPE: DNA
<213> ORGANISM: non-B, non-C, non-G hepatitis virus

<400> SEQUENCE: 46
ctaacyaaar atrvctcasw rtaydvvaar vvacaragya aatgtctvat asvdracwtg 60
ccyytrtgrg cctcwgtrta yggatwywcv gaatactgca gyaaagtwac aggagacwca 120
aacagagarc acaactgyag atgtgthaty agaagcccct ayacagtrcc wcarctgyta 180
gaycacaaca ayvscctyag rggwtaygtd ccvtayagya th 222

<210> SEQ ID NO 47
<211> LENGTH: 222
<212> TYPE: DNA
<213> ORGANISM: non-B, non-C, non-G hepatitis virus

<400> SEQUENCE: 47
ctagtaaaga cagactctag atatgacaag acacgcagca aatgccttat agaaaaacta 60
ccyctatggg cttcagtata cggktacgca gartactgcg ccaaggccac aggagactct 120
aacagagaca tgaacgccag agtagttata aggagcccct acactacacc tcaaatgata 180
gaycacaaca ayvscctcag rggwtaygtd ccvtayagyt th 222

<210> SEQ ID NO 48
<211> LENGTH: 222
<212> TYPE: DNA
<213> ORGANISM: non-B, non-C, non-G hepatitis virus

<400> SEQUENCE: 48
ctatcaaaat cagacgccct ttacaccaaa ggacaaagca aatgtgaaat atttgactta 60

```
cccctctggg ccgccctaaa tggctacaca gaattctgct ccaaaagcac aggagacaca      120
gcaggacacc taaatgccag actagtgata agatgcccat acacataccc catgctagta      180
gaccactcaa acgacctaac aggctttgta ctgtacagca aa                        222
```

<210> SEQ ID NO 49
<211> LENGTH: 222
<212> TYPE: DNA
<213> ORGANISM: non-B, non-C, non-G hepatitis virus

<400> SEQUENCE: 49

```
ctaagcaaat cagatgcagt atactctgaa aaacaaagca aatgtgctat atttgaccta      60
ccactatggg cctccttctt tggatacgca gaattctgct ctaaaagcac aggagacaca     120
gccagagcat acaacgccag agtatgtgtt agatgtccct acacagagcc acagctgcta    180
aaccacaaca acccctctca ggggttcgtg ttttactcct ac                       222
```

<210> SEQ ID NO 50
<211> LENGTH: 222
<212> TYPE: DNA
<213> ORGANISM: non-B, non-C, non-G hepatitis virus

<400> SEQUENCE: 50

```
ctgagcaaac cagacagcat atacgacccc tctaagagca aatgcctact aaaagacttt     60
cccctgtggt gcatggtata cgggtacgca gactactgca gaaaggtcac aggagactca   120
gccagactac tagactgcag agtatgtgtt agatgcccgt acacataccc tcagcttata    180
aaacacaaca atgacaactg gggctttgtc ccctatagcg aa                       222
```

<210> SEQ ID NO 51
<211> LENGTH: 222
<212> TYPE: DNA
<213> ORGANISM: non-B, non-C, non-G hepatitis virus

<400> SEQUENCE: 51

```
tgtcttaaaa acgataccac gttcaaagac acaccatcca gactaccgt aaaagacata      60 cccctatggg cctgtttcat gggataccag gactactgct cgaaacactt tcatgacgaa   120
ggcagaaaca aagaggccag agtcacaata atatccccat acacagaacc accactgacc    180
tcgaaagaca accactcaat gggattcata ccatatgact at                      222
```

<210> SEQ ID NO 52
<211> LENGTH: 222
<212> TYPE: DNA
<213> ORGANISM: non-B, non-C, non-G hepatitis virus

<400> SEQUENCE: 52

```
tgcactaaaa atgacacaca attcagagat gtccccggca gactcaccat atcagacgtc     60
cccctgtacg cggccctcct gggctacgag gactactgta tcaaatacta ccacgacaaa   120
ggcctaccta agaagtcag ggtcaccata cagtgtccat acacagatcc ccccctctat    180
gacaaagaca acacagacat gggctaccta ccttatgact ac                      222
```

<210> SEQ ID NO 53
<211> LENGTH: 225
<212> TYPE: DNA
<213> ORGANISM: non-B, non-C, non-G hepatitis virus

<400> SEQUENCE: 53

```
ctcacwaaac caracacasa gtttgaccck gtacagtgca aatgygtmwt astagacatw     60
```

```
ccmytgtggg ccgccttytt yggctaccca gactacatag aragccarct aggcccytty      120
cargaycacg aractgtkgg catagtgttc gtgtgytgcc cctacactca rccrcccatg      180
tacaarccwg gcarvrtaca aamtggctay gttttctatg acact                     225

<210> SEQ ID NO 54
<211> LENGTH: 225
<212> TYPE: DNA
<213> ORGANISM: non-B, non-C, non-G hepatitis virus

<400> SEQUENCE: 54
cacagcaaag taaacacaga cctcagagac agaggcatct actgcctact agaagacatg       60
cccctgtggg ccatgacctt tggatacagt gactatgtga gcacacaact aggcccaaac      120
gtggaccacg agactcaagg cctggtatgc agatctagtc cttacactga gccccccatg      180
tatgacaaga ctaacccaaa cagtggctac gtagcatatg acaca                     225

<210> SEQ ID NO 55
<211> LENGTH: 23
<212> TYPE: DNA
<213> ORGANISM: Artificial Sequence
<220> FEATURE:
<223> OTHER INFORMATION: Synthetic DNA

<400> SEQUENCE: 55
tggtggcgcc gaaggagaag acg                                              23

<210> SEQ ID NO 56
<211> LENGTH: 20
<212> TYPE: DNA
<213> ORGANISM: Artificial Sequence
<220> FEATURE:
<223> OTHER INFORMATION: Synthetic DNA

<400> SEQUENCE: 56
gctcttatgt acctcctgcg                                                  20

<210> SEQ ID NO 57
<211> LENGTH: 20
<212> TYPE: DNA
<213> ORGANISM: Artificial Sequence
<220> FEATURE:
<223> OTHER INFORMATION: Synthetic DNA

<400> SEQUENCE: 57
tttgctacgt cactaaccac                                                  20

<210> SEQ ID NO 58
<211> LENGTH: 20
<212> TYPE: DNA
<213> ORGANISM: Artificial Sequence
<220> FEATURE:
<223> OTHER INFORMATION: Synthetic DNA

<400> SEQUENCE: 58
gtagaccatg aaacagcagg                                                  20

<210> SEQ ID NO 59
<211> LENGTH: 20
<212> TYPE: DNA
<213> ORGANISM: Artificial Sequence
<220> FEATURE:
<223> OTHER INFORMATION: Synthetic DNA
```

```
<400> SEQUENCE: 59
tcaaccacct atgtatgaca                                                20

<210> SEQ ID NO 60
<211> LENGTH: 27
<212> TYPE: DNA
<213> ORGANISM: Artificial Sequence
<220> FEATURE:
<223> OTHER INFORMATION: Synthetic DNA

<400> SEQUENCE: 60
gccgacggtt ttttggcgcc tttttc                                         27

<210> SEQ ID NO 61
<211> LENGTH: 20
<212> TYPE: DNA
<213> ORGANISM: Artificial Sequence
<220> FEATURE:
<223> OTHER INFORMATION: Synthetic DNA

<400> SEQUENCE: 61
aaagaggaag gaagtcagcc                                                20

<210> SEQ ID NO 62
<211> LENGTH: 3722
<212> TYPE: DNA
<213> ORGANISM: non-B, non-C, non-G hepatitis virus
<220> FEATURE:
<221> NAME/KEY: CDS
<222> LOCATION: 590..2872
<220> FEATURE:
<221> NAME/KEY: CDS
<222> LOCATION: 258..725

<400> SEQUENCE: 62
tttgctacgt cactaaccac gtgactcccg caggccaacc cagtactatg tcgtccactt      60
cctgggacga gtctacgtcc tgatataagt aagtgcactt ccgaatggct gagttttcca    120
cgcccgtccg cagcgagaac gccacggagg ggagtccgcg cgtcccgagg gcgggtgccg    180
gaggtgagtt tacacaccgc agtcaagggg caattcgggc tcgggactgg ccgggccccg    240
ggcaaggctc ttaaaaaatg cactttcgca gagtgcgagc gaaaaggaaa ctgctactgc    300
aagctgtgcg agctccaccg aaggcacctg ccatgagctt caccacacct actattaatg    360
ccgggatccg agagcagcaa tggttcgagt ccacccttag atcccaccac tcgttctgtg    420
gctgtggtga tcccgtgctt cattttacta accttgctac tcgctttaac tatctgcctg    480
ctacctcttc gcctctggac cctcccggcc cagcgccgcg aggccgcccg gcgctccgcc    540
gcctcccggc actcccttca gccccgcgca ccccttctag agaactagca tggcctactg    600
gttcagaagg tggggctgga ggccgaggcg ccggtggaga aggtggcgcc gccgtcgaag    660
gagactaccg agaagaagaa ctagacgagc tgttcgcggc cttggaagaa gacgcaaacc    720
aagggtaagg aggcgccgca gaactcgcag acgtacctac agacgggggt ggagacgcag    780
gaggtacata agacggggc gacgcaaaaa gaaactcata ctgactcagt ggaacccggc    840
aatagttaag aggtgcaaca ttaagggcgg acttccaata attatatgcg gagagcccag    900
ggcagccttt aactatggct accacatgga ggactacact cctcaacctt tccccttcgg    960
agggggaatg agcacagtga ctttctctct gaaagccttg tatgaccagt acctaaaaca   1020
ccaaaacagg tggactttct caaacgacca gctagacctc gccagataca ggggctgtaa   1080
actaaggttc tacagaagcc ccgtctgtga ctttatagta cactacaacc taatacctcc   1140
```

-continued

```
actaaaaatg aaccagttca caagtcccaa cacgcacccg ggactactca tgctcagcaa    1200
acacaagata ataattccca gctttcaaac aagacctggg ggcagacgct ttgttaaaat    1260
aagacttaat cccccaaac tatttgaaga caagtggtac actcagcaag acctgtgcaa     1320
ggttccgctc gttagtatta cagcaactgc ggctgacttg cggtatccgt tctgctcacc    1380
acaaacgaac aacccttgca ccaccttcca ggtactgcgc aagaactaca atacagttat    1440
aggaacttcc gtaaaagacc aagagtccac acaagacttt gaaaattggc tttataaaac    1500
agactcacac tatcaaacat ttgccacaga ggctcaacta gcagaattc ctgcatttaa     1560 tcctgatggc actaaaaaca ctaaacagca gtcgtggcaa gataactgga gcaaaaaaaa    1620
ttcaccatgg acaggtaact caggtacata cccacaaaca accagtgaaa tgtacaaaat    1680
tccatatgac agtaacttcg gctttcccac atacagagcc caaaaagact acattttaga    1740
aagaagacag tgcaactttta actatgaagt taataatcca gttagcaaaa agtatggcc    1800 acaacctagt acaacaacac ccacagtaga ctactatgaa taccactgtg gatggttcag    1860
caacatattc ataggcccca acagatacaa cctacagttt caaacagcat atgtagacac    1920
cacatacaac ccactaatgg acaagggcaa aggcaacaaa atatggtttc aatatctgtc    1980 taaaagggc acagactaca atgaaaaaca atgctactgc acccctagaag acatgcccct    2040 atgggcaata tgctttggat acactgacta tgtagagact caactaggac ccaatgtgga    2100
ccatgaaaca gcaggcttaa taattatgat ctgtccatac actcaaccac ctatgtatga    2160 caaaacaga cctaactggg gatacgtagt ctatgacaca aactttggca atggaaaaat    2220
gccctcagga agtggccaag tcccagtata ctgcaatgc cgatggaggc ccatgctgtg    2280
gttccaacaa caagtactca atgacatctc aaagactgga ccgtacgcct acagagacga    2340
atataaaaat gtacaactga ctctctacta caacttttatt tttaactggg gggcgacat     2400 gtattaccca caggtcgtta aaaacccctg tggagactcc ggaatcgttc ccggttccgg    2460
tagattcact cgagaagtac aagtcgttag cccgctttcc atgggaccgg cctacatctt    2520
ccactacttc gactccagac gcgggttctt tagtgaaaaa gctcttaaaa gaatgcaaca    2580
acaacaagaa tttgatgaat ctttacatt caaacctaag agacccaaac tttctacagc    2640
agccgcagaa atcctccagc tcgaagaaga ctcgacttca ggggaaggaa aatcgccact    2700
acagcaagaa gagaaagaag tcgaagtcct ccaaacgccg acagtacagc tccagctcca    2760
gcgaaacatc caggagcagc tcgcaatcaa gcagcagctc caattcctct tgctccaact    2820
cctcaaaacc caatccaatt tgcatttaaa cccacaattt ttaagcccttt cataaaatat    2880 gacatgtttg gggacccct tcctcacccc ccaacagccg aagagtggga aacagagtac    2940
cagtgctgta aggcctttaa cagaccacct agaaccaacc taaaagacac cccttctac     3000 ccctgggtac ctaaacctaa acctcaattc cgtgtatctt ttaaacttgg ttttcaataa    3060
acaaggccgt gggagtttca cttgtcggtg tcaacctctt aaggtcacta agcactccga    3120
gcgtaagcga ggagtgcgac cctcccccct ggggcaactc cctcgaagtc cggcgctacg    3180
cgcttcgcgc tgcgccggac atctcggacc ccccctccac ccgaaacgct tgcgcgtttc    3240
ggaccttcgg cgtcgggggg gtcgggggct ttactaaaca gactccgagg tgccattgga    3300
cactgagggg atgaacagca acgaaagtga gtggggccag acttcgccat aaggccttta    3360
tcttcttgcc atttgtcagt atagagggtc gccataggct tcggcctcca ttttaacctc    3420
taaaaactac caaaatggcc gttccagtga cgtcacagcc gccatttttaa gtagctgacg    3480
```

-continued tcaaggattg acgtgaaggt taaaggtcat cctcggcgga agctacacaa aatggtggac 3540
aacatcttcc gggtcaaagg tcgtgcacac gtcataagtc acgtggtggg gacccgctgt 3600
aacccggaag taggccccgt cacgtgattt gtcacgtgtg tacacgtcac aaccgccatt 3660
ttgttttaca aaatggctga cttccttcct ctttttgaaa aaaggcgcca aaaaaccgtc 3720
gg 3722

<210> SEQ ID NO 63
<211> LENGTH: 761
<212> TYPE: PRT
<213> ORGANISM: non-B, non-C, non-G hepatitis virus

<400> SEQUENCE: 63

Met Ala Tyr Trp Phe Arg Arg Trp Gly Trp Arg Pro Arg Arg Arg
1 5 10 15

Trp Arg Arg Trp Arg Arg Arg Arg Arg Arg Leu Pro Arg Arg Arg
20 25 30

Thr Arg Arg Ala Val Arg Gly Leu Gly Arg Arg Arg Lys Pro Arg
35 40 45

Val Arg Arg Arg Arg Arg Thr Arg Arg Arg Thr Tyr Arg Arg Gly
50 55 60

Trp Arg Arg Arg Arg Tyr Ile Arg Arg Gly Arg Arg Lys Lys Lys
65 70 75

Leu Ile Leu Thr Gln Trp Asn Pro Ala Ile Val Lys Arg Cys Asn
80 85 90

Ile Lys Gly Gly Leu Pro Ile Ile Ile Cys Gly Glu Pro Arg Ala
95 100 105

Ala Phe Asn Tyr Gly Tyr His Met Glu Asp Tyr Thr Pro Gln Pro
110 115 120

Phe Pro Phe Gly Gly Gly Met Ser Thr Val Thr Phe Ser Leu Lys
125 130 135

Ala Leu Tyr Asp Gln Tyr Leu Lys His Gln Asn Arg Trp Thr Phe
140 145 150

Ser Asn Asp Gln Leu Asp Leu Ala Arg Tyr Arg Gly Cys Lys Leu
155 160 165

Arg Phe Tyr Arg Ser Pro Val Cys Asp Phe Ile Val His Tyr Asn
170 175 180

Leu Ile Pro Pro Leu Lys Met Asn Gln Phe Thr Ser Pro Asn Thr
185 190 195

His Pro Gly Leu Leu Met Leu Ser Lys His Lys Ile Ile Ile Pro
200 205 210

Ser Phe Gln Thr Arg Pro Gly Gly Arg Arg Phe Val Lys Ile Arg
215 220 225

Leu Asn Pro Pro Lys Leu Phe Glu Asp Lys Trp Tyr Thr Gln Gln
230 235 240

Asp Leu Cys Lys Val Pro Leu Val Ser Ile Thr Ala Thr Ala Ala
245 250 255

Asp Leu Arg Tyr Pro Phe Cys Ser Pro Gln Thr Asn Asn Pro Cys
260 265 270

Thr Thr Phe Gln Val Leu Arg Lys Asn Tyr Asn Thr Val Ile Gly
275 280 285

Thr Ser Val Lys Asp Gln Glu Ser Thr Gln Asp Phe Glu Asn Trp
290 295 300

Leu Tyr Lys Thr Asp Ser His Tyr Gln Thr Phe Ala Thr Glu Ala

```
                    305                 310                 315
Gln Leu Gly Arg Ile Pro Ala Phe Asn Pro Asp Gly Thr Lys Asn
                    320                 325                 330
Thr Lys Gln Gln Ser Trp Gln Asp Asn Trp Ser Lys Lys Asn Ser
                    335                 340                 345
Pro Trp Thr Gly Asn Ser Gly Thr Tyr Pro Gln Thr Thr Ser Glu
                    350                 355                 360
Met Tyr Lys Ile Pro Tyr Asp Ser Asn Phe Gly Phe Pro Thr Tyr
                    365                 370                 375
Arg Ala Gln Lys Asp Tyr Ile Leu Glu Arg Arg Gln Cys Asn Phe
                    380                 385                 390
Asn Tyr Glu Val Asn Asn Pro Val Ser Lys Lys Val Trp Pro Gln
                    395                 400                 405
Pro Ser Thr Thr Thr Pro Thr Val Asp Tyr Tyr Glu Tyr His Cys
                    410                 415                 420
Gly Trp Phe Ser Asn Ile Phe Ile Gly Pro Asn Arg Tyr Asn Leu
                    425                 430                 435
Gln Phe Gln Thr Ala Tyr Val Asp Thr Thr Tyr Asn Pro Leu Met
                    440                 445                 450
Asp Lys Gly Lys Gly Asn Lys Ile Trp Phe Gln Tyr Leu Ser Lys
                    455                 460                 465
Lys Gly Thr Asp Tyr Asn Glu Lys Gln Cys Tyr Cys Thr Leu Glu
                    470                 475                 480
Asp Met Pro Leu Trp Ala Ile Cys Phe Gly Tyr Thr Asp Tyr Val
                    485                 490                 495
Glu Thr Gln Leu Gly Pro Asn Val Asp His Glu Thr Ala Gly Leu
                    500                 505                 510
Ile Ile Met Ile Cys Pro Tyr Thr Gln Pro Pro Met Tyr Asp Lys
                    515                 520                 525
Asn Arg Pro Asn Trp Gly Tyr Val Val Tyr Asp Thr Asn Phe Gly
                    530                 535                 540
Asn Gly Lys Met Pro Ser Gly Ser Gly Gln Val Pro Val Tyr Trp
                    545                 550                 555
Gln Cys Arg Trp Arg Pro Met Leu Trp Phe Gln Gln Gln Val Leu
                    560                 565                 570
Asn Asp Ile Ser Lys Thr Gly Pro Tyr Ala Tyr Arg Asp Glu Tyr
                    575                 580                 585
Lys Asn Val Gln Leu Thr Leu Tyr Tyr Asn Phe Ile Phe Asn Trp
                    590                 595                 600
Gly Gly Asp Met Tyr Tyr Pro Gln Val Val Lys Asn Pro Cys Gly
                    605                 610                 615
Asp Ser Gly Ile Val Pro Gly Ser Gly Arg Phe Thr Arg Glu Val
                    620                 625                 630
Gln Val Val Ser Pro Leu Ser Met Gly Pro Ala Tyr Ile Phe His
                    635                 640                 645
Tyr Phe Asp Ser Arg Arg Gly Phe Phe Ser Glu Lys Ala Leu Lys
                    650                 655                 660
Arg Met Gln Gln Gln Glu Phe Asp Glu Ser Phe Thr Phe Lys
                    665                 670                 675
Pro Lys Arg Pro Lys Leu Ser Thr Ala Ala Ala Glu Ile Leu Gln
                    680                 685                 690
Leu Glu Glu Asp Ser Thr Ser Gly Glu Gly Lys Ser Pro Leu Gln
                    695                 700                 705
```

-continued

```
Gln Glu Glu Lys Glu Val Glu Val Leu Gln Thr Pro Thr Val Gln
                710                 715                 720

Leu Gln Leu Gln Arg Asn Ile Gln Glu Gln Leu Ala Ile Lys Gln
                725                 730                 735

Gln Leu Gln Phe Leu Leu Leu Gln Leu Leu Lys Thr Gln Ser Asn
                740                 745                 750

Leu His Leu Asn Pro Gln Phe Leu Ser Pro Ser
                755                 760

<210> SEQ ID NO 64
<211> LENGTH: 156
<212> TYPE: PRT
<213> ORGANISM: non-B, non-C, non-G hepatitis virus

<400> SEQUENCE: 64

Met His Phe Arg Arg Val Arg Ala Lys Arg Lys Leu Leu Leu Gln
 1               5                  10                  15

Ala Val Arg Ala Pro Pro Lys Ala Pro Ala Met Ser Phe Thr Thr
                20                  25                  30

Pro Thr Ile Asn Ala Gly Ile Arg Glu Gln Gln Trp Phe Glu Ser
                35                  40                  45

Thr Leu Arg Ser His His Ser Phe Cys Gly Cys Gly Asp Pro Val
                50                  55                  60

Leu His Phe Thr Asn Leu Ala Thr Arg Phe Asn Tyr Leu Pro Ala
                65                  70                  75

Thr Ser Ser Pro Leu Asp Pro Pro Gly Pro Ala Pro Arg Gly Arg
                80                  85                  90

Pro Ala Leu Arg Arg Leu Pro Ala Leu Pro Ser Ala Pro Ala Thr
                95                  100                 105

Pro Ser Arg Glu Leu Ala Trp Pro Thr Gly Ser Glu Gly Gly Ala
                110                 115                 120

Gly Gly Arg Gly Ala Gly Gly Glu Gly Gly Ala Ala Val Glu Gly
                125                 130                 135

Asp Tyr Arg Glu Glu Leu Asp Glu Leu Phe Ala Ala Leu Glu
                140                 145                 150

Glu Asp Ala Asn Gln Gly
                155
```

NON-B, NON-C, NON-G HEPATITIS VIRUS GENE, POLYNUCLEOTIDE, POLYPEPTIDE, VIRUS PARTICLE, METHOD FOR ISOLATING VIRUS PARTICLE, AND METHOD FOR DETECTING VIRUS

This is a continuation of U.S. Ser. No. 09/463,488, filed May 1, 2000, now abandoned which is the U.S. National Phase under 35 U.S.C. § 371 of International Application PCT/JP98/03340, filed Jul. 27, 1998, which claims priority of JP 10-82962, filed Mar. 13, 1998; JP 9-314196, filed Oct. 9, 1997; and JP 9-233246, filed Jul. 25, 1997. Each of the above applications are incorporated herein by reference in their entirety.

TECHNICAL FIELD

The present invention relates to a gene, a polynucleotide, a polypeptide, an antibody, and an antigen, which have become available by discovery of an etiologic virus of blood-borne infectious hepatitis whose etiology could not be identified by conventional diagnostic methods, as well as methods for production, detection and assay of a virus gene, an antibody and an antigen, by utilizing the gene, the polynucleotide, the polypeptide, the antibody and the antigen which have been available, a virus particle and method for isolation of the virus particle.

BACKGROUND ART

Hepatitis B virus (abbreviated as "HBV" hereinafter) and hepatitis C virus (abbreviated as "HCV" hereinafter) have been discovered so far as etiologic viruses of blood-borne infectious hepatitis. Diagnostic methods for the both viruses have already been established, and they were early introduced into the screening of blood for blood transfusion in this country. As a result, it has become possible to substantially completely prevent novel infection cases in blood recipients for the both hepatitis viruses.

However, even after the diagnostic methods for HBV and HCV were established, cases suspected of cryptogenic viral hepatitis constitute 5–10% of the whole hepatitis cases. These cases have not been considered to be caused by hepatitis A virus, which is a hepatitis virus of non-blood-borne infectious type, hepatitis E virus, hepatitis F virus, which has been reported only in India and its existence itself is doubted, and hepatitis D virus, which is a defective hepatitis virus, and possible existence of unknown hepatitis virus has been suggested.

Gene sequences of viruses considered to be etiologic agents of these hepatitis cases were reported in succession by Abbott, U.S.A. in 1995, and then by Genelabs Technologies in 1996, and designated as GBV-C and HGV, respectively. However, these viruses became to be considered identical one afterwards based on comparison of their sequences (abbreviated as "GBV-C/HGV" hereinafter). Studies about involvement of GBV-C/HGV in cryptogenic viral hepatitis are being actively performed also in this country. As a result, it has thus far considered at least that GBV-C/HGV does not account for all of the causes of non-B, non-C hepatitis of unknown etiology, because expression of hepatitis symptoms has been slight in its infection cases while it may be transmitted via hematic route, and therefore an unknown virus might be responsible for the cryptogenic hepatitis.

Existence of an unknown hepatitis virus causing blood-borne infectious hepatitis has been suggested as described above, and it has been desired to discover this unknown hepatitis virus, and elucidate genetic, molecular-biological and epidemiological characteristics of the virus, thereby realizing more complete prophylactics, diagnostic methods and therapies for hepatitis.

In other words, in order to develop diagnostic methods and therapeutic methods of hepatitis caused by an unidentified virus, desired are to obtain genetic information of the virus, to determine virus-specific gene sequences and amino acid sequences, to determine locations of epitopes, to establish production methods of biological materials containing the epitopes, to establish production methods of antigens which specifically react with antiviral antibodies, to provide specific antibodies for the virus, to establish methods for isolating and collecting virus particles, to establish methods for treating the virus particles to attenuate their biological activity while maintaining their immunological activity, and to develop methods for assaying genes, antibodies, and antigens, and methods for producing neutralizing antibody-derived vaccines, which utilize the aforementioned biological materials derived from the virus to be obtained.

DISCLOSURE OF THE INVENTION

An object of the present invention is to newly establish a diagnostic method and a treatment method of unidentified viral hepatitis whose etiologic virus has not been identified so far and therefore for which means for diagnosis, prevention and treatment have not been developed.

Another object of the present invention is to isolate an unidentified novel hepatitis virus gene to determine its gene sequence, thereby providing genes, polynucleotides, polypeptides, methods for isolating virus particles, virus particles, viral antigens, and antiviral antibodies, which can be utilized for diagnosis and treatment, and methods for detecting the virus.

The present inventors assumed that, in blood of patients suffering hepatitis of which cause cannot be identified by conventional diagnostic methods of viral hepatitis, unknown hepatitis virus particles or a part thereof should be present. Based on this assumption, the present inventors attempted to isolate a viral gene from such blood. Specifically, the present inventors established a hypothesis that the viral gene would exist in blood of hepatitis patients, but does not exist in human genome and does not exist in blood of most of normal persons, or it does not exist before crisis of hepatitis, but exist after the crisis, searched for candidate genes in blood of hepatitis patients based on the hypothesis, and isolated them. Further, the candidate genes were examined for the following criteria, and a gene satisfying all of the criteria was ultimately considered as a novel viral genes:

(1) the gene exists in blood of a plurality of patients of hepatitis of which cause has not been elucidated,
(2) there are cases that blood transfusion recipients have become positive for the gene due to transfusion with blood positive for the gene while the gene has not existed in their blood before the blood transfusion, and crisis of hepatitis has been observed in them after the blood transfusion,
(3) the obtained gene sequence is not homologous to gene sequences of known hepatitis viruses or other known viruses, and
(4) when blood positive for the gene is analyzed by a density gradient centrifugation technique, which is widely used as a method for isolating and collecting virus particles, a fraction positive for the gene is found in a usual virus particle fraction.

Asymptomatic carriers, i.e., infection cases which are positive for a hepatitis virus but do not exhibit symptoms of hepatitis and appear healthy, are known for infection cases of known hepatitis viruses, and it was considered that such cases would be well possible for the infection cases of the virus of interest. Therefore, the criteria do not contain a criterion that "the genes do not found in normal persons."

According to the aforementioned criteria, the gene of the present invention was isolated, a sequence of the isolated gene was determined, and oligonucleotide sequences which could be utilized as PCR primers were searched.

By utilizing the obtained primers, a method for detecting the gene was established. Further, open reading frames existing in the gene sequence was identified, and amino acid sequences were specified. Density was also determined by density gradient centrifugation, and a method for collecting the virus was established. Thus, the present invention has been completed.

That is, the present invention provides non-B, non-C, non-G hepatitis virus gene having a nucleotide sequence from which a sequence having a length of from about 3500 nucleotides to about 4000 nucleotides can be amplified by PCR utilizing an oligonucleotide having the nucleotide sequence shown in SEQ ID NO: 57 and an oligonucleotide having the nucleotide sequence shown in SEQ ID NO: 60 as primers, or PCR utilizing an oligonucleotide having the nucleotide sequence shown in SEQ ID NO: 57 and an oligonucleotide having the nucleotide sequence shown in SEQ ID NO: 61 as primers (also referred to as the gene of the present invention hereinafter).

The gene of the present invention preferably has a nucleotide sequence from which a sequence having a length of from about 3600 nucleotides to 3900 nucleotides can be amplified by the PCR.

Preferably, for the gene of the present invention, nucleotide sequences at 5' end and 3' end of the fragments amplified by the PCR respectively have 70% or more of homology to the nucleotide sequences of nucleotide number 3–300 and the nucleotide sequence of nucleotide number 2402–3739 of the nucleotide sequence shown in SEQ ID NO: 1. More preferably, the homology is 80% or more.

The present invention further provides non-B, non-C, non-G hepatitis virus gene of the following (a) or (b):

(a) a non-B, non-C, non-G hepatitis virus gene having a nucleotide sequence from which a sequence having a length of from about 200 nucleotides to about 350 nucleotides can be amplified by PCR utilizing an oligonucleotide having the nucleotide sequence shown in SEQ ID NO: 6 and an oligonucleotide having the nucleotide sequence shown in SEQ ID NO: 8 as primers, or (b) a non-B, non-C, non-G hepatitis virus gene having a nucleotide sequence from which a sequence having a length of from about 200 nucleotides to about 350 nucleotides can be amplified by PCR utilizing an oligonucleotide having the nucleotide sequence shown in SEQ ID NO: 7 and an oligonucleotide having the nucleotide sequence shown in SEQ ID NO: 8 as primers.

The gene of the present invention is preferably a non-B, non-C, non-G hepatitis virus gene having the nucleotide sequence shown in SEQ ID NO: 1 or an allogeneic variant gene thereof. Examples of the gene include, for example, a non-B, non-C, non-G hepatitis virus gene having the nucleotide sequence shown in SEQ ID NO: 45 (Genotype 1), a non-B, non-C, non-G hepatitis virus gene having the nucleotide sequence shown in SEQ ID NO: 46 (Genotype 2), a non-B, non-C, non-G hepatitis virus gene having the nucleotide sequence shown in SEQ ID NO: 47 (Genotype 3), a non-B, non-C, non-G hepatitis virus gene having the nucleotide sequence shown in SEQ ID NO: 48 (Genotype 4), a non-B, non-C, non-G hepatitis virus gene having the nucleotide sequence shown in SEQ ID NO: 49 (Genotype 5), a non-B, non-C, non-G hepatitis virus gene having the nucleotide sequence shown in SEQ ID NO: 50 (Genotype 6), a non-B, non-C, non-G hepatitis virus gene having the nucleotide sequence shown in SEQ ID NO: 51 (Genotype 7), a non-B, non-C, non-G hepatitis virus gene having the nucleotide sequence shown in SEQ ID NO: 52 (Genotype 8), a non-B, non-C, non-G hepatitis virus gene having the nucleotide sequence shown in SEQ ID NO: 53 (Genotype 9), and a non-B, non-C, non-G hepatitis virus gene having the nucleotide sequence shown in SEQ ID NO: 54 (genotype 10).

The present invention also provides a polynucleotide having a nucleotide sequence complementary to a nucleotide sequence of the gene of the present invention.

The present invention also provides an oligonucleotide comprising a nucleotide sequence recognized in the genes of the present invention and specific for the genes or a nucleotide sequence complementary thereto (also referred to the oligonucleotide of the present invention hereinafter). Specific examples of the oligonucleotide include, for example, a polynucleotide having the nucleotide sequence shown in SEQ ID NO: 2 (RD037), a polynucleotide having the nucleotide sequence shown in SEQ ID NO: 3 (RD038), a polynucleotide having the nucleotide sequence shown in SEQ ID NO: 4 (RD051), a polynucleotide having the nucleotide sequence shown in SEQ ID NO: 5 (RD052), a polynucleotide having the nucleotide sequence shown in SEQ ID NO: 6 (NG059), a polynucleotide having the nucleotide sequence shown in SEQ ID NO: 7 (NG061), and a polynucleotide having the nucleotide sequence shown in SEQ ID NO: 8 (NG063).

The present invention also provides a method for detecting a non-B, non-C, non-G hepatitis virus gene wherein PCR is performed by using the oligonucleotides of the present invention as primers.

Specific examples of the detection method include, for example, a method for detecting a non-B, non-C, non-G hepatitis virus gene wherein PCR is performed by using an oligonucleotide having the nucleotide sequence shown in SEQ ID NO: 2 and an oligonucleotide having the nucleotide sequence shown in SEQ ID NO: 3, or an oligonucleotide having the nucleotide sequence shown in SEQ ID NO: 4 and an oligonucleotide having the nucleotide sequence shown in SEQ ID NO: 5 as primers (first detection method), and a method for detecting a non-B, non-C, non-G hepatitis virus gene wherein PCR is performed by using an oligonucleotide having the nucleotide sequence shown in SEQ ID NO: 6 and an oligonucleotide having the nucleotide sequence shown in SEQ ID NO: 8, or an oligonucleotide having the nucleotide sequence shown in SEQ ID NO: 7 and the oligonucleotide having the nucleotide sequence shown in SEQ ID NO: 8 as primers (second detection method).

The present invention also provides a method for differentiating non-B, non-C, non-G hepatitis virus genotypes wherein both of the aforementioned first detection method and the second detection method are performed for one sample, and results obtained from the both gene detection methods are compared; and a method for differentiating non-B, non-C, non-G hepatitis virus genotypes wherein hybridization is performed by using an oligonucleotide having a sequence present in any one of Genotypes 1–6 and specific for any one of the genotypes.

The present invention further provides a polypeptide having an amino acid sequence encoded within an open reading frame present in a nucleotide sequence of the gene of the present invention (also referred to as the polypeptide of the present invention hereinafter).

Specific examples of the polypeptide of the present invention include, for example, a polypeptide having the amino acid sequence shown in SEQ ID NO: 9 and polypeptide having the amino acid sequence shown in SEQ ID NO: 10. The polypeptide of the present invention includes a polypeptide comprising an amino acid sequence which is found in the amino acid sequence shown in SEQ ID NO: 9 or 10, and specific for a non-B, non-C, non-G hepatitis virus. The polypeptide of the present invention preferably contains a non-B, non-C, non-G hepatitis virus-specific epitope.

Furthermore, the present invention also provides a method for isolating non-B, non-C, non-G hepatitis virus particles wherein the virus particles are isolated based on density of the non-B, non-C, non-G hepatitis virus particles; virus particles isolated by the method; and a non-B, non-C, non-G hepatitis virus peptides obtained from the virus particles.

In addition, the present invention further provides a recombinant gene expression vector which comprises all or a part of a nucleotide sequence encoding the amino acid sequence shown in SEQ ID NO: 9 or 10; a transformant cell containing all or a part of a nucleotide sequence encoding the amino acid sequence shown in SEQ ID NO: 9 or 10; a non-B, non-C, non-G hepatitis virus antigen peptide or a fragment thereof expressed by the aforementioned transformant cell; and a method for producing a non-B, non-C, non-G hepatitis virus antigen peptide which comprises culturing the transformant cell under a condition that the non-B, non-C, non-G hepatitis virus antigen peptide is expressed, and collecting the expressed peptide.

Furthermore, the present invention provides a method for immunologically detecting a non-B, non-C, non-G hepatitis virus antibody using the polypeptide of the present invention (including that obtainable from virus particles) or the aforementioned virus particles as an antigen; a method for producing an antibody against the non-B, non-C, non-G hepatitis virus, which comprises immunizing an animal with the polypeptide of the present invention (including that obtainable from virus particles) or the aforementioned virus particles as an immunogen; antibodies obtained by the aforementioned method; and a method for immunologically detecting a non-B, non-C, non-G hepatitis virus antigen by using the aforementioned antibody.

The present invention further provides a vaccine containing a polypeptide having an amino acid sequence contained in an amino acid sequence encoded by an opening reading frame present in the nucleotide sequence shown in SEQ ID NO: 1, and containing an epitope sequence of a non-B, non-C, non-G hepatitis virus neutralizing antibody; and a vaccine containing the aforementioned virus particles.

The gene of the present invention is preferably also a non-B, non-C, non-G hepatitis virus gene having the nucleotide sequence shown in SEQ ID NO: 62 or an allogeneic variant gene thereof.

Also for this gene of the present invention, there are provided a polynucleotide having a nucleotide sequence complementary to a nucleotide sequence of the gene of the present invention; an oligonucleotide comprising a nucleotide sequence recognized in the gene of the present invention and specific for the gene or a nucleotide sequence complementary thereto; a method for detecting a non-B, non-C, non-G hepatitis virus gene wherein PCR is performed by using the aforementioned oligonucleotides as primers; a polypeptide having an amino acid sequence encoded within an open reading frame present in a nucleotide sequence of the gene of the present invention; a recombinant gene expression vector; a transformant cell; a non-B, non-C, non-G hepatitis virus antigen peptide or a fragment thereof expressed by the aforementioned transformant cell; a method for producing a non-B, non-C, non-G hepatitis virus antigen peptide; a methods for immunologically detecting non-B, non-C, non-G hepatitis virus antibodies; a method for producing a non-B, non-C, non-G hepatitis virus antibody; an antibody; a method for immunologicallly detecting a non-B, non-C, non-G hepatitis virus antigen; and a vaccine.

The present invention will be explained in detail hereinafter.

The present invention relates to a so far unknown virus different from any of already known viruses. The term "non-B, non-C, non-G hepatitis virus" used for the present invention means an etiologic virus transmitted via blood-borne infection, and causing hepatitis symptoms, and it is a so far unknown virus different from hepatitis B, C, and G viruses, which are similarly blood-borne infectious viruses. Further, it is also different from hepatitis A virus, hepatitis E virus, and hepatitis F virus, which are of non-blood-borne infectious type, and hepatitis D virus, which is a defective virus, and hence it eventually has the same meaning as non-A, non-B, non-C, non-D, non-E, non-F, non-G hepatitis virus.

Hepatitis symptoms means symptoms generally representing hepatitis such as abnormal hepatic function values and appearance of icterus.

In the present invention, the virus of the present invention is defined as a hepatitis virus based on the context of the discovery of the virus of the present invention, but it does not necessarily means that major diseases caused by the virus of the present invention should be hepatitis.

The present inventors designated a non-B, non-C, non-G hepatitis virus having a non-B, non-C, non-G hepatitis virus gene having the nucleotide sequence shown in SEQ ID NO: 1 or a gene considered as an allogeneic variant thereof as "HNT22" virus (abbreviated as "HNT22" hereinafter), which is included in the gene of the present invention. HNT22 can be also defined as a non-B, non-C, non-G hepatitis virus having a non-B, non-C, non-G hepatitis virus gene of the following (a) or (b):

(a) a non-B, non-C, non-G hepatitis virus gene having a nucleotide sequence from which a sequence having a length of from about 200 nucleotides to about 350 nucleotides can be amplified by PCR utilizing an oligonucleotide having a sequence shown in SEQ ID NO: 6 and an oligonucleotide having the nucleotide sequence shown in SEQ ID NO: 8 as primers, or (b) a non-B, non-C, non-G hepatitis virus gene having a nucleotide sequence from which a sequence having a length of from about 200 nucleotides to about 350 nucleotides can be amplified by PCR utilizing an oligonucleotide having a sequence shown in SEQ ID NO: 7 and an oligonucleotide having the nucleotide sequence shown in SEQ ID NO: 8 as primers.

Further, a non-B, non-C, non-G hepatitis virus having a gene not included in the aforementioned gene, i.e., having the nucleotide sequence shown in SEQ ID NO: 62 or a gene considered as an allogeneic variant thereof is designated as "TUS01 virus" (abbreviated as "TUS01" hereinafter).

That is, HNT22 and TUS01 are so far unknown viruses isolated form non-A, non-B, non-C, non-D, non-E, non-F, non-G hepatitis patients, and they were separated from patients of hepatitis whose etiology has so far been considered unknown, and virologically or molecular biologically different from any known viruses.

HNT22 and TUS01 can be generically defined as a virus having a gene comprising a nucleotide sequence of the nucleotide number 3–300 of the nucleotide sequence shown in SEQ ID NO: 1 or a nucleotide sequence having high homology thereto in its 5' end portion, and a nucleotide sequence of the nucleotide number 2902–3738 of the nucleotide sequence shown in SEQ ID NO: 1 or a nucleotide sequence having high homology thereto in its 3' end portion, and having a length including the 5' end nucleotide sequence and the 3' end nucleotide sequence of about 3500 nucleotides to about 4000 nucleotides, preferably about 3600 nucleotides to about 3900 nucleotides.

In the present invention, hepatitis that is positive for HNT22 is called "HNT22 type hepatitis", and hepatitis that is positive for TUS01 is called "TUS01 type hepatitis".

It has been known that viruses are in general more likely to undergo mutations, and such mutations are more likely to be fixed in their genes compared with other higher organisms. Accordingly, a number of strains (allogeneic variants) may exist within the same species, and genotypes sharing a substantial gene sequence are also present. The terms HNT22 and TUS01 are used in the present invention as generic names of viruses including a possible great number of such strains and genotypes.

Because it has been known that viruses show high frequencies of mutations and fixation of such mutations in genes as described above, definition of a virus by its gene sequences or amino acid sequences should be construed to include not only a virus containing specifically exemplified sequences but also those having gene sequences or amino acid sequences in a range considered to be substantially homologous. The substantially homologous range can be defined based on a ratio of homology which enables clear differentiation of one virus from the other virus by comparing their gene sequences or amino acid sequences. The substantially homologous range can also be defined by referring sequence diversity within a species of known similar viruses.

According to the aforementioned criteria, a gene having a nucleotide sequence having a homology to those of the HNT22 genes or the TUS01 genes of 55% or more, preferably 60% or more, more preferably 70% or more, particularly preferably 80% or more may be considered to be substantially homologous to the gene of the present invention, and fall within the scope of the present invention.

When genetic conservation within the HNT22 genes and homology with other viruses were actually determined for the HNT22 genes of the present invention, the homology within the HNT22 genes (conservation) was 55% or more, and the highest homology with other viruses was less than 60%.

Homology herein used means homology of nucleotide sequences and amino acid sequences, and it specifically means a ratio of a number of conformed nucleotides or amino acids to a number of nucleotides or amino acids contained in the whole sequences expressed in terms of percentage when sequences to be compared are aligned so that they should show the best conformance with a necessary deletion.

The hepatitis C virus (HCV), which causes blood-borne infectious hepatitis like the virus of the present invention, exhibited a homology of 60% or more within the species. Further, it has been reported that HCV of the same genotype exhibited a homology of 80% or more except for the partial high mutation region. From these facts, it is considered to be appropriate that the range of the gene of the present invention should be defined in terms of the aforementioned homology.

Similarly, as for the homology of the encoded amino acid sequence, those having a homology to the viruses of the present invention of usually 65% or more, preferably 70% or more, more preferably 80% or more, particularly preferably 90% or more are substantially homologous to the viruses of the present invention, and included in them.

The genotypes existing in the HNT22 genes may variously classified, but, when based on the positions 1939–2160 in SEQ ID NO: 1 (referred to as nt1939–2160 hereinafter), an HNT22 gene having the nucleotide sequence shown in SEQ ID NO: 45 (Genotype 1), an HNT22 gene having the nucleotide sequence shown in SEQ ID NO: 46 (Genotype 2), an HNT22 gene having the nucleotide sequence shown in SEQ ID NO: 47 (Genotype 3), an HNT22 gene having the nucleotide sequence shown in SEQ ID NO: 48 (Genotype 4), an HNT22 gene having the nucleotide sequence shown in SEQ ID NO: 49 (Genotype 5), an HNT22 gene having the nucleotide sequence shown in SEQ ID NO: 50 (Genotype 6), and an HNT22 gene having the nucleotide sequence shown in SEQ ID NO: 51 (Genotype 7) can be mentioned.

By utilizing these nucleotide sequences, HNT22 viruses of a specific genotype can be detected or distinguished. As methods for differentiation, not only a method utilizing amplification by such a method as mentioned in Examples hereinafter and sequencing, but also a method by using an oligonucleotide having a sequence specific for any of the genotypes as a primer to amplify only a gene sequence of the corresponding genotype, a method by using such an oligonucleotide as probe to selectively detect the corresponding gene sequence, and a combination of these methods can be mentioned. Oligonucleotides, reaction conditions and the like that can be used for these methods can be selected according to methods known to those skilled in the art. For example, partial sequences characteristic of the genotypes (referred to as genotype-specific sequences hereinafter) can easily be selected by comparing the genotype sequences with one another. It is easy for those skilled in the art to select an oligonucleotide having a genotype-specific sequence or a sequence complementary thereto, and not hybridizing other HNT22 genotypes, or select a condition that an oligonucleotide having a genotype-specific sequence substantially cannot hybridize with other genotype sequences (Protein, Nucleic acid, Enzyme, Front Line of PCR, 1996, Kyoritsu Shuppan). Oligonucleotides selected as described above can be utilized as a primer or a probe to perform HNT22 genotype-specific amplification or detection.

The aforementioned HNT22 genes can be detected as one having a nucleotide sequence which can be amplified by PCR utilizing an oligonucleotide having the nucleotide sequence shown in SEQ ID NO: 6 (NG059) and an oligonucleotide having the nucleotide sequence shown in SEQ ID NO: 8 (NG063) as primers, and/or PCR utilizing an oligonucleotide having the nucleotide sequence shown in SEQ ID NO: 7 (NG061) and an oligonucleotide having the nucleotide sequence shown in SEQ ID NO: 8 (NG063) as primers.

In particular, the HNT22 genes having the nucleotide sequence shown in SEQ ID NO: 1 can be detected as one having a nucleotide sequence which can be amplified by PCR utilizing an oligonucleotide having the nucleotide sequence shown in SEQ ID NO: 2 (RD037) and an oligonucleotide having the nucleotide sequence shown in SEQ ID NO: 3 (RD038) as primers, and/or PCR utilizing an oligonucleotide having the nucleotide sequence shown in SEQ ID NO: 4 (RD051) and an oligonucleotide having the nucleotide sequence shown in SEQ ID NO: 5 (RD052) as primers.

The HNT22 genes of the present invention were obtained by the present inventors according to the following procedure.

It has been recognized that there are cases clearly exhibiting hepatitis symptoms while they are negative for any of known hepatitis virus markers. Such cases might be infection cases of unknown and non-elucidated hepatitis virus.

On the other hand, it may be thought that viruses are not present in healthy persons in principle. However, among hepatitis virus-infected patients, there may be asymptomatic carriers not exhibiting abnormality in their hepatic function and apparently healthy.

Therefore, the present inventors performed screening of genes present in hepatitis cases of which cause was indistinct, but absent in healthy persons or patients before crisis of hepatitis in order to search for unknown hepatitis virus. As a method for detecting genes present in one of groups to be compared as mentioned above, the known Representational Difference Analysis (Science 259, 946–950, 1993, abbreviated as "RDA method" hereinafter) was employed.

By determining sequences of the candidate genes obtained by the RDA method, the present inventors confirmed that the sequences were not homologous to sequences of known viruses.

Subsequently, a gene detection system which utilized an oligonucleotide primer constituting a part of the gene sequences was constructed, and the genes were confirmed to be detected in other hepatitis cases of which cause was not elucidated.

Further, a large number of sequences from cases positive for the genes were analyzed and compared to show that genotypes were present in the viruses, and a method for differentiating the genotypes utilizing sequences specific for the genotypes was constructed.

Furthermore, it was confirmed that the genes were not found in most of healthy persons. It was also confirmed that among the cases positive for the genes there were some cases which were negative for the genes before blood transfusion, but infected due to blood transfusion with blood positive for the genes and maintained as positive thereafter.

It was also verified that the genes were not those derived from the hosts.

From analyses utilizing density gradient centrifugation, a fraction positive for the genes was localized at a specific density as observed in other virus particles.

It was also verified that the virus was a single-stranded DNA virus by analysis based on the presence or absence of a reverse transcriptase reaction step, analysis utilizing a deoxyribonuclease, and experiments with restriction endonucleases.

Analyzing all of the above results, it was confirmed that the genes were transmitted by blood transfusion and maintained, hepatitis symptoms were observed in infection cases, positive persons were not so many among healthy persons, and sequences of the genes were not homologous to already known virus gene sequences. Taken together, the present inventors concluded that the viruses contained so far unknown hepatitis virus genes.

It was assumed that the aforementioned genes were a part of a virus gene based on their structures. The present inventors obtained the gene of the present invention by the known gene walking method based on the aforementioned gene sequences.

Embodiments of the present invention will be explained hereinafter by referring to the HNT22 genes, but it will be readily understood that the TUS01 genes can be used similarly.

The present invention provides an oligonucleotide or polynucleotide which has a sequence specific for the HNT22 genes, and can complementarily hybridize to the HNT22 genes under stringent conditions. Because of the characteristics of the oligonucleotide/polynucleotide, it can be effectively used as a primer for amplification of the HNT22 genes or as a probe for capturing or detecting the HNT22 genes in samples.

The term "specific sequence" herein used means a characteristic sequence portion which is present in a nucleotide sequence of a gene of interest or an amino acid sequence deduced from the nucleotide sequence, and distinguishable from sequences other than a sequence of interest. Whether a sequence is the characteristic sequence or not can be determined based on homology of sequence. Specifically, it may mean a sequence exhibits a homology of 10% or less with respect to known sequences other than the gene of interest having the same length, when the sequence is compared with the known sequences in a conventional manner, for example, by searching databases. Alternatively, it may be decided by determining if a gene of interest can be detected, identified and amplified by utilizing the sequence. Specifically, as for nucleotide sequences, when an oligonucleotide or polynucleotide having the sequence or an oligonucleotide or polynucleotide having a sequence complementary to the nucleotide sequence is used in a method for detection or amplification of genes known to those skilled in the art as a primer or probe, if the oligonucleotide or polynucleotide could detect, identify or amplify a gene of interest in a manner distinguishable from other genes with statistic significance, the sequence should be determined as specific for the gene of interest. As for amino acid sequences, whether a sequence is a specific sequence or not can similarly be determined based on homology of sequence. Specifically, a specific amino acid sequence is an amino acid sequence having such a length that it should show homology of about 10% or less when compared with known sequences. Alternatively, when an antibody raised by using a peptide composed of or containing an amino acid sequence encoded by a gene of interest as an antigen and verified to be bound to the amino acid sequence does not bound to or bound in a weaker degree with statistical significance to other antigens not derived from the amino acid sequence, the amino acid sequence can be determined as a sequence specific for the gene of interest.

The terms "polynucleotide" and "oligonucleotide" used for the present invention mean a nucleotide polymer having an arbitrary length, and include ribonucleotides and deoxyribonucleotides, for example, single- and double-stranded DNA, and single- and double-stranded RNA. These terms include not only unmodified polynucleotides, but also polynucleotides and oligonucleotides having a modification by, for example, methylation, capping, enzyme labeling, fluorescence labeling and the like.

The polynucleotides and the oligonucleotides of the present invention include not only those derived from genomic DNA, but also polynucleotides and oligonucleotides obtained by synthesis, replication, transcription or amplification according to conventional methods.

The polynucleotides of the present invention include the exemplified sequences, sequences substantially homologous thereto, and polynucleotides having a sequence complementary thereto.

The oligonucleotides and the polynucleotides of the present invention can be used as primers for amplification of the HNT22 genes by PCR. In this method, a portion of the HNT22 genes between the primers can be amplified, thereby confirming that the portion of the HNT22 genes, i.e., HNT22 is present in a tested sample.

The present invention also provides an oligonucleotide probe or polynucleotide probe useful for capturing the HNT22 genes by hybridization, and detecting the HNT22 genes.

A suitable probe used for the capture or detection can be selected from the gene sequences in the same manner as the selection of the primers mentioned above, and a selected probe can be labeled in a conventional manner. It is also possible to detect a gene by capturing with the probe mentioned above a gene amplified with the primers mentioned above, and in particular, it becomes possible to distinguish HNT genotypes by utilizing a probe comprising a genotype-specific sequence.

The oligonucleotide of the present invention is usually an oligonucleotide having a relatively short sequence continuously present in a polynucleotide, and include those having the sequence in homologous or complementary polynucleotides. Its length is generally 6–50 nucleotides, preferably 10–30 nucleotides, more preferably 15–20 nucleotides.

Because the HNT22 genes show diversity as described above, a nucleotide sequence in a region where a nucleotide sequence is relatively well conserved among virus strains may be a nucleotide sequence specific for the genes. It is easy for those skilled in the art to select such a nucleotide sequence based on the nucleotide sequences disclosed herein. Specific examples of such an oligonucleotide include, for example, a polynucleotide having the nucleotide sequence shown in SEQ ID NO: 2 (RD037), polynucleotide having the nucleotide sequence shown in SEQ ID NO: 3 (RD038), polynucleotide having the nucleotide sequence shown in SEQ ID NO: 4 (RD051), polynucleotide having the nucleotide sequence shown in SEQ ID NO: 5 (RD052) polynucleotide having the nucleotide sequence shown in SEQ ID NO: 6 (NG059), polynucleotide having the nucleotide sequence shown in SEQ ID NO: 7 (NG061), polynucleotide having the nucleotide sequence shown in SEQ ID NO: 8 (NG063) and the like.

The present invention also provides a method for detecting the HNT22 genes wherein PCR is performed by utilizing the oligonucleotides of the present invention as primers.

Specific examples of the methods include, for example, a method for detection of the HNT22 genes wherein PCR is performed by utilizing an oligonucleotide having the nucleotide sequence shown in SEQ ID NO: 2 (RD037) and an oligonucleotide having the nucleotide sequence shown in SEQ ID NO: 3 (RD038), or an oligonucleotide having the nucleotide sequence shown in SEQ ID NO: 4 (RD051) and an oligonucleotide having the nucleotide sequence shown in SEQ ID NO: 5 (RD052) as primers (first detection method), and a method for detection of the HNT22 genes wherein PCR is performed by utilizing an oligonucleotide having the nucleotide sequence shown in SEQ ID NO: 6 (NG059) and an oligonucleotide having the nucleotide sequence shown in SEQ ID NO: 8 (NG063), or an oligonucleotide having the nucleotide sequence shown in SEQ ID NO: 7 (NG061) and the oligonucleotide having the nucleotide sequence shown in SEQ ID NO: 8 (NG063) as primers (second detection method).

Samples used for PCR are prepared by extracting nucleic acids or DNA from biological samples such as plasma or sera collected from specimens by a known method. This preparation can be performed using a commercially available kit for extraction.

Conditions for PCR are suitably selected according to known PCR methods using a thermostable DNA polymerase.

Amplification products resulted from PCR can be detected by a known method such as electrophoresis, and the HNT22 genes can be detected based on the presence of the amplification products.

The present invention also provides a method for differentiating HNT22 genotypes wherein both of the aforementioned first detection method and the second detection method are performed for one sample, and results obtained from the both gene detection methods are compared, and a method for differentiating HNT22 genotypes wherein hybridization is performed by using an oligonucleotide having a sequence present in the genes of Genotypes 1–6 and specific for the corresponding genotype.

The sequence specific for each genotype can be selected by those skilled in the art based on nucleotide sequences herein disclosed, or based on nucleotide sequences of genes detected by the methods for detection of genes mentioned above. Hybridization can be performed according to a known method. Specifically, nucleic acids are prepared from a biological sample, the prepared nucleic acids and an oligonucleotide are hybridized under stringent conditions, and the hybridized products containing the oligonucleotide are detected.

The specific oligonucleotides mentioned above are of course a part of examples, and other oligonucleotides which achieve the same object as mentioned above can be readily selected based on the HNT22 genes disclosed herein by utilizing techniques known to those skilled in the art. It is also easy to select an oligonucleotide which can be utilized for detecting both of the HNT22 genes and the TUS01 genes by combining the nucleotide sequences of the both genes disclosed herein and utilizing techniques known to those skilled in the art. For example, an oligonucleotide having the nucleotide sequence shown in SEQ ID NO: 57 (NG054) and an oligonucleotide having the nucleotide sequence shown in SEQ ID NO: 60 (NG065), or an oligonucleotide having the nucleotide sequence shown in SEQ ID NO: 57 (NG054) and an oligonucleotide having the nucleotide sequence shown in SEQ ID NO: 61 (NG021) can be mentioned as such oligonucleotides, and by performing PCR using these as primers, the HNT22 genes and the TUS01 genes can be detected. Similarly, those skilled in the art will be readily able to select oligonucleotides which can be utilized for detecting only the HNT22 genes, or only the TUS01 genes.

The present invention further provides a polypeptide having an amino acid sequence encoded within an open reading frame found in nucleotide sequences of the genes of the present invention (referred to as the polypeptide of the present invention hereinafter).

The term "polypeptide" herein means a linearly linked polymer of amino acids, and its length is not particularly limited. Accordingly, the polypeptide of the present invention includes any of those usually referred to as oligopeptides, proteins, and peptides, and as for their origin, it includes not only naturally occurring ones, but also fragments of the naturally occurring ones and those prepared by various means such as chemical syntheses and recombinant expression techniques. As described above, it has been known that viruses show differences of gene sequences even within the same species, and therefore similarly show differences in amino acid sequences. Accordingly, homology of an amino acid sequence necessary for determining the sequence as one of the viruses of the present invention is 65% or more, preferably 70% or more, more preferably 80% or more, and particularly preferably 90% or more.

The term "open reading frame" (abbreviate as "ORF" hereinafter) used for the present invention means a region of nucleotide sequence encoding a polypeptide or a part thereof. This sequence is transcribed and translated into a polypeptide when it is placed under a suitable condition. Boundaries of a coding sequence are an initiation codon at the 5' end and a termination codon at the 3' end.

It is known in the art to deduce, from a gene sequence, an encoded amino acid sequence, and therefore what is important is to define ORF in a gene sequence. ORF can be determined as follows.

A triplet nucleotide sequence which could be an initiation codon, where translation into an amino acid starts, should be identified in an obtained gene sequence. This location is assumed as an initiation codon, and ORF encoding a polypeptide of a certain size is determined within a range where a termination codon does not appear. Examples of amino acid sequences which are obtained in this manner include the amino acid sequences shown in SEQ ID NOS: 9 and 10.

The polypeptide of the present invention preferably comprises an amino acid sequence specific for HNT22. An amino acid sequence specific for HNT22 can be selected by those skilled in the art based on amino acid sequences encoded by the nucleotide sequences disclosed herein, or amino acid sequences encoded by nucleotide sequences of genes detected by the aforementioned methods for detection of genes.

The polypeptide of the present invention more preferably contains an HNT22-specific epitope.

The term "epitope" used in the present invention means an antigenic determinant. The antigenic determinant is a site which is present in an antigen molecule and directly bound to an antibody, and it is constituted by at least three amino acids, usually 5–10 amino acids in the steric configuration. Methods for determining a location of epitope and its configuration in a steric structure of a peptide are known in the art, and can be performed by those skilled in the art. Accordingly, the term "HNT22-specific epitope" used in the present invention means an antigenic determinant specific for HNT22, and it is an epitope composed of an amino acid sequence specific for HNT22. This epitope is usually composed of eight or more contiguous amino acids.

The expression "containing an epitope" used in the present invention means that such an epitope sequence as defined above is contained as a part of polypeptides, and specific examples of such polypeptides containing an epitope include those composed of an epitope sequence bound to a carrier peptide or a linker peptide.

The polypeptide of the present invention can be effectively used as an antigen for antibody tests or an immunogen for preparing antiviral antibodies. It is expected that viral polypeptides include an amino acid sequence which does not have an amino acid sequence specific for the virus and may cause non-specific antibody reactions when this portion is used as an antigen. Therefore, it is important also in the present invention to specify a sequence suitable for antibody tests from the whole amino acid sequence. As a method for identifying such a specific sequence, i.e., an epitope sequence, there is available a method wherein peptides each having a certain length that cover the whole sequence are synthesized, and presence or absence or degree of reaction of each peptide with an antiviral antibody, namely, a serum of a patient infected with the virus is utilized. Instead of the above method involving synthesis, a phage library using λgt11 can be prepared and screened with a blood serum of the patient.

The present invention also provides a method for isolating non-B, non-C, non-G hepatitis virus particles wherein the particles are isolated based on density of the particles, virus particles isolated by the aforementioned method, and a non-B, non-C, non-G hepatitis virus peptide obtained from the aforementioned virus particles.

The term "virus particles" used in the present invention means a fraction positive for the gene of the present invention which is collected as a fraction of a particular density by density gradient centrifugation, which is used as a usual method for isolation of virus particles, and it is not limited to those having a particle structure in a morphological sense, or infectious particles.

Viruses have densities corresponding to their particle structure, and they can be separated from other coexisting substances based on the density. The most usual method for isolating virus particles based on density is a method utilizing density gradient centrifugation. In this method, a gradient density carrier layer is formed in a centrifugation tube using sucrose or the like, then a fraction containing viruses is overlaid on the layer, and ultracentrifugation is performed. This technique is based on the fact that, when viruses migrated by centrifugal force reach a layer having the same density as the viruses, the centrifugal force and buoyancy reach equilibrium, and the viruses stop the migration, thereby the viruses are concentrated in that fraction.

The polypeptide can be obtained from virus particles obtained by the method mentioned above by a known method. For example, virus particles are treated with a denaturation agent, and a polypeptide is separated from other components.

The present invention also provides a gene expression vector into which the HNT22 gene or a partial sequence thereof is integrated. The term "recombinant expression vector" herein used means a vector for inserting an exogenous polynucleotide into a gene of a host cell so that the polynucleotide could be expressed. Specifically, it is a vector having control sequences enabling the integration of the polynucleotide. The term "partial" means that the sequence is composed of a part of the genes which encodes a peptide sufficient for exhibiting antigenicity.

The expression vector can be effectively used for obtaining a viral peptide having immunological activity or biological activity. Various vectors for integrating a gene desired to be expressed are currently known, and various host cells for the integration of the vectors and consequent expression of peptides are also known.

The gene expression vector provided by the present invention is a recombinant expression vector having an HNT22 genome or ORF thereof, wherein the ORF is operably linked to regulatory sequences compatible with a desired host. A recombinant gene expression system can be constructed by using the expression vector.

The term "transformant cell" herein used means a cell of which gene is integrated with all or a part of a gene of the present invention, and which can express all of or a part of a polypeptide encoded by the gene of the present invention.

The transformant cell provided by the present invention can be obtained by directly introducing a polynucleotide containing all or a part of the gene of the present invention, or introducing a recombinant expression vector integrated with such a polynucleotide into a host cell to transform the host cell. In the present invention, known transfer vectors and host cells can be used.

The polypeptide produced by the transformant cell (HNT22 virus antigen peptide) can be obtained by culturing the transformant cell under a condition that the HNT22 virus antigen peptide can be expressed, and collecting the expressed polypeptide.

The present invention provides a method for immunologically detecting an HNT22 antibody by using HNT22 particles, an HNT22 polypeptide, an HNT22 epitope, or a polypeptide containing the HNT22 epitope as an antigen. As methods for detection of antibodies using peptide antigens, there can be mentioned immunonephelometry, enzyme immunoassay, radiometric immunoassay, agglutination method and the like, and these methods can be used for the present invention.

The present invention also provides a method for preparing an HNT22 antibody by utilizing HNT22 particles, an HNT22 polypeptide, an HNT22 epitope, or a polypeptide containing the HNT22 epitope, which is purified or partially purified, as an immunogen, and the HNT22 antibody. As a method for preparing the antibody by utilizing purified or partially purified virus particles or polypeptides, conventional methods can be used.

The present invention provides a method for immunoassay of an HNT22 antigen by utilizing an antibody specifically binding to HNT22 and a kit therefor. As an example of the method for assaying the antigen by using the antibody, there can be mentioned a method comprising:

(1) a step of reacting an antigen in a sample with an antibody capable of binding to HNT22 which are immobilized on a solid phase of a reaction vessels or reaction carrier, so that the antigen in the sample should be captured by the antibody bound to the solid phase through antigen-antibody reaction, (2) a step of further reacting the captured antigen, after an appropriate. washing step, with an appropriately labeled antibody capable of binding to HNT22 and having specificity for HNT22, and (3) a step of detecting the binding antibody, after an appropriate washing step, by utilizing the function of the labeled antibody.

As another method, there can be mentioned a method comprising:

(1) a step of reacting a sample to be assayed with a suitably labeled polypeptide having an HNT22 epitope at a defined concentration for a certain period of time, (2) a step of reacting the sample which has undergone the step (1) with an HNT22 antibody immobilized on a solid phase of a reaction vessel or reaction carrier, so that the antigen in the sample should sufficiently bind to the antibody on the solid phase, and (3) a step of separating labels bound to the reaction vessel or reaction carrier and unbound labels, and measuring the bound labels or the unbound labels.

Other methods utilized for assaying the viral antigen such as agglutination method, reversed passive agglutination method, enzyme immunoassay, radiometric immunoassay, and fluorescence polarization method and the like can also be used for the present invention.

The present invention provides a vaccine comprising purified HNT22 particles, a polypeptide containing a neutralizing antibody epitope obtained from the purified virus particles, HNT22 particles and a polypeptide containing a neutralizing antibody epitope obtained by using recombinant expression, a purified polypeptide and a fragment containing a neutralizing antibody epitope obtained from the expressed virus particles or the expressed polypeptide, or a polypeptide containing a neutralizing antibody epitope chemically synthesized based on the gene sequence of the virus.

For the preparation of the vaccine of the present invention, a protein bearing an antigenically active region of HNT22 obtained by the aforementioned method for synthesis or recombinant expression based on the genes disclosed herein can be used. As for known viruses, peptide antigens and recombinant antigens containing epitopes of envelope antigens have such activity. Other structural protein antigens also may have such activity by themselves or when combined with other antigens. Specifically, peptide antigens or recombinant antigens containing epitopes of envelope antigens contain the epitope. Other structural protein antigens may also contain a neutralizing antibody epitope by themselves or when combined with other antigens.

By using an antigen which is expressed by utilizing the gene of the present invention or HNT22 particles purified by the isolation method of the present invention, a multivalent vaccine containing a plurality kinds of neutralizing antibody epitopes can be obtained. When isolated and purified particles are used, the virus should be inactivated, and it can be realized by a known method such as treatment with formalin.

The method for preparing a vaccine containing an immunogenic polypeptide as an active ingredient may also use a known one. That is, it is prepared as a liquid preparation, or a suspension as an injection solution, or a solid preparation suitable for being dissolved or suspended in a liquid before injected. The immunologically active ingredient is mixed with a suitable excipient. As the excipient, water, physiological saline, dextrose, glycerol, ethanol and the like can be mentioned. An auxiliary in a small amount can also be added as required. As the auxiliary, humectants, emulsifiers, pH buffers, adjuvants and the like can be mentioned. Exampels of the adjuvant include, for example, aluminum hydroxide, N-acetyl-muramyl-L-threonyl-D-isoglutamine, N-acetyl-muramyl-L-alanyl-D-isoglutamine and the like.

Administration formulas of these vaccines affording the desired effect can be suitably defined. Dose per administration is generally 5 $\mu$g to 250 $\mu$g, and it is decided depending on body weight and ability of immunological response of individuals to be administered, desired degree of antibody induction and the like. Frequency of administration may also be selected according to similar standards.

BRIEF EXPLANATION OF THE DRAWINGS

Figure 2:
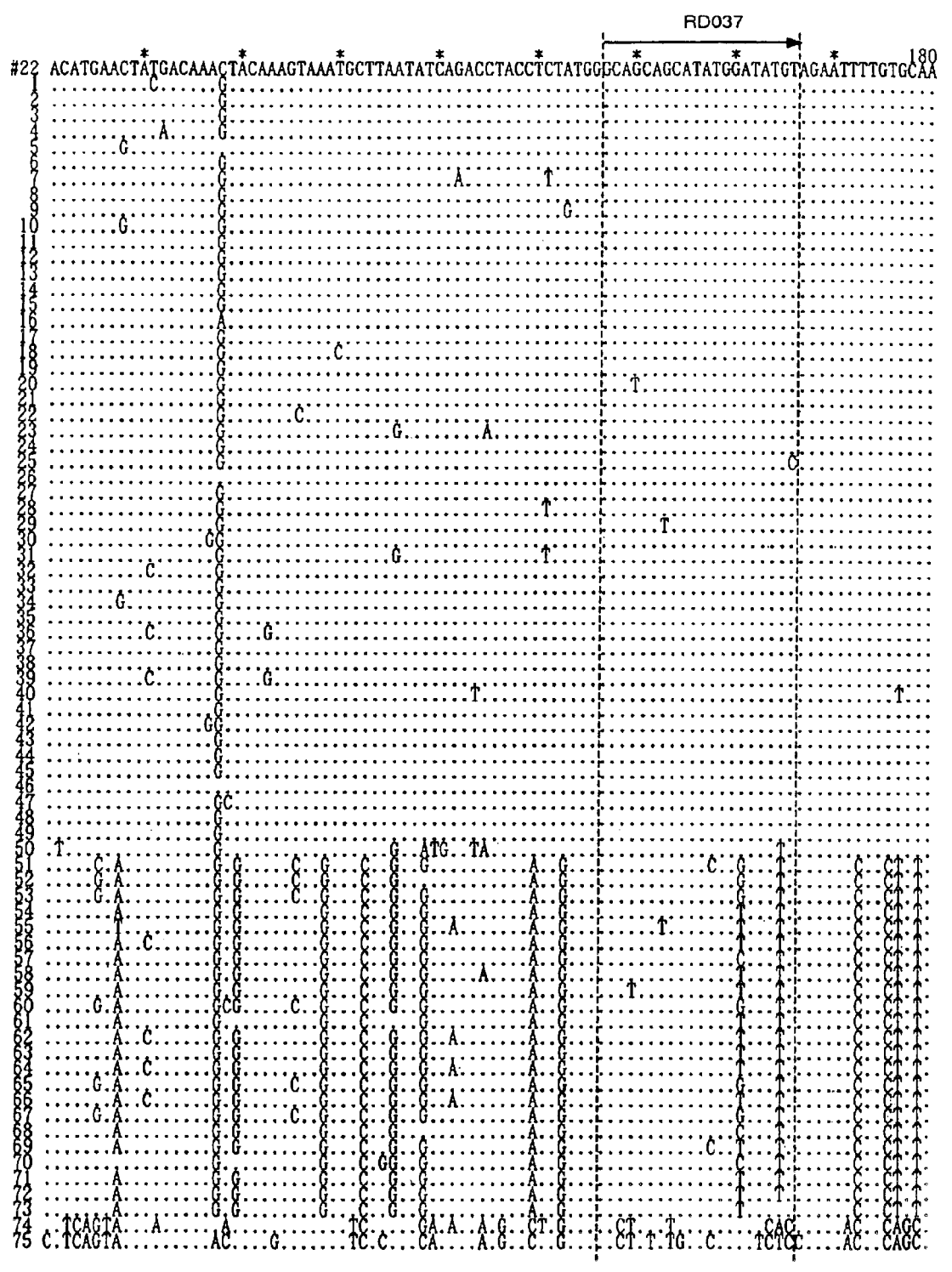

FIGS. 1–5 show comparison of sequences of 396 nucleotides between NG001 (SEQ ID NO: 40) and a sequence complimentary to RD052 (SEQ ID NO: 5) (corresponding to nt1862–2257 in SEQ ID NO: 1) of the genes obtained from 75 of HNT22 positive samples.

The whole sequence of the corresponding region (nt78–299) of #22 (SEQ ID NO: 11) is shown at the top of the sequences of the samples, and thereunder nucleotides of Samples 1–75 different from #22 are shown with alphabet while positions of the same nucleotide are shown with dots (•). Based on homology of sequences (corresponding to nt1939–2160 in SEQ ID NO: 1, nt78–299 in SEQ ID NO: 11), they can be classified into four groups, group of Samples 1–49 (designated as Genotype I), group of Samples 50–73 (designated as Genotype II), Sample 74 and Sample 75.

The locations of the primers used in the Examples 2 and 3 are shown in the top row. It can be seen that mismatches are commonly present at the 3' end side of the primers of RD037 (SEQ ID NO: 2) and RD051 (SEQ ID NO: 4) in Genotype II and Samples 74 and 75.

Figure 1:
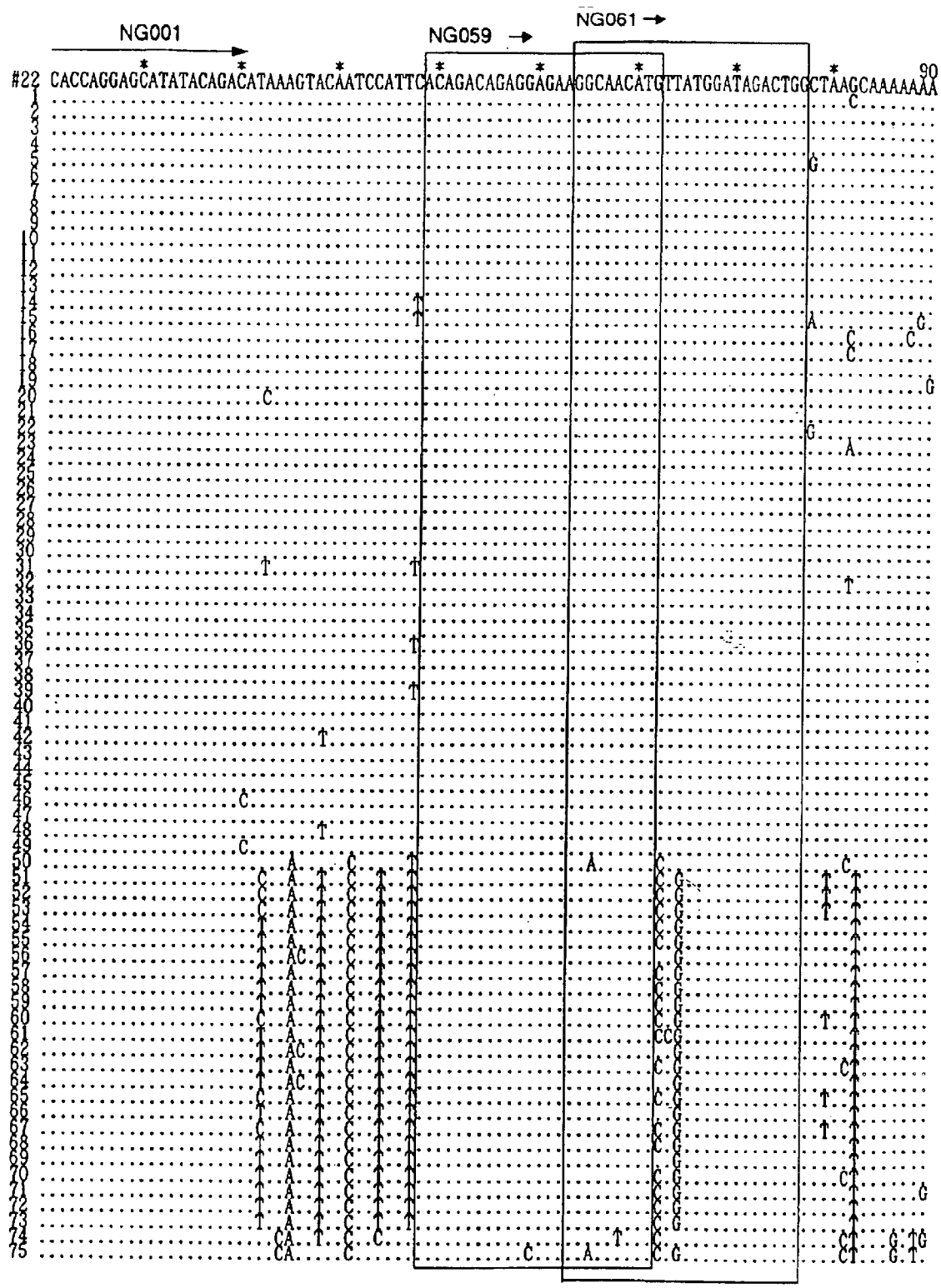
Figure 3:
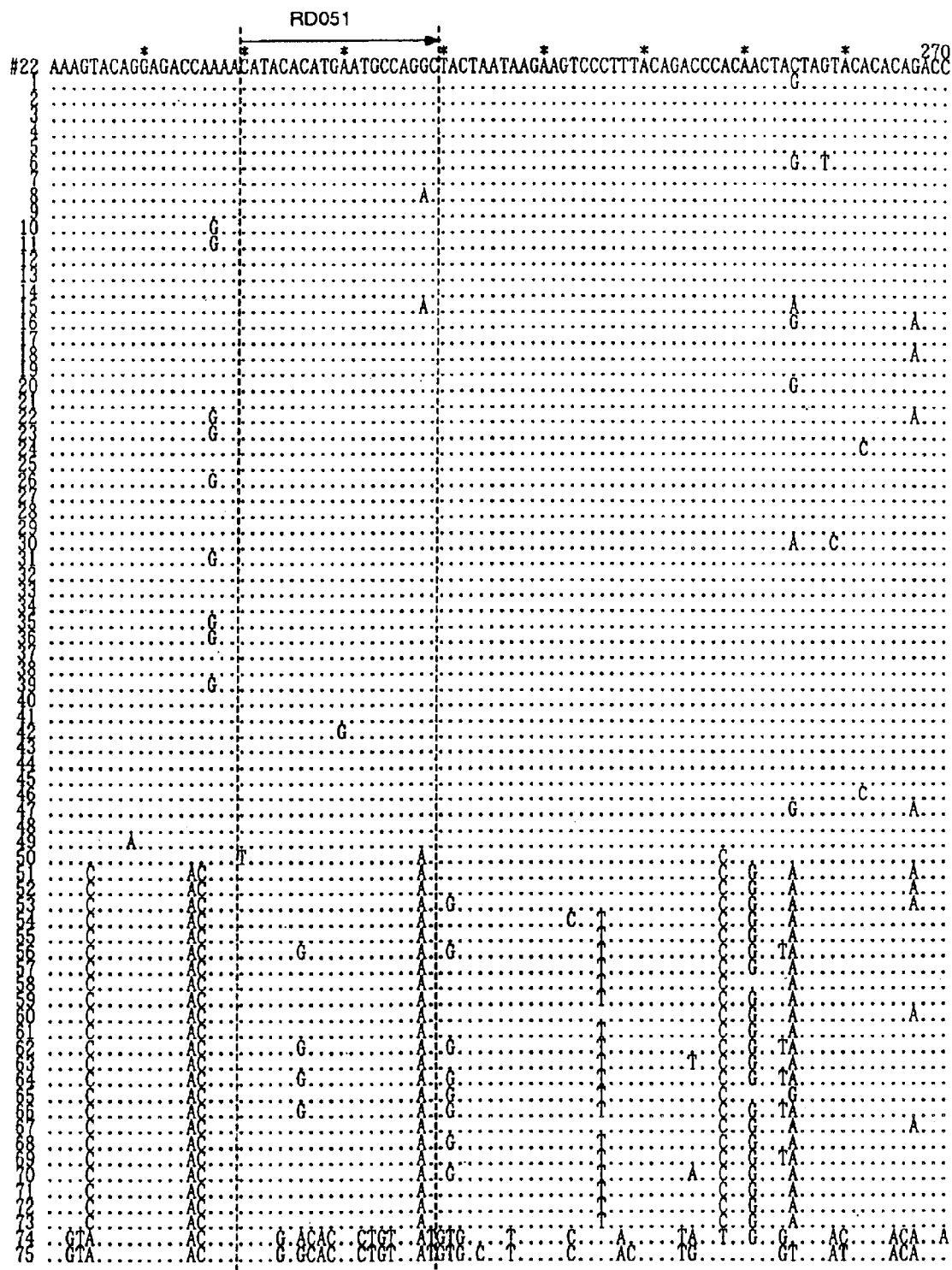
Figure 4:
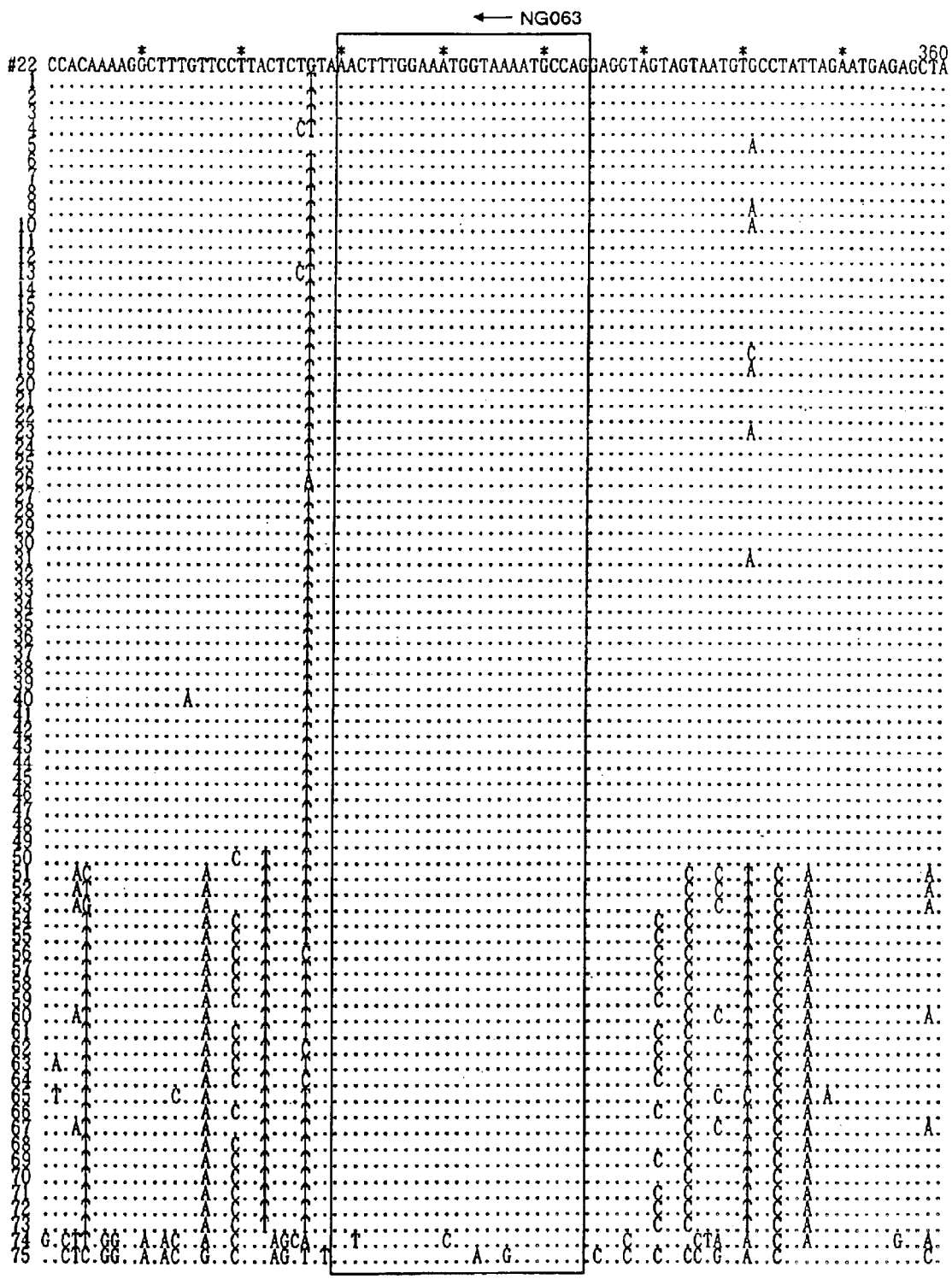
Figure 5:
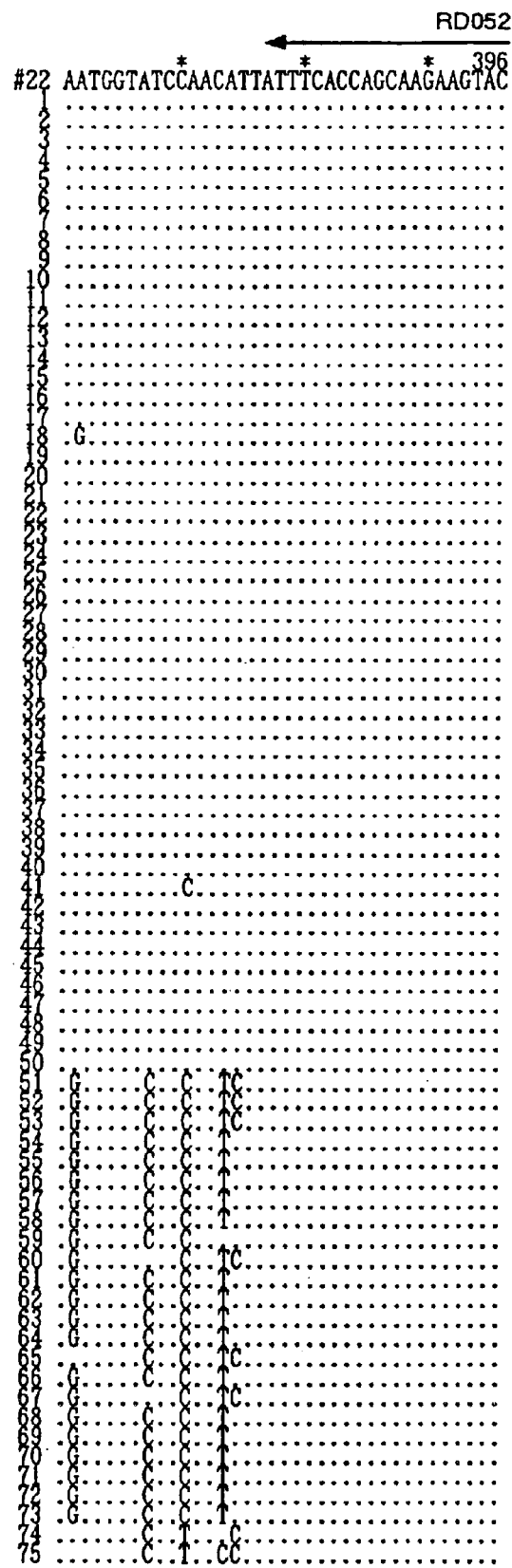
Figure 6:
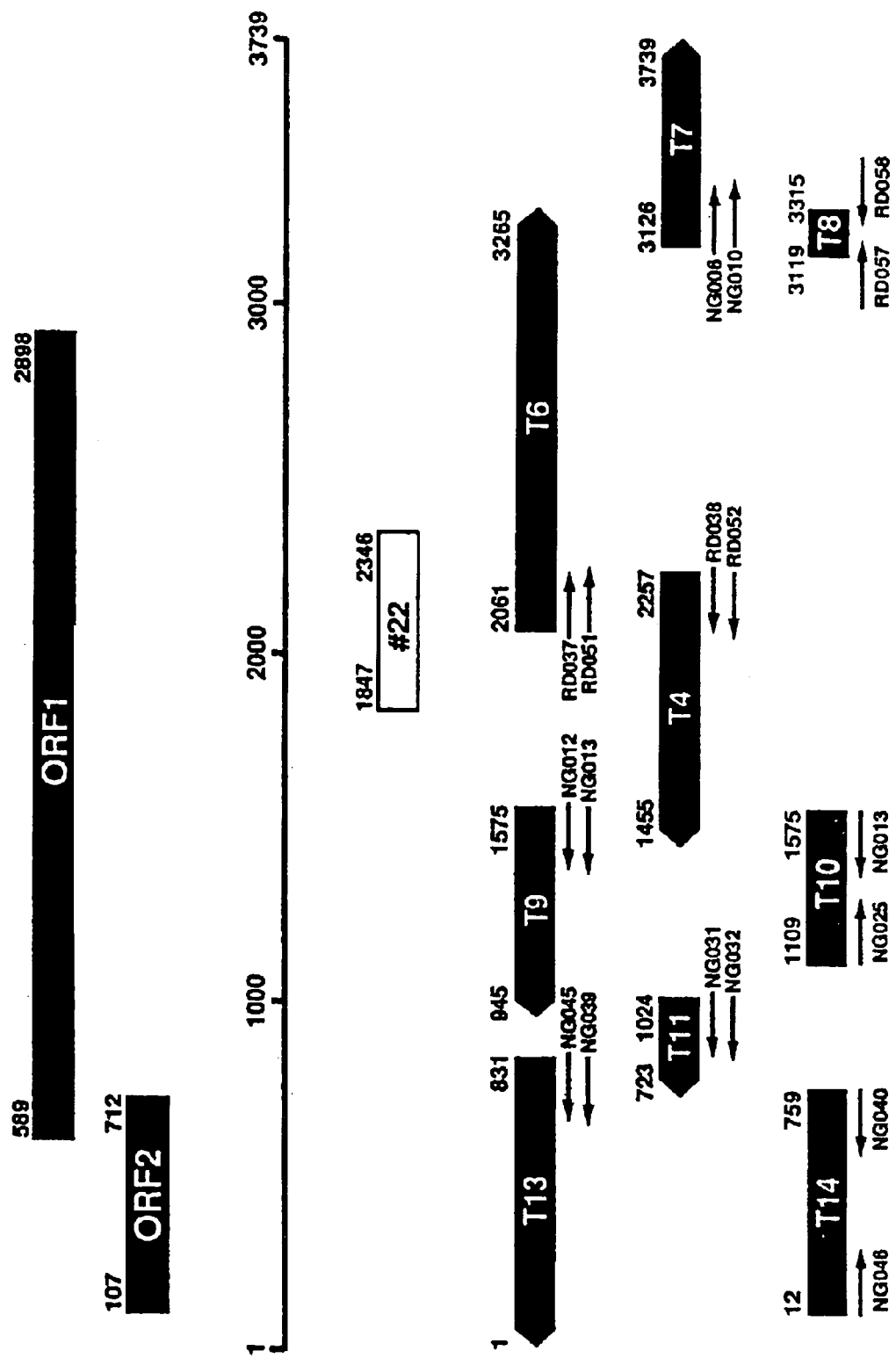

FIG. 6 represents extension of #22 clone sequence using gene walking (Example 4).

FIG. 7 represents comparison of:

(1) HNT22 gene sequence in blood for transfusion (SEQ ID NO: 11), (2) HNT22 gene sequence derived from a patient two weeks after blood transfusion, and (3) HNT22 gene sequence derived from a patient four weeks after blood transfusion for HNT22 infection cases caused by blood transfusion (Example 7). The compared sequences are completely consistent with one another.

Figure 8:
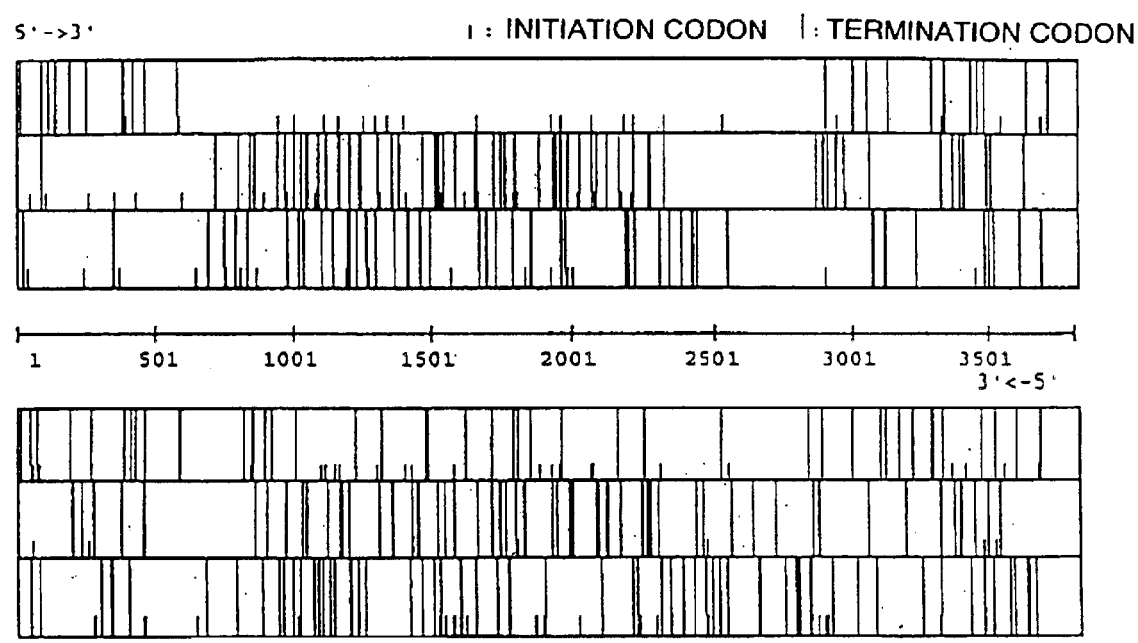

FIG. 8 represents the results of searching of open reading frame (ORF) of the HNT22 genes (Example 10).

Upper 3 frames: candidate locations of initiation codon and termination codon in the nucleotide sequence shown in SEQ ID NO: 1. The short vertical bars indicate initiation codons, and the long vertical bars indicate termination codons. The frames show sequences each of which open reading frame is shifted by one nucleotide for every sequence. Long ORFs were found in the first and the second frames.

Lower 3 frames: candidate locations of initiation codon and termination codon in a sequence complementary to the nucleotide sequence shown in SEQ ID NO: 1. Long ORF was not recognized in any of the frames.

FIG. 9 represents hydrophilicity/hydrophobicity scores of polypeptides based on the amino acid sequences encoded by the open reading frames 1 and 2.

Figure 10:
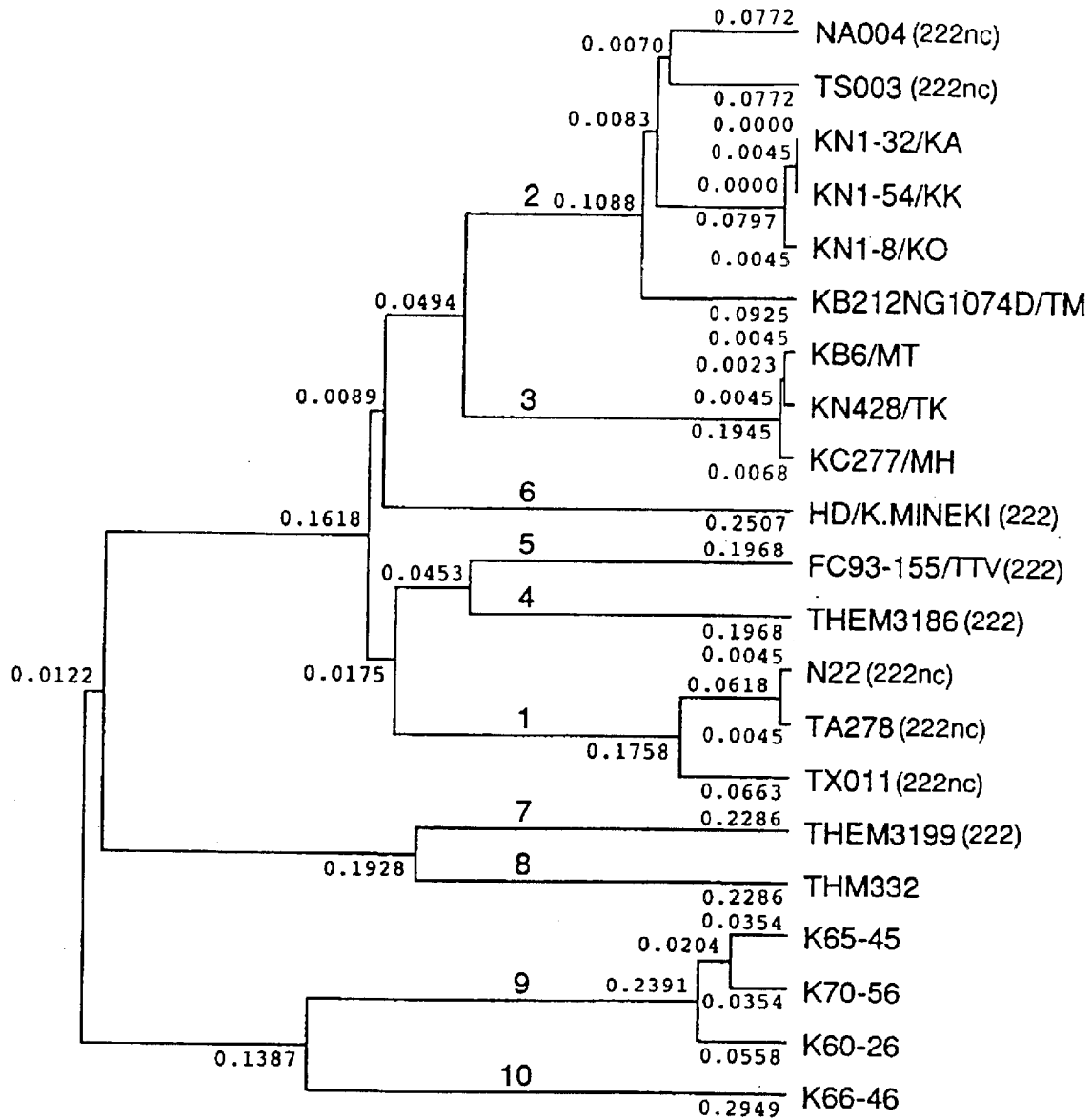

FIG. 10 represents a molecular phylogenetic tree based on the nucleotide sequences of the genes from HNT22 positive cases obtained in Example 12.

Figure 11:
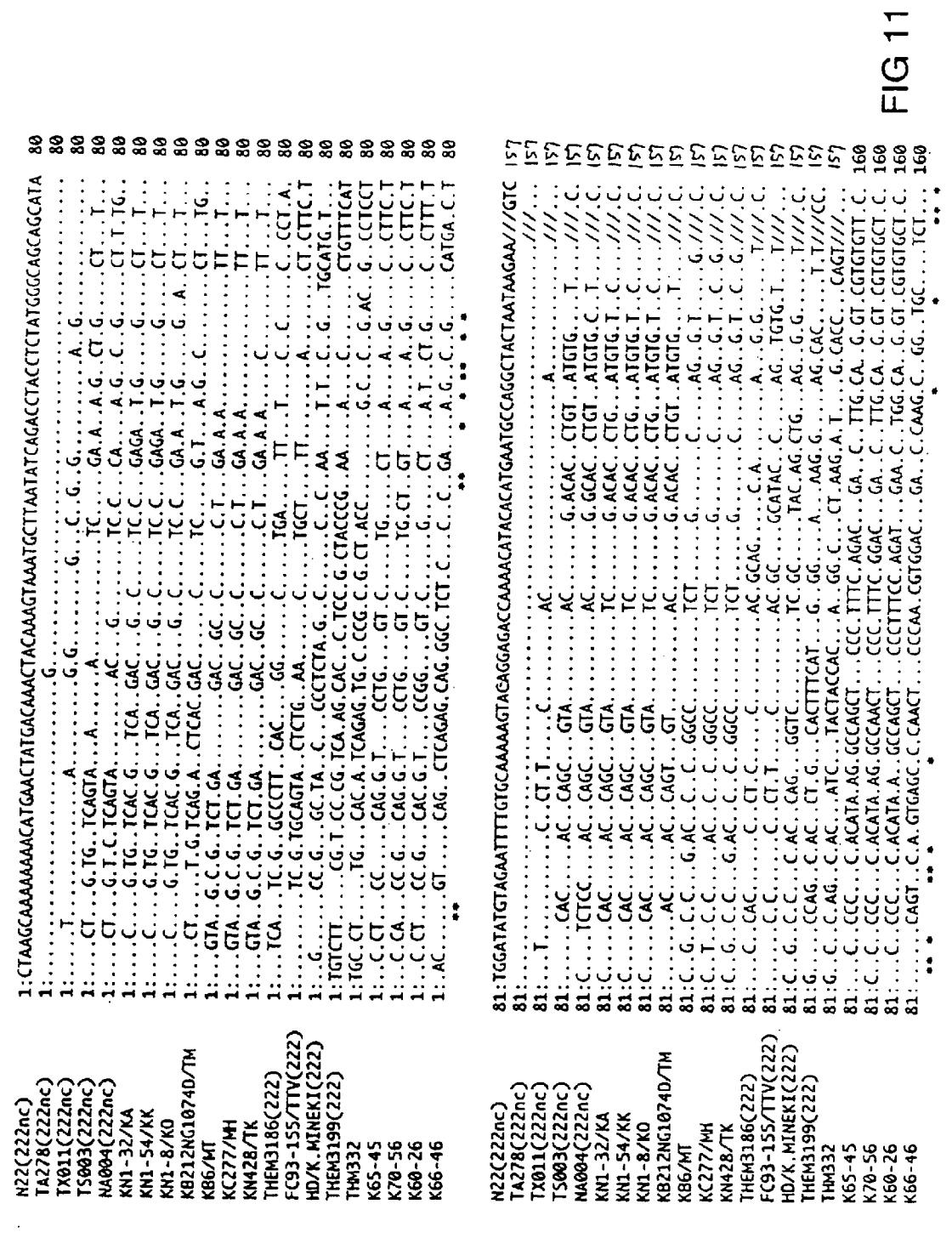

FIGS. 11 and 12 represent comparison of nucleotide sequences of the genes from HNT22 positive cases obtained in Example 12.

Figure 13:
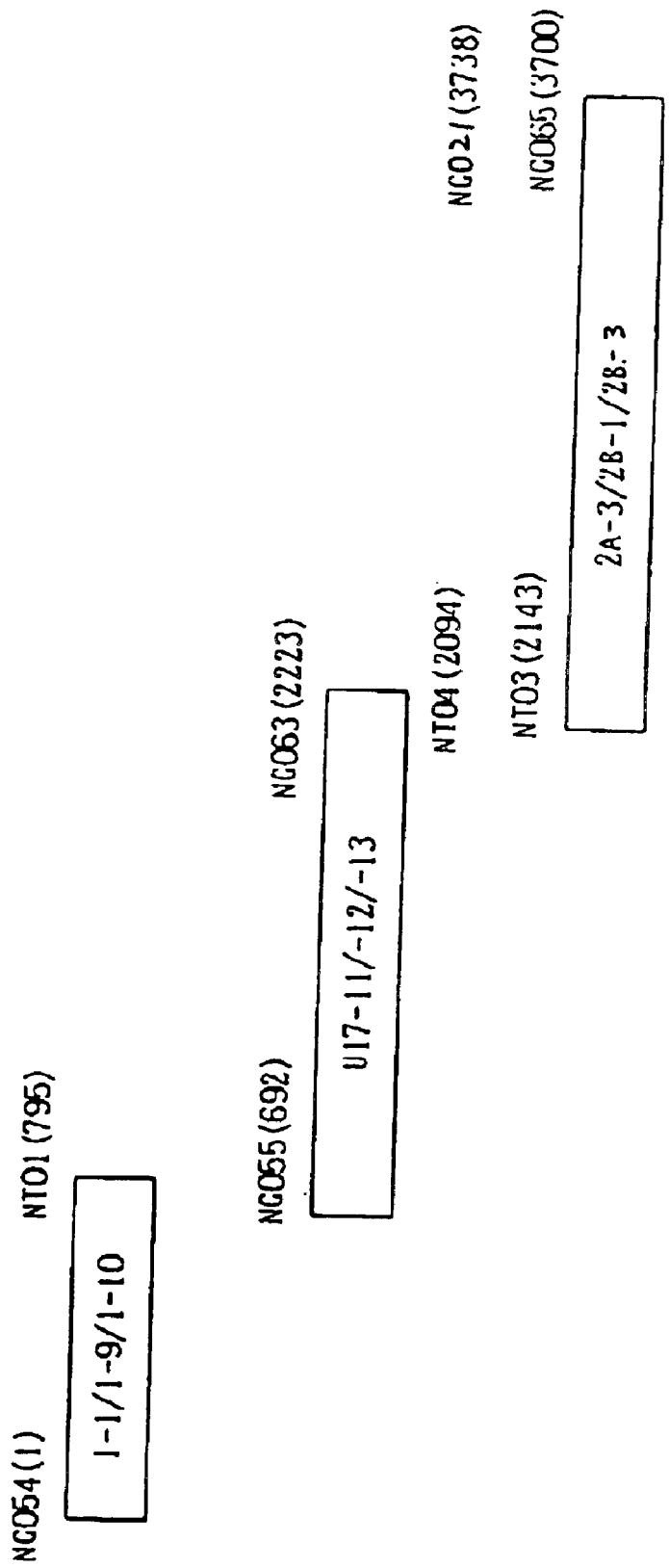

FIG. 13 represents locational relation of the primers and the clones used for the sequencing of the full length TUS01 gene. Names of the clones whose sequences were determined are indicated in the boxes. Names of the primers used for the amplification are indicated on the left and right tops of the boxes, and nucleotide numbers when the first nucleotide of the 5' end is defined as nucleotide 1 are indicated in parentheses.

FIG. 14 represents the results of searching of open reading frame (ORF) of the TUS01 gene.

FIG. 15 represents comparison of 5' end region sequences of the HNT22 gene and the TUS01 gene.

Figure 16:
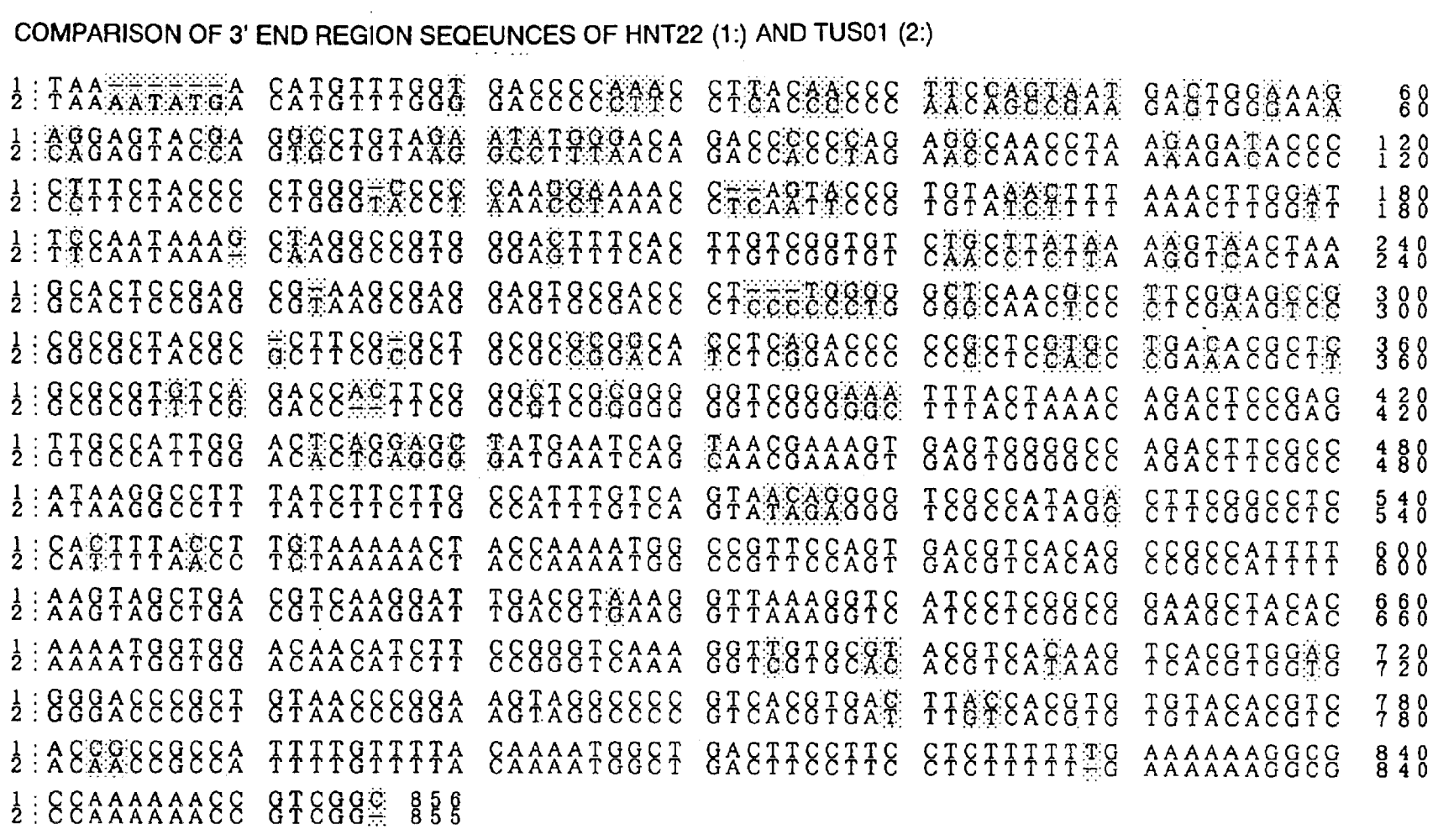

FIG. 16 represents comparison of 3' end region sequences of the HNT22 gene and the TUS01 gene.

BEST MODE FOR CARRYING OUT THE INVENTION

The present invention will be explained in detail hereinafter with reference to the following examples, but of course the present invention is not limited to these examples.

Example 1

Isolation of Clone #22

For 3 cases clinically confirmed as post-transfusion hepatitis of non-A, non-B, non-C, non-D, non-G (Cases 1–3), genes present only in blood samples of the patients after crisis of post-transfusion hepatitis by the RDA method (subtraction) using blood of the patients upon or after the crisis of post-transfusion hepatitis and blood of the same patients before blood transfusion or before the crisis as samples. The RDA method is a method for detecting genes present only one part of comparison groups as described above, and it is a method for efficiently searching genes different between a tester which is a sample, and a driver which is a control.

In this example, a sample after crisis of hepatitis of Case 2 among the above-mentioned three cases clinically diagnosed as post-transfusion hepatitis whose cause was indistinct (see Example 6 for details) were used as a tester (A), and a sample of the same case before hepatitis crisis after blood transfusion (B1) and a sample of other acute hepatitis B patients (B2) were used as drivers, and genes which had first appeared in the blood of the patient after crisis of post-transfusion hepatitis were discovered.

The procedure will be explained in detail hereinafter.

(1) Extraction of Nucleic Acids

The above post-transfusion hepatitis case (Case 2) was negative for any of known hepatitis virus markers. Its blood serum (mixture of 50 µl each of blood sera eight weeks and ten weeks after the blood transfusion of Case 2) was used as an unknown hepatitis virus positive tester (A).

As controls negative for the unknown virus, blood serum of the same patient from who (A) was obtained but before the crisis of hepatitis (two weeks after the blood infusion, B1), and serum of another patient of acute hepatitis B (B2) were used as drivers. First, nucleic acids were extracted from 100 µl each of the sera of the tester and drivers by using a commercially available kit for nucleic acid extraction (ISOGEN-LS, Nippon Gene). That is, each serum (100 µl) and a nucleic acid extraction solution (300 µl) were taken into a 1.5-ml Eppendorf tube, stirred for mixing for one minute, and left at room temperature for 5 minutes. After the mixture remained on the wall of the tube was fallen by centrifugation, the mixture was added with chloroform (80 µl), stirred for one minute, and left at room temperature for 5 minutes. After the reaction was completed, the mixture was subjected to centrifugation for 15 minutes at 12000 revolutions/minute to afford a supernatant. The supernatant (210 µl) was taken in another Eppendorf tube, added with glycogen (20 mg/ml, 1 µl, Boehringer Mannheim) and isopropanol (200 µl, Wako Pure Chemicals Industries), and mixed. After the mixture was left at room temperature for 10 minutes for reaction, it was subjected to refrigerated centrifugation at 12000 revolutions/minute (4° C.) for 10 minutes to afford precipitates, which was washed with 70% ethanol (Wako Pure Chemicals Industries) and dried in air.

(2) Synthesis of cDNA

The nucleic acid obtained by the above procedure was dissolved in DEPC-water (10 µl, deionized water treated with diethyl pyrocarbonate, Sigma). This solution was added with a randomized hexamer solution (50 ng/µl, 1 µl), warmed at 70° C. for 5 minutes, and then promptly ice cooled. After the cooling, a first strand buffer at 5-fold concentration (4 µl), 0.1 M DTT (2 µl), 10 mM dNTP (1 µl), RNase inhibitor (1 µl, 40 U/µl, RNasin, PROMEGA), and reverse transcriptase (1 µl, 200 U/µl, SuperScript II, GIBCO-BRL) were added to the solution, and allowed to react at 37° C. for 60 minutes for synthesis of cDNA of the first strand. Then, to a tube containing the cDNA, DEPC-water (91 µl), a second strand buffer at 5-fold concentration (30 µl), 10 mM dNTP (3 µl), E. coli DNA ligase (1 µl, 10 U/µl), E. coli DNA polymerase (4 µl, 10 U/µl), and E. coli RNaseH (1 µl, 20 U/µl) were added and mixed, and allowed to react at 16° C. for two hours. Then, the reaction mixture was added with T4 DNA polymerase (2 µl, 5 U/µl), and allowed to react at 16° C. for 5 minutes to synthesize second strand cDNA. The reaction was stopped by adding EDTA (5 µl, 0.5 M). Subsequently, a mixture of phenol and chloroform (150 µl, 1:1) was added to the mixture in the tube and mixed, and subjected to centrifugation at 15000 revolutions/minute at room temperature for 5 minutes to separate proteins as precipitates. The obtained supernatant (156 µl) was added with glycogen (1 µl, 20 mg/ml), 7.5 M ammonium acetate (78 µl, Wako Pure Chemicals Industries), and cold ethanol (562 µl, Wako Pure Chemicals Industries), and immediately centrifuged at 15000 revolutions/minute at room temperature for 20 minutes to afford nucleic acids as precipitation fraction. The precipitates were washed with cold 70% ethanol (600 µl), dried in air, and then dissolved in TE buffer (50 µl, 10 mM Tris-HCl, pH 7.5, 1 mM EDTA). The solution was then subjected to gel filtration using Microspin S-400 HR Column (Pharmacia). The obtained eluent (50 µl) was added with 1/10 volume of 3M sodium acetate (pH 5.2) and 2.5 volumes of ethanol, left stand at −80° C. for 20 minutes, and centrifuged at 15000 revolutions/minute at 4° C. for 20 minutes to collect a cDNA/DNA fraction as precipitates.

(3) Sau3AI Digestion

The cDNA/DNA fraction collected by the above procedure was dissolved in water (45 µl), added with H buffer at 10-fold concentration (5 µl, buffer attached to the restriction endonuclease Sau3AI, Takara Shuzo), and Sau3AI (4 µl, 12 U/µl, Takara Shuzo) and mixed, and allowed to reacted at 37° C. for 1.5 hours. After the reaction was completed, the reaction mixture was added with a mixture of phenol and chloroform (40 µl, 1:1), stirred, and subjected to centrifugation at 15000 revolutions/minute at room temperature for 15 minutes. The supernatant (60 µl) was added with 1/10 volume of 3 M ammonium acetate, pH 5.2 and 2.5 volumes of ethanol, left stand at −80° C. for 20 minutes, and subjected to centrifugation at 15000 revolutions/minute at 4° C. for 20 minutes to collect nucleic acids as precipitates.

(4) Ligation of Adapter

Adapters were introduced into the both ends of the fragments by ligating adapters R-Bam24 and R-Bam12 that were compatible with the nucleotide sequences of the ends cleaved with the restriction enzyme Sau3AI. That is, the nucleic acid fraction precipitates obtained by the above procedure was dissolved in water (16.1 µl), and added with a T4 ligase buffer at 10-fold concentration (3 µl, NEB), the adapter R-Bam24 (6.0 µl, 10 OD/ml), and the adapter R-Bam12 (3.0 µl, 10 OD/ml), then the ambient temperature was lowered from 50° C. to 10° C. over one hour, and the mixture was added with T4 ligase (1.5 µl, 400 U/µl, NEB), and allowed to react at 16° C. overnight.

(5) PCR Amplification

Then, the gene fragments were treated with DNA polymerase to obtain gene fragments which were completely double-stranded over the full length, and these gene fragments were amplified by PCR using R-Bam24 as primer as follows. The nucleic acid fraction introduced with the adapters by the above procedure was warmed at 70° C. for 15 minutes to inactivate the T4 ligase in the reaction mixture. Then, TaKaRa EX Taq Polymerase buffer at 10-fold concentration (20 µl, Takara Shuzo), 2.5 mM dNTP (24 µl), water (149.3 µl), and R-Bam24 (5.2 µl, 10 OD/ml) were added to the mixture, and allowed to react at 70° C. for three minutes, and then TaKaRa EX Taq Polymerase (1 µl) was added to perform PCR with the following conditions. That is, after treatment at 72° C. for 5 minutes, a cycle of 95° C. for 1 minute and 72° C. for 3 minutes was repeated for 30 cycles, followed by treatment at 72° C. for 7 minutes and cooling to 4° C. After the completion of the reaction, nucleic acids were extracted with phenol and chloroform in the same manner as described above, and precipitated with ethanol. The precipitates of the PCR products obtained from eight tubes were combined and dissolved in TE buffer (100 µl), and subjected to gel filtration in the same manner as described above to afford an eluted solution, which was subjected to precipitation with ethanol.

(6) Removal of Adapter

The PCR products precipitated with ethanol after the gel filtration were dissolved in water (90 µl). To this solution was added H buffer at 10-fold concentration (10 µl) and then Sau3AI (7 µl), and allowed to react at 37° C. for 15 minutes. Then, the nucleic acids were collected as precipitates in the same manner as described above, then subjected to gel filtration using MicroSpin S-400 HR Column as described above, and precipitated with ethanol and collected. The product was dissolved again, and its absorbance at 260 nm was measured to confirm the yield.

(7) Ligation of Adapter (J-Bam24/J-Bam12) to Tester

Then, the adapters J-Bam24 and J-Bam12 which are compatible with Sau3AI sequence were connected only to the tester amplified gene fragments as follows. That is, among the amplification products whose R-Bam24 and R-Bam12 tester were removed, those derived from the tester were added with T4 ligase buffer at 10-fold concentration (3 µl per 1.0 µg of the PCR products), and further added with the adapters J-Bam24 (13.2 µl) and J-Bam12 (6.6 µl) and water (4.9 µl). The ambient temperature was lowered from 50° C. to 10° C. over one hour to anneal them. To this reaction mixture, T4 DNA ligase (400 U/µl, NEB, 1.0 µl) was added, and allowed to react at 16° C. overnight to ligate the adapters to the Sau3AI cleaved ends. Then, the mixture was treated at 70° C. for ten minutes to inactivate the ligase.

(8) Hybridization of Tester Amplified Gene Fragments with Adapter and Driver Amplified Gene Fragments without Adapter The amplification products derived from the tester to which adapters were connected and the amplification products derived from the drivers of which adapters were removed by the procedure described were denatured by heat, thereby completely made into single-stranded DNA, and then re-associated as follows. First, a mixture of phenol and chloroform (1:1, 30 µl) was added to the reaction mixture to remove proteins. To the obtained supernatant (17 µl), a driver gene amplification product whose adapters were removed (40 µg) was added, and precipitated with ethanol. The precipitates were added with EE buffer at 3-fold concentration (4 µl) and dissolved therein, and overlaid with mineral oil (30 µl, Sigma), and the DNA was denatured by a treatment at 98° C. for ten minutes. After the denaturation, the mixture was immediately cooled with ice, and added with 5 M sodium chloride (Wako Pure Chemicals Industries, 1 µl). Then, hybridization was performed at 67° C. for about 22 hours.

During the above procedure, for genes commonly present in the tester and the drivers, like genes derived from human, original combinations of DNA, i.e., double-stranded DNA composed of re-associated two DNA strands derived from the tester, or two DNA strands derived from the driver (homo-double-stranded DNA), and double-stranded DNA composed of one DNA strand derived from the tester and one DNA strand derived from the driver (hetero-double-stranded DNA) were formed. In contrast, for DNA present only in the tester (considered to be an exogenous gene), hetero-double-stranded DNA was not formed and only homo-double-stranded DNA derived from the tester was formed because the corresponding allogeneic gene was not present in the driver. Further, only the double-stranded DNA having a gene sequence derived from the tester had the adapter sequences in both of the strands.

(9) Amplification

A sample undergone the hybridization in the above procedure was added with water (15 µl), and then nucleic acids in the sample were precipitated with ethanol in the same manner as described above. The precipitates were added with ½ TE buffer (20 µl, 5 mM Tris-HCl, pH 7.5, 0.5 mM EDTA), and dissolved therein. To this solution (2 µl), Ex Taq Polymerase buffer at 10-fold concentration (20 µl), 2.5 mM dNTP (240 µl), water (147.7 µl), and TaKaRa EX Taq polymerase (1 µl) were added, and allowed to react at 72° C. for 5 minutes. During this reaction, DNA was synthesized for the portions remained as a single strand in the double-stranded DNA formed in the above operation, and terminuses were blunt-ended. This sample was added with J-Bam-24 (5.3 µl, 10 OD/ml) as a primer, and PCR was performed by 10 cycles of a cycle of 95° C. for 1 minute and 70° C. for 3 minutes, and leaving the mixture at 70° C. for 7 minutes and then at 4° C. Nucleic acids were extracted from the amplified sample in the same manner as described above by using a mixture of phenol and chloroform, and precipitated with ethanol by using glycogen as a coprecipitating agent. Under this condition, only the genes derived from the tester to which the J-Bam24 was ligated as adapter can be amplified by utilizing the added J-Bam24 as a primer. As a result, DNA derived from the homo-double-stranded DNA of the tester specific genes can be amplified for the both DNA strands, and hence exponentially amplified. On the other hand, the hetero-double-stranded DNA constituted by the genes common to the tester and the driver is amplified just multiplicatively only for the DNA strand having the driver gene sequence of which template is the tester. The DNA strands derived from the homo-double-stranded DNA composed only of the driver genes cannot be amplified because the added primer cannot hybridize to them. Accordingly, the homo-double-stranded DNA having the tester specific gene sequences becomes predominant in the reaction mixture after the amplification.

(10) Mung Bean Nuclease Treatment

In order to obtain only tester specific genes except for single strand driver gene sequence DNA present in the reaction mixture (precisely, a few double-stranded DNA derived from the driver will remain), mung bean nuclease (abbreviate as "MBN" hereinafter) treatment was performed as follows. Nucleic acid fractions obtained by precipitating from hybridization samples of the tester A and the driver B1, or the tester A and the driver B2 were each added with TE buffer of a ½ concentration (10 µl) and dissolved therein. 5 µl was taken from each solution, added with MBN buffer at 10-fold concentration (2 µl), water (13 µl), and MBN (0.5 µl, 300 U/µl, Takara Shuzo), and allowed to react at 37° C. for 30 minutes. After the completion of the reaction, 50 mM Tris-HCl, pH 8.9 (80 µl) was added to the reaction mixtures and allowed to react at 95° C. for 5 minutes to inactivate the nuclease. Aliquots of 5 µl and 10 µl taken from the above reaction mixtures, and the above hybridization sample not subjected to the nuclease treatment (1 µl) were each added with Ex Taq Polymerase buffer at 10-fold concentration (20 µl), 2.5 mM dNTP (24 µl), the primer J-Bam24 and TaKaRa Ex Taq DNA Polymerase (1 µl), and further added with water to a total volume of 200 µl, and PCR was performed with the following condition. Namely, a reaction cycle of 95° C. for 1 minute and 70° C. for 3 minutes was repeated for 20 times, followed by treatment at 70° C. for 7 minutes and cooling to 4° C. 10 µl was taken from the PCR products, and subjected to gel electrophoresis (1× TBE buffer) on 2.5% NuSieve 3:1 agarose (FMC BioProducts, USA). Since the results were the same for the combination of A and B1 and the combination of A and B2, only the combination of A and B1 will be described hereinafter.

Nucleic acids were extracted from the remained amplification products by the extraction method mentioned above using a mixture of phenol and chloroform, precipitated with ethanol, and collected. The precipitates were added with TE buffer (45 µl) and dissolved therein. This solution was subjected to gel filtration using MicroSpin S-400 HR Column mentioned above, and the eluted solution was subjected to ethanol precipitation.

(11) Removal of Adapter

The precipitates obtained above were dissolved in water (63 µl), added with H buffer at 10-fold concentration (7 µl) and Sau3AI (6 µl, 12 U/µl), and allowed to react at 37° C. for 1.5 hours to cleave the J-Bam24 and J-Bam12 adapter moieties. Proteins were removed from the reaction mixture by using a mixture of phenol and chloroform as described above, and nucleic acids were precipitated with ethanol. The precipitates were dissolved in TE buffer (90 µl), and subjected to gel filtration using MicroSpin S-400 HR Column to remove the cleaved adapters. The eluted solution, which contained the amplification products whose adapters were removed, was precipitated with ethanol, and the precipitates were dissolved in TE buffer at ½ concentration (10 µl, 5 mM Tris-HCl, pH 7.5, 0.5 mM EDTA). Absorbance at 260 nm of this solution was measured to determine the yield. It was thought that tester specific genes were contained in this fraction.

(12) Re-subtraction

The candidate DNA fraction (1 µg) of the tester specific genes obtained in the above procedure was added with T4 DNA ligase buffer at 10-fold concentration (3 µl), adapters N-Bam24 (13.2 µl), and N-Bam12 (6.6 µl), and filled up to a total volume of 28.5 µl, and then its temperature was lowered from 50° C. to 10° C. over one hour. Then, the mixture was added with T4 DNA ligase (1.5 µl, 400 U/µl), and allowed to react at 16° C. overnight to ligate the adapters. Then, the mixture was treated at 70° C. for 10 minutes to inactivate the T4 DNA ligase, and after removing proteins in a conventional manner using a mixture of phenol and chloroform, subjected to precipitation with ethanol. The supernatant (17 µl, about 0.5 µg as DNA) was added with driver B1 DNA (40 µg) and mixed, and then precipitated with ethanol. The precipitates were added with TE buffer at 3-fold concentration (4 µl) and dissolved therein, overlaid with mineral oil (30 µl, Sigma), and heat-treated at 98° C. for one minute to denature the DNA. After the denaturation, the mixture was immediately cooled with ice, and added with 5 M sodium chloride (1 µl, Wako Pure Chemicals Industries) to perform hybridization at 67° C. for about 21 hours. From the sample after the hybridization, nucleic acids were precipitated with ethanol in the same manner as described above. The precipitates were added with TE buffer of ½ concentration (20 µl) and dissolved therein, and to 2 µl of this solution was added EX Taq DNA polymerase buffer at 10-fold concentration (20 µl), 2.5 mM dNTP (240 µl), water (147 µl), and TaKaRa Ex Taq DNA polymerase (1 µl), and allowed to react at 72° C. for 5 minutes so that the nucleic acid should be blunt-ended. This sample was added with N-Bam24 (5.3 µl, 10 OD/ml) as a primer, and PCR was performed with the condition that a cycle of 95° C. for 3 minute and 70° C. for 3 minutes was repeated for 10 cycles, and the mixture was left at 70° C. for 7 minutes and then at 4° C. From the amplified sample, nucleic acids were extracted in the same manner as described above using a mixture of phenol and chloroform, added with glycogen, and precipitated with ethanol. This nucleic acid fraction was added with TE buffer of ½ concentration (10 µl), and dissolved therein. 1 µl was taken from the solution, and added with TaKaRa Ex Taq DNA polymerase at 10-fold concentration (1 µl), and PCR was performed with the condition that a cycle of 95° C. for 1 minute and 70° C. for 3 minutes was repeated for 20 cycles, followed by treatment at 70° C. for 7 minutes and cooling to 4° C. By the above procedure, the tester specific genes were further screened. The adapters were removed again from the DNA fraction obtained from this procedure, and the same procedure was repeated once more utilizing J-Bam24 and J-Bam12 as adapters to afford final candidates of the tester specific gene, Clone #22.

(13) Isolation of Clone #22

The nucleotide sequences of the tester specific gene candidates obtained by the above procedure were determined as follows to isolate novel viral gene Clone #22. The #22 has Sau3AI cleaved sequences at the both ends. By utilizing these sequences, it was cloned into pT7BlueT vector (Navagen). This clone was transfected into E. coli TG-1, and transformant cells were screened. The plasmid DNA of the obtained transformants were analyzed. That is, for 60 clones in total, plasmid DNAs were prepared, and their nucleotide sequences were determined in the original direction and the reverse direction by using Thermo Sequencer Fluorescent-labelled primer cycle sequencing kit (Amersham International plc. Buckinghamshire, England). Based on these sequences, the clones were classified. As a result, 13 clones having the same nucleotide sequence were obtained. Consensus sequence was searched by aligning the sequences of these clones, and the sequence shown in SEQ ID NO: 11 was obtained. The clone having this sequence was designated as Clone #22. The full length of Clone #22 was 500-nucleotide length.

Example 2

HNT22 Gene Detection Method (1)

A plurality of oligonucleotides of 20-nucleotide length constituting the nucleotide sequence of HNT22 Clone #22 obtained in Example 1 were produced, and various combinations thereof were examined for their utility as primers for gene amplification. That is, PCR was performed for samples which were positive for the genes and from which the genes were isolated in order to search sequences and combinations thereof capable of efficiently amplifying the genes. As a result, it was found that oligonucleotides having the sequences shown in SEQ ID NO: 2 (primer name: RD037) and SEQ ID NO: 3 (primer name: RD038) as well as oligonucleotides having the sequences shown in SEQ ID NO: 4 (RD051) and SEQ ID NO: 5 (RD052) could be effectively used as primers for gene amplification. RD037 and RD051 are sense primers, and RD038 and RD052 are anti-sense primers. Amplification is performed by using a pair of sense primer and anti-sense primer.

The details of the method used for detecting genes are as follows.

Nucleic acids were extracted from blood serum or plasma (100 μl) using a commercially available nucleic acid extraction kit (EX R&D, Sumitomo Metal Industries). Because it had been revealed that HNT22 virus is a DNA virus as described hereinafter (Example 8), viral genes were treated as DNA in this procedure. The extracted DNA was dissolved in TE buffer (10 μl), and the whole volume was used as a sample. AmpliTaq DNA polymerase buffer at 10-fold concentration (5.0 μl, Perkin Elmer), 10 mM dNTP (1.0 μl), primers RD037 and RD038 (0.5 μl for each, 10 OD/ml), and thermostable DNA polymerase (0.25 μl, AmpliTaq DNA Polymerase, Perkin Elmer) were introduced into a tube exclusively for PCR, and added with distilled water to a total volume of 50 μl. This reaction mixture was prepared upon use.

To the tube containing the reaction mixture, the above extracted DNA sample (10 μl) was added, overlaid with mineral oil (50 μl), stirred, and then centrifuged in a refrigerated centrifugal separator at 6000 rpm for 30 seconds. After the centrifugation, the tube was mounted on a thermal cycler, and PCR was performed. PCR was performed with a treatment at 95° C. for 2 minutes and 30 seconds, then a cycle of 94° C. for 30 seconds, 55° C. for 30 seconds, and 72° C. for 45 seconds for 35 cycles, and a treatment at 72° C. for 7 minutes after the last cycle.

When further amplification was performed, AmpliTaq DNA polymerase buffer at 10-fold concentration (5.0 μl, Perkin Elmer), 10 mM dNTP (1.0 μl), primers RD051 and RD052 (0.5 μl for each, 10 OD/ml) that were selected from a nucleotide sequence located more interior than the aforementioned RD037 and RD038, and thermostable DNA polymerase (0.25 μl, AmpliTaq DNA Polymerase, Perkin Elmer) were introduced into another tube exclusively for PCR, and further added with distilled water (37.5 μl) to a total volume of about 45 μl. To this mixture, the aforementioned amplification product (5 μl) was added to afford a reaction mixture. This reaction mixture was prepared upon use.

After the preparation of the reaction mixture, the mixture was overlaid with mineral oil (50 μl), mixed, and then centrifuged in a refrigerated centrifugal separator at 6000 rpm for 30 seconds. Then, the tube was mounted on a thermal cycler, and PCR was performed. PCR was performed with a cycle of 94° C. for 30 seconds, 55° C. for 30 seconds, and 72° C. for 30 seconds for 25 cycles, and a treatment at 72° C. for 7 minutes after the last cycle.

The amplified genes were detected by electrophoresis. That is, 10 μl of the amplification product obtained by the amplification with the above condition was taken, and subjected to agarose gel electrophoresis (2.5% NuSieve: Agarose EP=3:1). The agarose gel after the electrophoresis was stained with ethidium bromide, and presence or absence of the amplification product was confirmed under ultraviolet light. The amplification product could be detected as a band at 270 bp when only the primers RD037 and RD038 were used, or as a band at 197 bp when the amplification was performed by using the primers RD051 and RD052 once or with additional amplification.

Example 3

HNT22 Gene Detection Method (2)

While HNT22 viral infection cases in Japanese patients could be sufficiently detected by the HNT22 gene detection method of Example 2, in order to further examine conservation of the amplified region, sequences within the range containing the region of a large number of samples were amplified by the method using primers NG001/RD038 (1st PCR) and NG001/RD052 (2nd PCR) described hereinafter in Example 7, and examined. As a result, it was found that a plurality of genotypes including the two major Genotypes I and II (designations decided by the present inventors as described in Example 12 hereinafter) exist for HNT22 virus. It was further found that mismatches are scattered in the sequences of the primers RD037 and RD051, in particular at the 3' end side, in the genotype designated as Genotype II (FIG. 1 to FIG. 5). Based on an assumption that more specific and more sensitive gene detection methods can be developed by avoiding this mismatch sequence, further highly conserved sequences were searched. As a result, it was found that oligonucleotides having the sequences shown in SEQ ID NO: 6 (primer name: NG059), SEQ ID NO: 7 (NG061), and SEQ ID NO: 8 (NG063) can be utilized as primers for gene amplification (FIG. 1 to FIG. 5), and novel HNT22 gene detection methods utilizing them have been completed.

The details of the method used for detecting genes are as follows.

DNA was extracted from blood serum or plasma (50 µl) in the same manner as in Example 2. The extracted DNA was dissolved in distilled water (20 µl), treated at 95° C. for 15 minutes, and immediately cooled in ice for 2 minutes to afford a sample for measurement. AmpliTaq DNA polymerase buffer at 10-fold concentration (5.0 µl, Perkin Elmer), 2.5 mM dNTP (4 µl), primers NG059 and NG063 (0.5 µl for each, 10 OD/ml), and thermostable DNA polymerase (0.25 µl, AmpliTaq DNA Polymerase, Perkin Elmer) were introduced into a tube exclusively for PCR, and further added with distilled water (29.75 µl) to a total volume of 40 µl. To the tube containing the reaction mixture, the extracted DNA sample (10 µl) was added, overlaid with mineral oil (50 µl), stirred, and then centrifuged in a refrigerated centrifugal separator at 6000 rpm for 30 seconds. After the centrifugation, the tube was mounted on a thermal cycler, and PCR was performed. PCR was performed with a cycle of 94° C. for 30 seconds, 60° C. for 45 seconds, and 72° C. for 45 seconds for 35 cycles, and finished with a reaction at 72° C. for 7 minutes after the last cycle.

When further amplification was performed, AmpliTaq DNA polymerase buffer at 10-fold concentration (5.0 µl, Perkin Elmer), 2.5 mM dNTP (4 µl), primers NG061 and NG063 (0.5 µl for each, 10 OD/ml), and thermostable DNA polymerase (0.25 µl, AmpliTaq DNA Polymerase, Perkin Elmer) were introduced into another tube exclusively for PCR, and further added with distilled water (37.75 µl) to a total volume of 48 µl. To this mixture, the aforementioned amplification sample (2 µl) was added, and the mixture was overlaid with mineral oil (50 µl), stirred, and then centrifuged in a refrigerated centrifugal separator at 6000 rpm for 30 seconds. Then, the tube was mounted on a thermal cycler, and PCR was performed. PCR was performed with a cycle of 94° C. for 30 seconds, 60° C. for 45 seconds, and 72° C. for 45 seconds for 25 cycles, and finished with a reaction at 72° C. for 7 minutes after the last cycle. The amplified genes were detected by agarose gel electrophoresis in the same manner as in Example 2. In this example, the HNT genes could be detected as a band at 286 bp when amplified by PCR using the first primers NG059 and NG063, or as a band at 271 bp when amplified by PCR using the primers NG061 and NG063.

Each PCR constituting the two-step PCR performed in this example may of course be performed alone.

Further, because the gene detection method of Example 3 can be utilized for amplification of many different genes of the HNT22 gene including Genotypes I and II, and amplification specific for Genotype 1 can be realized by the gene amplification method of Example 2, it is possible to classify samples for their genotypes by subjecting each one sample to gene detection according to Example 2 and Example 3, and examining resulting detection patterns (FIG. 1 to FIG. 5).

Example 4

Extension of Identified Gene Sequence

An identified gene sequence was extended based on Clone #22. That is, by using a sample (serum) of a blood donor exhibiting abnormality of hepatic function (34 years old, male, ALT [alanine aminotransferase] value: 106 IU), which sample showed high HNT22 virus titer (HNT22 genes could be detected even in $10^{4-5}$-fold dilution) as determined by the two-step PCR consisting of a combination of PCR utilizing the primer pair of RD037 and RD038 and PCR utilizing the primer pair of RD051 and RD052, and the two-step PCR consisting of a combination of PCR utilizing the primer pair of NG059 and NG063 and PCR utilizing the primer pair of NG061 and NG063, which were established in Examples 2 and 3, the #22 sequence was extended in the 5' direction and the 3' direction by the walking technique. The virus strain having the obtained nucleotide sequence (SEQ ID NO: 1) was designated as T278.

The details of the walking method performed in this example were as follows (FIG. 6).

(1) Sequencing of Clones T4 and T6

Two-step single-sided PCR was performed using sense and anti-sense primers specific for the nucleotide sequence of Clone #22 and non-specific primers which had nucleotide sequences of 41-nucleotide length shown in SEQ ID NOS: 12–15 (SSP-G, SSP-A, SSP-T and SSP-C).

For the extension of the 5' end, two-step single-sided PCR utilizing a combination of either of specific anti-sense primer RD038 or RD052 and one of the above-mentioned non-specific primers was performed. In the PCR of the first step (1st PCR), a cycle of 94° C. for 30 seconds, 42° C. for 45 seconds, and 72° C. for 2 minutes was repeated 5 times, the reaction products were purified by SizeSep-400 Column (Pharmacia Biotechnology), and a cycle of 94° C. for 30 seconds, 55° C. for 45 seconds, and 72° C. for 2 minutes was repeated 35 times for amplification. In the PCR of the second step (2nd PCR), 1/10 volume of the product of the 1st PCR was used, and a cycle of 94° C. for 30 seconds, 55° C. for 30 seconds, and 72° C. for 2 minutes was repeated 30 times. PCR was performed by using TaKaRa Ex Taq DNA Polymerase (Takara Shuzo). The product was cloned into pT7Blue T vector in the same manner as in Example 1, and nucleotide sequences of the both strands were determined for three or more clones to obtain the sequence shown in SEQ ID NO: 16 (corresponding to nt1455–2257 shown in SEQ ID NO: 1, Clone T4), and the sequence shown in SEQ ID NO: 17 (corresponding to nt2061–3265 of SEQ ID NO: 1, Clone T6). The sequence shown in SEQ ID NO: 16 was obtained from amplification product of PCR utilizing the combination of the primers SSP-A and RD052, and the sequence shown in SEQ ID NO: 17 was obtained from amplification product of PCR utilizing the combination of the primers RD051 and SSP-C.

(2) Sequencing of Clones T7, T9, T11, and T13

Using the newly identified Clones T6 and T4, the 5' nucleotide sequence was identified from Clone T4 and the 3' nucleotide sequence form Clone T6 in the same manner as in the above (1). That is, for the 5' sequence, two-step single-sided PCR was performed by using specific anti-sense primers which have the sequences of SEQ ID NOS: 18 and 19 having a sequence specific for the 5' end of Clone T4 (NG012 and NG013) and non-specific primers which have the nucleotide sequences of SEQ ID NOS: 12–15 and 20, resulting amplification products were cloned, and sequenced by the method described in Example 1. Specifically, PCR of the first step was performed by using a combination of the anti-sense primer NG012 and any one of the aforementioned non-specific primers. For PCR, a cycle of 94° C. for 30 seconds, 55° C. for 30 seconds, and 72° C. for 2 minutes was repeated 5 times, the reaction products were purified by SizeSep-400 Column (Pharmacia Biotechnology), and a reaction cycle of 94° C. for 30 seconds, 55° C. for 45 seconds, and 72° C. for 2 minutes was further repeated 35 times. The PCR of the second step was performed by using 1/10 volume of the product of the PCR of the first step and NG013 as the specific anti-sense primer, and repeating a cycle of 94° C. for 30 seconds, 55° C. for 30 seconds, and 72° C. for 2 minutes 30 times. The amplification product was cloned into pT7Blue T vector in the same manner as in Example 1, and nucleotide sequences of the both strands were determined for three or more clones to obtain the sequence shown in SEQ ID NO: 21 (corresponding to nt945–1575 in SEQ ID NO: 1, Clone T9) (FIG. 6).

For the 3' sequence, sequence amplification by utilizing two-step single-sided PCR similar to the above one using specific sense primers NG006 and NG010 which have the sequences of SEQ ID NOS: 22 and 23 having a sequence specific for the 3' end of Clone T6 and non-specific primers which have the nucleotide sequences of SEQ ID NOS: 12–15 and 20, cloning into pT7blue T vector, and sequence analyses were performed to afford the sequence shown in SEQ ID NO: 24 (corresponding to nt3126–3739 in SEQ ID NO: 1, Clone T7) (FIG. 6).

For the 5' sequence, the same procedure was further repeated to obtain the sequence shown in SEQ ID NO: 25 (corresponding to nt723–1024 of SEQ ID NO: 1, Clone T11) by using the sequence of the aforementioned Clone T9, and the sequence shown in SEQ ID NO: 26 (corresponding to nt1–831 shown in SEQ ID NO: 1, Clone T13) by using the sequence of Clone T11. By aligning the sequences of these clones, the sequence of HNT22 shown in SEQ ID NO: 1 was obtained. In order to obtain Clone T11, an oligonucleotide having the nucleotide sequence shown in SEQ ID NO: 27 (primer name: NG031) was used as an as anti-sense primer for the single-sided PCR of the first step, and an oligonucleotide having the nucleotide sequence shown in SEQ ID NO: 28 (primer name: NG032) was used as an as anti-sense primer for the single-sided PCR of the second step. In order to obtain Clone T13, an oligonucleotide having the nucleotide sequence shown in SEQ ID NO: 29 (primer name: NG045) was used as an as anti-sense primer for the single-sided PCR of the first step, and an oligonucleotide having the nucleotide sequence shown in SEQ ID NO: 30 (primer name: NG039) was used as an as anti-sense primer for the single-sided PCR of the second step. As non-specific primers, the nucleotide sequences of SEQ ID NOS: 12–15 and 20 were used as above (FIG. 6).

In order to establish the sequences, the sequences corresponding to nt1109–1575 (SEQ ID NO: 31, Clone T10), nt12–759 (SEQ ID NO: 32, Clone T14), and nt3119–3315 (SEQ ID NO: 33, Clone T8) were amplified by using oligonucleotides each having the nucleotide sequence shown in SEQ ID NO: 34 (primer name: NG013) and the nucleotide sequence shown in SEQ ID NO: 35 (primer name: NG025), oligonucleotides each having the nucleotide sequence shown in SEQ ID NO: 36 (primer name: NG040) and the nucleotide sequence shown in SEQ ID NO: 37 (primer name: NG046), and oligonucleotides each having the nucleotide sequence shown in SEQ ID NO: 38 (primer name: RD057) and the nucleotide sequence shown in SEQ ID NO: 39 (primer name: RD058) as the primer pair, respectively, amplification products were cloned as above, and the sequences were analyzed (FIG. 6).

The sequences of the obtained clones were combined to afford the sequence of the full length 3739 bp shown in SEQ ID NO: 1. Upon constructing the sequence, when mutations were observed in sequences overlapped between clones (different among clones), preference was given to the most frequent nucleotide.

For the sequence of nt1455–3054 in the obtained sequence, known gene sequences were searched based on homology by using databases (DDBJ, National Genetics Institute, search programs: BLAST and FASTA). Among the 20 genes exhibiting the highest homology, only Simian cytomegalovirus major immediate early transcription unit IE94 was derived from viruses, and its homology was 50.7% even for the fragment of 383-nucleotide length which exhibited the highest homology.

From the above, it was confirmed that any viral genes exhibiting high homology to the gene sequences according to the present invention over the full length have not been known, and the genes found by according to the present invention have novel sequences.

Example 5

Detection of HNT22 Genes in Blood Donors Who were Negative for non-B, non-C, non-G Hepatitis Virus Markers and Exhibited Abnormal Alanine Aminotransferase Values and Chronic Hepatitis Patients For 207 persons who were negative for known hepatitis virus markers and exhibited activity of alanine transferase (ALT) of 100 international unit (IU/l) or more, 26 persons who exhibited activity of γ-glutamyl transpeptidase (γ-GTP) of 500 IU/l or more, and 15 cases of non-B, non-C type chronic hepatitis all found in Japanese blood donors, presence of the HNT22 genes was examined by using the gene detection method of Example 2.

As controls, 88 blood donors with normal hepatic function and 22 patients of chronic hepatitis C were also examined.

As a result, the HNT22 genes were found in 16 persons out of the 207 persons with abnormally high ALT values (7.7%), 4 persons out of the 26 persons with abnormally high γ-GTP values (15.4%), and 3 patients out of the 15 non-B, non-C type chronic hepatitis patients (20%).

On the other hand, the HNT22 genes were found in 3 persons out of the 88 blood donors with normal hepatic function (3.4%), and 2 patients out of the 22 patients of chronic hepatitis C (9.1%).

Example 6

Detection of HNT22 Genes in Post-transfusion Hepatitis Cases

For post-transfusion hepatitis cases negative for known hepatitis virus markers, presence and timing of appearance of the HNT22 genes were examined in blood of patients before blood transfusion, after blood transfusion and before crisis of hepatitis, after crisis of hepatitis, and blood for transfusion (if possible) by the method of Example 2.

(1) Case 1

Post-transfusion hepatitis case, male, 63 years old.

This case was negative for any of markers of HBV, HCV and GBV-C/HGV throughout the examination period. ALT value, which is a hepatic function marker, was normal before blood transfusion, but abnormal values were observed eight weeks and nine weeks after the blood transfusion. Blood of this case was assayed for the HNT22 genes before the blood transfusion (represented as 0 week after blood transfusion) and 6, 8, 9, 10, 11, 12, 15, and 24 weeks after the blood transfusion. As a result, the HNT22 genes were detected from patient blood serum even before the blood transfusion (Table 1). The blood transfused to this case consisted of 4 units. When presence of the HNT22 genes in these transfusion blood units was examined, the HNT22 genes were detected in 1 unit.

TABLE 1

| Blood collection (week) | ALT (IU/L) | HCV antibody | GBV-C/HGV RNA | HNT22 gene 1st PCR | HNT22 gene 2nd PCR |
|---|---|---|---|---|---|
| 0 | 11 | − | − | + | + |
| 6 | 62 | − | − | NT | NT |
| 8 | 109 | − | − | NT | NT |
| 9 | 443 | − | − | + | + |
| 10 | 148 | − | − | + | + |
| 11 | 41 | − | − | − | + |
| 12 | 20 | − | − | − | + |
| 15 | 33 | − | − | + | + |
| 24 | 19 | − | − | − | + |

NT: not tested (2) Case 2

Post-transfusion hepatitis case, male, 58 years old.

This case was negative for any of markers of HBV, HCV and GBV-C/HGV throughout the examination period. ALT value, which is a hepatic function marker, was normal before blood transfusion, but abnormal values were observed around 10 weeks after the blood transfusion. Blood of the patient of this case was assayed for the HNT22 genes 2, 6, 8, and 10 weeks after the blood transfusion. As a result, the HNT22 genes were detected from patient blood sera at 6, 8 and 10 weeks after the blood transfusion in the 1st PCR of the first amplification step (Table 2). In contrast, at 2 weeks, the titer was low, and detected only in the 2nd PCR. The blood transfused in this case was not preserved, and therefore presence of the HNT22 genes in the transfused blood could not be confirmed.

This example is a case where Clone #22 of HNT22 was isolated. It was found that the virus was present in the blood at two weeks which was used as a driver for the isolation. However, because it could be detected only in the highly sensitive second step of the amplification, the amount of the virus at that point was quite small, and therefore it substantially functioned as a driver.

TABLE 2

| Blood collection (week) | ALT (IU/L) | HCV antibody | GBV-C/HGV RNA | HNT22 gene 1st PCR | HNT22 gene 2nd PCR |
|---|---|---|---|---|---|
| 2 | 36 | − | − | − | + |
| 6 | 37 | − | − | + | + |
| 8 | 55 | − | − | ++ | + |
| 10 | 180 | − | − | ++ | + |

(3) Case 3

Post-transfusion hepatitis case, male, 56 years old.

This case was also negative for any of markers of HBV, HCV and GBV-C/HGV throughout the examination period. ALT value, which is a hepatic function marker, was normal before blood transfusion, but abnormal values were observed around 6 weeks after the blood transfusion. Blood of the patient of this case was assayed for presence of the HNT22 genes before the blood transfusion (represented as 0 week after blood transfusion) and 2, 4, 6, 8, 12, 13 weeks, 4 and 5 months after the blood transfusion by utilizing PCR comprising the two-step amplification according to the method of Example 2. Serial 10-fold dilutions of the samples were also prepared and assayed in the same manner, thereby the titer of the viral genes (considered to be the amount of the virus) was determined from the maximum dilution ratios where the gene was detected. As a result, while the blood 2 weeks after the blood transfusion was negative, the HNT22 genes were detected in each blood 6 weeks to 4 months after the blood transfusion (Table 3). On the other, aberration of hepatic function became significant from 6 weeks after the blood transfusion, and then gradually ameliorated, and this process was well conformed to the variation of the viral amount. The blood transfused in this case was not preserved, and therefore presence of the HNT22 genes in the transfused blood could not be confirmed.

TABLE 3

| Blood collection (week) | ALT (IU/L) | HCV antibody | GBV-C/HGV RNA | HNT22 gene 1st PCR | HNT22 gene 2nd PCR |
|---|---|---|---|---|---|
| 0 | 17 | − | − | − | − |
| 2 | 36 | − | − | − | − |
| 4 | 34 | − | − | − | + |
| 6 | 192 | − | − | − | + |
| 8 | 172 | − | − | − | + |

(4) Case 4

Post-transfusion hepatitis case, female, 70 years old

This case was also negative for any of markers of HBV, HCV and GBV-C/HGV throughout the examination period. ALT value, which is a hepatic function marker, was normal before blood transfusion, but abnormal values was observed around 6 weeks after the blood transfusion. Blood of the patient of this case was assayed for presence of the HNT22 genes 4, 6, 8, 11, 12, 15, 16, 17 and 21 weeks after the blood transfusion by utilizing PCR comprising the two-step amplification according to the method of Examples 2 and 3, and presence of the HNT22 genes and the titer of the viral genes were also determined as in Case 3 (similar results were obtained by the methods of Examples 2 and 3). As a result, while the blood at 4 weeks after the blood transfusion was negative, the titer increased from 6 weeks after the blood transfusion, and the highest titer was observed at 11 weeks when the aberration of hepatic function was the most significant. Then, as the virus disappeared, the hepatic function was normalized, and thus the variations of the viral amount and the hepatic function were well conformed to each other (Table 4). The blood transfused in this case was not preserved, and therefore presence in the HNT22 genes in the transfused blood could not be confirmed. When presence of HNT antibodies was assayed by the method described in Example 13, it was positive after the crisis.

TABLE 4

| Blood collection (week) | ALT (IU/L) | HCV antibody | GBV-C/HGV RNA | HNT22 gene 1st PCR | HNT22 gene 2nd PCR | HNT antibody |
|---|---|---|---|---|---|---|
| 4 | 14 | − | − | − | − | − |
| 6 | 15 | − | − | − | + | NT |
| 8 | 10 | − | − | + | + | NT |
| 11 | 140 | − | − | ++ | + | NT |
| 12 | 36 | − | − | − | + | NT |
| 15 | 16 | − | − | − | − | NT |
| 16 | 7 | − | − | − | − | NT |
| 17 | 4 | − | − | − | − | NT |
| 21 | 7 | − | − | − | − | + |

NT: not tested

Example 7

Analysis of Blood Transfusion Infection Cases

The facts that the HNT22 genes of the present invention were detected in Example 6 in the cases of post-transfusion hepatitis which was negative for known hepatitis markers and whose cause was indistinct, and that the variation of abnormal value of the hepatic function marker well conformed to the variation of the viral amount strongly suggested that HNT22 was a cause of the hepatitis. This example was performed aiming at more clearly demonstrating that HNT22 is transmitted by blood transfusion. That is, for cases having blood transfusion history where the HNT22 genes were detected in blood after blood transfusion and all of the blood pilots used for the transfusion were preserved, blood after blood transfusion and the blood pilots were assayed for the genes by the method described hereinafter to identify blood transfusion pilots positive for the gene and considered to be the source of infection. Further, sequences of the genes obtained from the patients' blood and the pilots were determined, and compared to examine their sequence homology.

For the cases determined positive for the HNT22 genes by the method described in Example 2 after blood transfusion, it was determined if the HNT22 genes could be detected in blood before blood transfusion and blood pilots used for blood transfusion. As a result, while the HNT22 genes could not be detected in blood samples before blood transfusion, it was detected in all samples at 2 weeks after blood transfusion and thereafter. Therefore, it was strongly suggested that the infection was brought by the blood transfusion.

Further, all of the ten blood pilots used were assayed for the HNT22 genes, and the HNT22 genes were detected in one pilot among them. Nucleic acids were extracted from all of the samples positive for HNT22 according to the method described in Example 2. Then, they were amplified as in Example 2 by replacing the sense primer RD037 in the 1st PCR of Example 2 with the primer NG001 having the nucleotide sequence shown in SEQ ID NO: 40, and changing the PCR condition to 35 cycles of a cycle of 94° C. for 30 seconds, 55° C. for 30 seconds, and 72° C. for 1 minute. When amplified under the above conditions, a DNA fragment of 415 bp was provided in the positive cases. The second step of the amplification in Example 2 was performed by replacing the sense primer RD051 with NG001, and using PCR condition of a reaction cycle of 94° C. for 30 seconds, 55° C. for 30 seconds, and 72° C. for 1 minute repeated 25 times. When amplified under these conditions, a DNA fragment of 396 bp was provided in the positive cases. This 396 bp amplification product was cloned by inserting it into a plasmid vector as in Example 1, and nucleotide sequences were determined and compared for 3 clones for each amplification to examine homology.

As a result, the sequences of the clones obtained from the blood pilots for blood transfusion that were positive for HNT22 were completely conformed with the HNT22 gene sequence obtained from the patients transfused with the pilots (FIG. 7). This demonstrated that HNT22 virus was transmitted by blood transfusion, and became persistent. When this gene sequence was compared with the sequence of Clone #22, 3 nucleotides were different among 356 nucleotides other than those derived from the primers for the both ends.

Example 8

Verification of the Fact that the Virus of the Present Invention is DNA Virus As hepatitis viruses, there are DNA viruses like HBV, and RNA viruses like HCV. Which kind of viruses the virus of the present invention belongs to was determined by the following procedure.

(1) PCR which Omits Reverse Transcription Reaction Step

As described in Example 1, the samples of the isolated genes of the present invention undergone a step of reverse transcription reaction after the nucleic acid extraction. Accordingly, the samples after the reverse transcription reaction contains DNA which were originally present and DNA which had been present as RNA before the reaction and were converted into DNA by the reverse transcription reaction. Therefore, if the virus of the present invention is an RNA virus, detection of the gene of the virus should become impossible or quite difficult when the reverse transcription reaction is omitted.

Based on the above, the present inventors performed PCR according to the procedure of Example 2 that omitted the reverse transcription reaction to examine the above possibility. As a result, it was confirmed that the HNT22 genes could be detected at a similar level even without the reverse transcription reaction.

HNT22 was confirmed to be a DNA virus from the above.

(2) Verification by Deoxyribonuclease Treatment

In addition to the analysis of the above (1), the present inventors treated a nucleic acid fraction extracted from a sample confirmed by the method of Example 2 to contain the HNT22 genes with a deoxyribonuclease, and subjected to reverse transcription reaction, and the resulted product was assayed as a sample for the HNT22 genes by the method of Example 2.

Specifically, a nucleic acid fraction extracted by using the same commercially available kit as Example 2 (EX R&D, Sumitomo Metal) was treated with DNase I (Takara Shuzo) at 37° C. for 30 minutes, and then activity of DNase I was inhibited. For this sample, detection of the HNT22 genes was attempted by carrying out the procedure of Example 1 after the reverse transcription under the same condition. As a result, it was found that the HNT22 genes became undetectable after the treatment of DNase I.

The results of the above (1) and (2) demonstrated that HNT22 virus of the present invention is a DNA virus.

Example 9

Verification of the Fact that the Virus of the Present Invention is a Single-stranded DNA Virus (1) Verification Utilizing Restriction Endonuclease It has been known that there are two kinds of viruses having different gene structures among DNA viruses, i.e., those having a single-stranded DNA and those having a double-stranded DNA. The present inventors considered it is important to determine which kind of the viruses the virus of the present invention belongs to in view of elucidating the identity of the HNT22 virus, and performed the following experiment.

If it is assumed that the HNT22 virus gene exists in a double-stranded state in nature, there would be several sites specific for restriction endonucleases in its sequence. However, if the viral gene is single stranded, there would be no such restriction endonuclease specific sequences. Conversely, if extracted genes are susceptible to (cleaved by) restriction endonucleases specific for the above sequences, the genes of the virus of the present invention have a double-stranded structure.

Based on the above idea, the present inventors examined if there is a cleavage with a restriction endonuclease EcoRI for which a specific sequence would be present in the sequence of the HNT22 genes when they are assumed to be double-stranded, or with a restriction endonuclease Bg/II for which a specific sequence would not be recognized as control.

DNA (90 µl) was obtained using the method described in Example 1 from plasma (800 µl) obtained from patients confirmed to be positive for HNT22 virus by the methods of Examples 2 and 3. A 15 µl aliquot of each DNA was taken, added with 2 µl of EcoRI (Takara Shuzo) or Bg/II (Takara Shuzo), and incubated at 37° C. for 2.5 hours. In parallel, the same reaction was performed by adding phosphate buffer instead of the restriction endonucleases. After the treatment with the restriction endonucleases, 3 µl aliquot was taken from each sample, 10-fold and 100-fold dilution samples were prepared from it, and it was attempted to amplify a HNT22 gene region containing the EcoRI restriction endonuclease specific sequence for each sample by using the primers NG001 and RD038 which contained an EcoRI restriction endonuclease specific sequence within them. As a result, no cleavage by restriction endonuclease was recognized in any of the samples.

(2) Verification by Mung Bean Nuclease Treatment

Mung bean nuclease has been known to specifically cleave a single-stranded DNA. Therefore, it is considered that if HNT22 exists as a single strand, it would be susceptible to mung bean nuclease.

Based on the above idea, the present inventors obtained DNA from the same patient used for the restriction endonuclease treatment experiment in the same manner, and treated with mung bean nuclease. As a control, a partial region of HNT22 amplified by the method of Example 2 was introduced into phage M13, and a double-stranded one and a single-stranded one were prepared, and subjected to mung bean nuclease treatment. Then, the HNT22 genes were amplified according to the method of Example 2. As a result, the DNA obtained from the HNT22 positive patient and the single-stranded DNA derived from the phage could not be amplified, and thus they were susceptible to mung bean nuclease.

From the above results of (1) and (2), it was confirmed that the HNT22 genes exist as a single-stranded DNA, and HNT22 virus is a single-stranded DNA virus.

Example 10

Amino Acid Sequences Encoded by HNT22 Genes

Based on the HNT22 gene sequences identified in Example 4, the amino acid sequences encoded by the HNT22 genes were analyzed. Initiation codon sequence and termination codon sequence were searched in the nucleotide sequences obtained, and opening reading frame (ORF) of the HNT22 genes was searched by considering which combination thereof would afford an ORF in a usually expected size as a determination criterion. As a result, it was found that there were two ORFs, ORF1: nt589–nt2898 (770 amino acid residues), and ORF2: nt107–nt712 (202 amino acid residues) (FIG. 6 and FIG. 8). From the above, it can be assumed that the HNT22 genes encode polypeptides comprising the amino acid sequences shown in SEQ ID NOS: 9 and 10.

Based on these amino acid sequences, hydrophobicity/hydrophilicity characteristics of the encoded polypeptides were analyzed in a conventional manner (FIG. 9).

Example 11

Isolation of Virus Particles

Blood that had been found to be positive for the HNT22 genes by the method of Example 2 was fractionated by using sucrose density gradient centrifugation to analyze the density distribution of the HNT22 genes, and the possibility to be a virus particle was examined based on the density distribution analysis.

(1) Blood positive for the HNT22 genes (250 µl) and plasma positive for HBV (5 µl) as a control were mixed, and centrifuged at 15000 revolutions/minute for 5 minutes by using a refrigerated microcentrifugal separator to precipitate impurities, which were then removed.

(2) The supernatant obtained in the procedure of the above (1) (0.2 ml) was added to a density gradient carrier formed in a centrifugation tube for Beckman SW60 rotor by overlaying layers of sucrose solution having gradient concentrations in the order of 60% (0.7 ml), 50%, 40%, 30%, 20% and 10% (0.2 ml for each) by weight from the bottom, and TEN buffer (2.3 ml, 10 mM Tris-HCl, pH 8.0, 1 mM EDTA, 0.5 M NaCl) was overlaid thereon.

(3) After centrifugation at 40000 revolutions/minute at 10° C. for 45 hours, 300 µl portion was collected from the bottom of each tube, and subjected to density measurement using a refractometer.

(4) A 100 µl portion was collected from each density fraction, mixed with an extraction reagent (300 µl, Okamoto H. et al., J. Virol. 64:1298–1303, 1990) containing proteinase K (Boehringer Mannheim) and sodium dodecylsulfate (SDS, Wako Pure Chemicals Industries), and allowed to react at 70° C. for 3 hours. The nucleic acid fraction was extracted by adding phenol, and further extracted with phenol and chloroform. Finally, the nucleic acids were precipitated by adding ethanol, and collected, and then dissolved in TE buffer (10 mM Tris-HCl, pH 8.0, 1.0 mM EDTA) to a suitable concentration.

(5) By using the obtained DNA as samples, the HNT22 genes were amplified by the method of Example 2, and the HBV gene was amplified and detected as follows.

A DNA sample (5 µl) was added to a PCR tube containing an amplification reaction mixture comprising a primer S1-2 having the nucleotide sequence shown in SEQ ID NO: 41 and a primer S2-1 having the nucleotide sequence shown in SEQ ID NO: 42 (0.5 µl for each, 10 OD/ml), which were selected from sequences within a surface antigen gene region of HBV, 2.5 mM dNTP (4 µl), buffer for thermostable DNA polymerase at 10-fold concentration (5.0 µl, buffer attached to AmpliTaq DNA polymerase, Perkin Elmer), thermostable DNA polymerase (0.25 µl, AmpliTaq DNA Polymerase, Perkin Elmer), and distilled water (34.75 µl), overlaid with mineral oil (50 µl), stirred, and centrifuged at 5000 rpm for 30 seconds, and the tube was mounted on a thermal cycler to performed PCR. PCR was performed with a cycle of 94° C. for 30 seconds, 55° C. for 30 seconds, and 72° C. for 75 seconds repeated for 35 cycles. In this method, the HBV gene could be detected as a band of a length of 250 bp in electrophoresis gel. When more sensitive detection was required, second PCR was performed by using a portion of the above amplification product as follows. That is, the amplification product (5 µl) was added to the same reaction solution as above except that the primers used were changed to a primer $088 having the nucleotide sequence shown in SEQ ID NO: 43 and a primer S2-2 having the nucleotide sequence shown in SEQ ID NO: 44, and treated in the same manner as above. Then, PCR was performed with a cycle of 94° C. for 30 seconds, 55° C. for 30 seconds, and 72° C. for 60 seconds, which was repeated 25 times. The amplification product provided by the second PCR was detected in the electrophoresis gel as a band of 228 bp.

As a result of the above assay, the HNT22 genes existed as a peak at a sucrose concentration of 54.5%, and density of 1.26 g/cm$^3$, whereas the HBV as the control existed as a peak at a density of 1.26–1.20 g/cm³ as previously reported (Table 5). This density analysis indicated that the HNT22 genes existed in the virus particle fraction, and it was demonstrated that they can be collected in the density fraction mentioned above by density gradient centrifugation.

TABLE 5

Distribution of HNT22 genes in sucrose density gradient centrifugation fractions

| Sucrose density (%) | Density (g/ml) | HNT22-DNA 1st PCR | HNT22-DNA 2nd PCR | HBV-DNA 1st PCR | HBV-DNA 2nd PCR |
|---|---|---|---|---|---|
| 60.7 | 1.29 | + | + | − | + |
| 54.5 | 1.26 | ++ | + | +++ | + |
| 45.2 | 1.20 | ± | + | +++ | + |
| 30.9 | 1.13 | ± | + | ++ | + |
| 19.5 | 1.08 | − | + | + | + |
| 12.0 | 1.05 | − | − | + | + |

−: Negative,
±: Weakly positive,
+: Positive,
++: Fairly positive,
+++: Strongly positive Example 12

HNT22 Genotype Sequences

Because it had been suggested that HNT22 had several genotypes as mentioned in Example 3, the present inventors searched genotypes of HNT22 by analyzing the amplified genes of 22 HNT22 positive cases which had been determined positive by the gene detection method of Example 3, and preparing a molecular phylogenetic tree based on the gene sequences.

The present inventors examined Japanese, Americans, and Frenchmen for the presence of the HNT22 genes by the method described in Example 3, and as a result obtained 199 positive cases (187 Japanese cases, 8 American cases, 4 Frenchman cases). Amplified genes of these positive cases were cloned according to the method described in Example 1, and sequenced for at least 3 clones for each, and a phylogenetic tree was prepared by using a commercially available software (FIG. 10, sequences are shown in FIGS. 11–12). As a result, the HNT22 genes were classified into 10 types having the sequences shown in SEQ ID NOS: 45–54 (corresponding to nt1939–2160 of SEQ ID NO: 1). The present inventors designated them as Genotypes 1, 2, 3, 4, 5, 6, 7, 8, 9 and 10, respectively.

Example 13

Anti-HNT22 Antibody Detection Method by Immunoprecipitation Utilizing Isolated HNT22 Virus Particles It was demonstrated that the HNT22 particles can be isolated and collected by the method of Example 11. The present inventors studied detection of antibodies by immunoprecipitation based on the above finding.

First, feces were collected from HNT infected patients who had been found to have the HNT22 genes in their blood, and suspended in a suitable solvent to prepare samples, and presence of the HNT22 genes in the feces was examined according to the method of Example 3. As a result, it was found that the HNT22 genes were also present in the feces, their buoyant density was 1.35 g/cm³, and the gene sequence was identical to the gene sequence of HNT22 obtained from blood of the same patients. Therefore, it was decided to collect HNT22 particles from feces.

Distilled water was added to feces obtained from a patient to prepare a 15% (weight concentration) suspension. This suspension was centrifuged at 3000 rpm for 30 minutes by using a refrigerated centrifugal separator (Hitachi) to afford a supernatant. This supernatant was further centrifuged at 10000 rpm for 5 minutes by using a refrigerated microcentrifugal separator (High Apeed Micro Refrigerated Centrifuge, Tomy Seikou). The supernatant was collected as HNT22 particle suspension. DNA titer of the particle suspension was $10^5$/ml.

The above HNT22 particle suspension (10 μl) was added to serum or plasma (50 μl), and allowed to react at 37° C. for 24 hours. After the reaction, goat anti-human IgG (50 μl, #46340, Cappel) was added as second antibodies as its stock solution, and allowed to react at 37° C. for one hour. After completion of the reaction, the mixture was centrifuged at 10000 rpm for 5 minutes using a refrigerated microcentrifugal separator (High Apeed Micro Refrigerated Centrifuge, Tomy Seikou) to be isolated into a supernatant and precipitates. The supernatant was transferred into a separate Eppendorf tube, and DNA was extracted by using a commercially available nucleic acid extraction kit (EX R&D, Sumitomo Metal). On the other hand, physiological saline (110 μl) was carefully added to the precipitates, and centrifuged at 10000 rpm for 5 minutes. The supernatant was discarded, and the residue was suspended in physiological saline (110 μl) added dropwise. DNA was extracted from this suspension in the same manner as above. The obtained DNA fraction was dissolved in distilled water (20 μl), and treated at 95° C. for 5 minutes, and a half amount of the obtained solution was used as a sample for HNT22 gene detection. Detection of the HNT22 genes was performed in the same manner as in Example 3. The same serum or plasma treated in the same manner without adding the HNT22 particles, and serum or plasma negative for HNT22 treated in the same manner as above were used as controls.

As a result, the HNT22 genes were found in the precipitate fraction of the HNT22 gene positive blood serum or plasma, whereas the HNT22 genes were not found in the precipitate fraction when the particle suspension was not added, or HNT negative serum or plasma was used. From these results, it is considered that only when HNT22 antibodies are present, HNT22 particles aggregate with these antibodies and the anti-human IgG antibodies to form a precipitate fraction, and conversely, in a case where the HNT genes are present in the precipitate fraction, the anti-HNT antibodies are present.

Example 14

Measurement of Anti-HNT22 Antibody in Post-transfusion Hepatitis Cases and Fulminant Hepatic Failure Cases by Anti-HNT22 Antibody Detection Method Utilizing HNT Particle Suspension The present inventors examined presence or absence of the anti-HNT22 antibodies for Case 4 mentioned in Example 6 who had transiently infected by HNT22 after blood transfusion and exhibited hepatic function aberration, and convalescence cases of sporadic fulminant non-A-G hepatic failure whose infection of known hepatitis viruses had been denied by using the method of Example 13 (Tables 4 and 6).

As a result, it was demonstrated that anti-HNT22 antibodies appeared after disappearance of the virus for the both cases, and exhibited appearance and disappearance pattern similar to that of the neutralizing antibodies observed in viral infection.

TABLE 4

Appearance and disappearance of HNT22 gene and anti-HNT22 antibody in convalescence patients of sporadic fulminant non-A-G hepatic failure

| Blood collection (day) | ALT (IU/L) | HCV antibody | GBV-C/HGV RNA | HNT22 gene 1st PCR | HNT22 gene 2nd PCR | HNT antibody |
|---|---|---|---|---|---|---|
| 0 | 2568 | − | − | + | − | − |
| 2 | 523 | − | − | + | + | NT |
| 7 | 152 | − | − | ++ | + | NT |
| 18 | 28 | − | − | + | + | NT |
| 31 | 16 | − | − | − | + | NT |
| 38 | 9 | − | − | − | − | + |

NT: not tested
After admission ALT HCV GBV-C/HGV
Blood collection day (IU/I) antibody RNA Example 15

Detection and Sequencing of HNT22 Gene Subspecies

Because it was demonstrated that a plurality of genotypes existed for HNT22 virus (Example 12), and other viruses such as hepatitis B and C viruses show regional bias of genotypes, major HNT22 genotypes in the U.S.A. may be different from the Japanese major types. Therefore, HNT22 positive samples obtained from Americans were examined.

Nucleic acids were extracted from 100 µl each of sera from Americans confirmed to be HNT22 virus positive by the method described in Example 3 (designated as UM3-17, UM3-34, UM3-56, and UM3-73, respectively) by using a commercially available nucleic acid extraction kit (High Pure Viral Nucleic Acid Kit, Boehringer Mannheim) according to the attached instructions to prepare samples.

PCR was performed by using an oligonucleotide having the nucleotide sequence shown in SEQ ID NO: 55 (NG055) and an oligonucleotide having the nucleotide sequence shown in SEQ ID NO: 8 (NG063) selected based on the identified sequence of HNT22 virus as primers, and the samples obtained above as templates, and according to the following conditions. The locational relation of the primers used is shown in FIG. 13.

PCR Conditions
(1) Reaction Mixture Composition

| | |
|---|---|
| Template nucleic acid solution | 10 µl |
| 10 × Ex. Taq buffer | 5 µl |
| 2.5 mM dNTP | 4 µl |
| Primer (NG055: 10 OD/ml) | 1 µl (OD at 280 nm, same shall apply hereinafter) |
| Primer (NG063: 10 OD/ml) | 1 µl |
| Distilled water | 29.5 µl |
| Ex. Taq DNA polymerase | 1 µl |
| Total | 50 µl |

(2) Reaction Condition

| | | |
|---|---|---|
| 95° C. | 2 minutes | |
| 95° C. | 45 seconds | |
| 55° C. | 30 seconds | 35 cycles |
| 72° C. | 90 seconds | |
| 72° C. | 7 minutes | |

As a result, gene amplification was obtained for all of the samples. A plurality of amplification fragments were cloned into T vector for each sample in the same manner as in Example 1, and the gene sequences were determined. As a result, from UM3-17 and UM3-73, clones exhibiting high homology to the already identified nucleotide sequences and, in addition, clones having a sequence exhibiting low homology to those sequences were obtained (referred to as U17-2 and U73-2 respectively hereinafter). Both of the sequences exhibited 30% homology to a corresponding region of the nucleotide sequences identified so far. From UM3-56 and UM3-34, only nucleotide sequences exhibiting high homology to the nucleotide sequences already identified were obtained.

An oligonucleotide (NT01) having the nucleotide sequence shown in SEQ ID NO: 56 was prepared as a primer for further amplifying a nucleotide sequence of 5' end of the above clone, based on comparison of sequences between the U17-2 done obtained above and HNT22 virus identified so far, and selection of a highly conserved region. PCR was performed by using this oligonucleotide NT01 and an oligonucleotide having the nucleotide sequence shown in SEQ ID NO: 57 (NG054) prepared based on the sequence of HNT22 virus already identified as primers, and a nucleic acid derived from UM3-17 as a template, and according to the following conditions. The obtained amplification fragment was sequenced in the same manner as described above. The locational relation of the primers used is shown in FIG. 13.

PCR Conditions
(1) Reaction Mixture Composition

| | |
|---|---|
| Template nucleic acid solution | 10 µl |
| 10 × Ex. Taq buffer | 5 µl |
| 2.5 mM dNTP | 4 µl |
| Primer (NT01: 10 OD/ml) | 1 µl |
| Primer (NG054: 10 OD/ml) | 1 µl |
| Distilled water | 29.5 µl |
| Ex. Taq DNA polymerase | 1 µl |
| Total | 50 µl |

(2) Reaction Condition

| | | |
|---|---|---|
| 95° C. | 2 minutes | |
| 95° C. | 45 seconds | |
| 55° C. | 30 seconds | 35 cycles |
| 72° C. | 90 seconds | |
| 72° C. | 7 minutes | |

On the other hand, oligonucleotides having the nucleotide sequences shown in SEQ ID NOS: 58 and 59 (primers NT03 and NT04, respectively) were prepared as primers for further amplifying a sequence of 3' end of the above clones, based on the 3' end nucleotide sequence of U17-2 and the already identified sequence of HNT22 virus, and oligonucleotides having the nucleotide sequences shown in SEQ ID NOS: 60 and 61 (primer NG065 and NG021, respectively) were prepared as primers for amplification, based on an already identified sequence around the 3' end of the nucleotide sequence of HNT22 virus. First, gene of 3' end was amplified by using NT03 and NG065, and a part of the obtained amplification fragment was amplified by using NT04 and NG065 or NG021. The locational relation of the primers used is shown in FIG. 13. The amplification was performed with the following conditions by using a nucleic acid derived from UM3-17 as a template. The nucleotide sequence of the amplification fragment was determined in the same manner as described above.

PCR Conditions

First Step PCR (1) Reaction Mixture Composition

| | |
|---|---|
| Template nucleic acid solution | 10 μl |
| 10 × Ex. Taq buffer | 5 μl |
| 2.5 mM dNTP | 4 μl |
| Primer (NG03: 10 OD/ml) | 1 μl |
| Primer (NG065: 10 OD/ml) | 1 μl |
| Distilled water | 29.5 μl |
| Ex. Taq DNA polymerase | 1 μl |
| Total | 50 μl |

(2) Reaction Condition

| | | |
|---|---|---|
| 95° C. | 2 minutes | |
| 95° C. | 45 seconds | |
| 55° C. | 30 seconds | 35 cycles |
| 72° C. | 90 seconds | |
| 72° C. | 7 minutes | |

Second Step PCR (1) Reaction Mixture Composition

| | |
|---|---|
| Template nucleic acid solution | 5 μl |
| 10 × Ex. Taq buffer | 5 μl |
| 2.5 mM dNTP | 4 μl |
| Primer (NT04: 10 OD/ml) | 0.5 μl |
| Primer (NG065: 10 OD/ml) or Primer (NG021: 10 OD/ml) | 0.5 μl |
| Distilled water | 34.5 μl |
| Ex. Taq DNA polymerase | 0.5 μl |
| Total | 50 μl |

(2) Reaction Condition

| | | |
|---|---|---|
| 95° C. | 2 minutes | |
| 95° C. | 45 seconds | |
| 55° C. | 30 seconds | 20 cycles |
| 72° C. | 90 seconds | |
| 72° C. | 7 minutes | |

From the above procedure, clones 1-1, 1-9 and 1-10 were obtained as 5' end sequence clones of U17-2, and 2A-3 (when the primers in the second step PCR were the combination of NT04/NG065), and 2B-1 and 2B-3 (when the primers in the second step PCR were the combination of NT04/NG021) were obtained as 3' end sequence clones. Nucleotide sequences of these clones were determined in the same manner as described above, and ligated to obtain a nucleotide sequence of virus gene detected from sera derived from Americans (SEQ ID NO: 62).

By comparing this sequence with the nucleotide sequences of the HNT22 genes, it was found that extremely high homology can be observed for the 5' end and 3' end sequences whereas homology of the other sequences was as low as around 30%, and this sequence could not be detected by the detection methods of Examples 2 and 3. The virus having this gene was designated as TUS01.

The nucleotide sequence of the TUS01 gene was searched for ORF in the same manner as in Example 10. As a result, it was found that two ORFs, ORF1: nt590–nt2872 (761 amino acid residues) and ORF2: nt258–nt725 (156 amino acid residues) were present (FIG. 15). These existed at locations corresponding to those of ORF1 and ORF2 in the nucleotide sequence of the HNT22 genes.

Homology of each region was summarized in Table 7.

TABLE 7

Homology of HNT22 gene and TUS01 gene

| | HNT22[2)] | TUS01 | Sequence homology |
|---|---|---|---|
| Full length | 3739nt | 3722nt | 63.7% |
| 5' untranslated region | 262 nt | 257 nt | 90.3% |
| Translated region | 2636 nt | 2615 nt | 54.7% |
| ORF1 | 2310 nt | 2283 nt | 54.8% |
| (Amino acid sequence) | 770 aa | 761 aa | 37.0% |
| ORF2[1)] | 450 nt | 468 nt | 55.5% |
| (Amino acid sequence) | 150 aa | 156 aa | 38.8% |
| 3' untranslated region | 841 nt | 850 nt | 84.2% |

[1)]For ORF2, to make comparison based on TUS01, the frame from the second ATG codon was employed for HNT22.
[2)]Sequence used as HNT22 was that of TA278.

The results of the comparison of nucleotide sequences of highly homologous 5' untranslated region (5' end region) and 3' untranslated region (3' end region) are shown in FIGS. 15 and 16.

When homology of the nucleotide sequence of the TUS01 gene with known sequences was determined by using FAST and BLAST in the same manner as in Example 4, all of those exhibiting high homology were nucleotide sequences of the HNT22 genes.

Judging from the above-mentioned characteristics, TUS01 virus is assumed to be a subspecies of HNT22 virus.

Example 16

Simultaneous Detection of HNT22 Gene and TUS01 Gene

A method capable of simultaneously detecting the TUS01 gene, which cannot be detected by the methods of Examples 2 and 3, was studied.

By comparing the both sequences, as oligonucleotides containing a common sequence and considered to be suitable as PCR primers, NG054 and NG065 were selected. Nucleic acids were extracted from blood serum (100 μl) according to the method described in Example 2. The extracted nucleic acids were dissolved in distilled water (10 μl). The dissolved nucleic acids (10 μl) were added to a tube exclusively for PCR containing solutions of NG054 and NG065 (1 μl, 10 OD/ml for each), Ex. Taq buffer at 10-fold concentration (5 μl, TaKaRa Shuzo), 2.5 mM dNTP (4 μl), and distilled water (29.5 μl), immediately added with thermostable DNA polymerase (Ex. Taq Polymerase: TaKaRa Shuzo), and amplified by treatment at 95° C. for 2 minutes, followed by a cycle of 95° C. for 45 seconds, 55° C. for 30 seconds, and 72° C. for 120 seconds, which was repeated 35 times, and finally a reaction at 72° C. for 7 minutes. The amplification products were separated by agarose gel electrophoresis, and presence of bands of lengths predicted from the nucleotide sequences was confirmed. The amplification products for which bands were confirmed were sequenced. As a result, it was found that the HNT22 gene and the TUS01 gene could be simultaneously detected by this method.

INDUSTRIAL APPLICABILITY

According to the present invention, a so far unknown etiologic virus of blood-borne infectious hepatitis whose cause had been indistinct was identified. This enables establishing methods for gene assay, antigen assay, and antibody assay, and providing kits for test of the hepatitis, and vaccines for prevention thereof.

What is claimed is:

1. A method for detecting a non-B, non-C, non-G hepatitis virus gene wherein PCR is performed by using the oligonucleotides selected from the group consisting of a nucleotide sequence shown in SEQ ID NO: 57, a nucleotide sequence shown in SEQ ID NO: 60, and a nucleotide sequence shown in SEQ ID NO: 61 as primers.

2. A method for detecting a non-B, non-C, non-G hepatitis virus gene wherein PCR is performed by using an oligonucleotide having a nucleotide sequence shown SEQ ID NO: 57 and an oligonucleotide having a nucleotide sequence shown in SEQ ID: 60, or an oligonucleotide having a nucleotide sequence shown in SEQ ID NO: 57 and an oligonucleotide having a nucleotide sequence shown in SEQ ID NO: 61 as primers.

3. An isolated non-B, non-C, non-G hepatitis virus genome comprising:
   (a) a DNA having the nucleotide sequence shown in SEQ ID NO: 1 or 62, or
   (b) a DNA which hybridizes with the DNA of (a) under stringent conditions of 24 mM Tris-HCl, pH 7.5/2.4 mM EDTA/1M NaCl at 67° C.

4. The genome according to claim 3, which comprises the DNA having the nucleotide sequence shown in SEQ ID NO: 1 or 62.

* * * * *

UNITED STATES PATENT AND TRADEMARK OFFICE
CERTIFICATE OF CORRECTION

PATENT NO. : 6,849,431 B2
DATED : February 1, 2005
INVENTOR(S) : Okamoto et al.

It is certified that error appears in the above-identified patent and that said Letters Patent is hereby corrected as shown below:

<u>Column 81,</u>
Line 57, "nucleotide sequence shown" should be changed to -- nucleotide sequence shown in --.
Line 59, "shown in SEQ ID: 60" should be changed to -- shown in SEQ ID NO: 60 --.

Signed and Sealed this

Twenty-ninth Day of November, 2005

JON W. DUDAS
*Director of the United States Patent and Trademark Office*